United States Patent
Wang et al.

(10) Patent No.: US 8,072,585 B2
(45) Date of Patent: *Dec. 6, 2011

(54) SYSTEM WITH EXTENDED RANGE OF MOLECULAR SENSING THROUGH INTEGRATED MULTI-MODAL DATA ACQUISITION

(75) Inventors: Xuefeng Wang, West Lafayette, IN (US); David D. Nolte, Lafayette, IN (US); Manoj Varma, Tripunithura (IN); Brian Weichel, W. Lafayette, IN (US); Timothy Norwood, Lafayette, IN (US); Fouad Sayegh, West Lafayette, IN (US); Ming Zhao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/650,692

(22) Filed: Dec. 31, 2009

(65) Prior Publication Data

US 2010/0145627 A1 Jun. 10, 2010

Related U.S. Application Data

(63) Continuation of application No. 12/018,108, filed on Jan. 22, 2008, now Pat. No. 7,659,968.

(60) Provisional application No. 60/885,698, filed on Jan. 19, 2007, provisional application No. 60/916,177, filed on May 4, 2007.

(51) Int. Cl.
 *G01N 21/00* (2006.01)
 *G01N 21/64* (2006.01)
(52) U.S. Cl. ........ 356/73; 356/417; 422/82.08; 436/172
(58) Field of Classification Search ............... 356/73
 See application file for complete search history.

(56) References Cited

U.S. PATENT DOCUMENTS 3,796,495 A 3/1974 Laub
(Continued)

FOREIGN PATENT DOCUMENTS

EP 1189062 A1 3/2002
(Continued)

OTHER PUBLICATIONS

Abe, Takao, et al., Microroughness Measurements on Polished Silicon Wafers, Jpn. 31, pp. 721-728, 1992.
(Continued)

*Primary Examiner* — F. L Evans
(74) *Attorney, Agent, or Firm* — Baker & Daniels LLP

(57) ABSTRACT

A multi-modal data acquisition system for detecting target material on a biological reaction surface, the system comprising a radiation source for generating an incoming beam that impinges on the biological reaction surface at an oblique incidence angle and produces a reflected beam, an interferometric detector for detecting an interferometric signal from the illuminated surface, the reflected beam being directed to the interferometric detector, a fluorescence detector for detecting a fluorescence signal from the illuminated surface; the fluorescence detector being positioned to substantially minimize the incidence of the reflected beam; and a processing system for receiving the interferometric and fluorescence signals and determining the presence or absence of target material on the biological reaction surface. A reaction surface conditioned for the simultaneous collection of fluorescence, interferometric and other signals. A multi-modal data acquisition system for collecting and processing additional modes, including multiple interferometric, fluorescence and scattering channels.

34 Claims, 47 Drawing Sheets
(32 of 47 Drawing Sheet(s) Filed in Color)

U.S. PATENT DOCUMENTS

| | | |
|---|---|---|
| 4,537,861 A | 8/1985 | Elings et al. |
| 4,741,620 A | 5/1988 | Wickramasinghe |
| 4,876,208 A | 10/1989 | Gustafson et al. |
| 4,899,195 A | 2/1990 | Gotoh |
| 4,975,237 A | 12/1990 | Watling |
| RE33,581 E | 4/1991 | Nicoli et al. |
| 5,122,284 A | 6/1992 | Braynin et al. |
| 5,155,549 A | 10/1992 | Dhadwal |
| 5,413,939 A | 5/1995 | Gustafson et al. |
| 5,478,527 A | 12/1995 | Gustafson et al. |
| 5,478,750 A | 12/1995 | Bernstein et al. |
| 5,494,829 A | 2/1996 | Sandstrom et al. |
| 5,497,007 A | 3/1996 | Uritsky et al. |
| 5,545,531 A | 8/1996 | Rava et al. |
| 5,581,345 A | 12/1996 | Oki et al. |
| 5,602,377 A | 2/1997 | Beller et al. |
| 5,621,532 A | 4/1997 | Ooki et al. |
| 5,629,044 A | 5/1997 | Rubenchik |
| 5,631,171 A | 5/1997 | Sandstrom et al. |
| 5,653,939 A | 8/1997 | Hollis et al. |
| 5,700,046 A | 12/1997 | Van Doren et al. |
| 5,717,778 A | 2/1998 | Chu et al. |
| 5,736,257 A | 4/1998 | Conrad et al. |
| 5,781,649 A | 7/1998 | Brezoczky |
| 5,786,226 A | 7/1998 | Bocker et al. |
| 5,837,475 A | 11/1998 | Dorsel et al. |
| 5,843,767 A | 12/1998 | Beattie |
| 5,844,871 A | 12/1998 | Maezawa |
| 5,874,219 A | 2/1999 | Rava et al. |
| 5,875,029 A | 2/1999 | Jann et al. |
| 5,883,717 A | 3/1999 | DiMarzio et al. |
| 5,892,577 A | 4/1999 | Gordon |
| 5,900,935 A | 5/1999 | Klein et al. |
| 5,922,617 A | 7/1999 | Wang et al. |
| 5,935,785 A | 8/1999 | Reber et al. |
| 5,945,334 A | 8/1999 | Besemer et al. |
| 5,955,377 A | 9/1999 | Maul et al. |
| 5,968,728 A | 10/1999 | Perttunen et al. |
| 5,999,262 A | 12/1999 | Dobschal et al. |
| 6,008,892 A | 12/1999 | Kain et al. |
| 6,030,581 A | 2/2000 | Virtanen |
| 6,048,692 A | 4/2000 | Maracas et al. |
| 6,060,237 A | 5/2000 | Nygren et al. |
| 6,071,748 A | 6/2000 | Modlin et al. |
| 6,099,803 A | 8/2000 | Ackley |
| 6,110,748 A | 8/2000 | Reber et al. |
| 6,121,048 A | 9/2000 | Zaffaroni et al. |
| 6,140,044 A | 10/2000 | Besemer et al. |
| 6,143,247 A | 11/2000 | Sheppard |
| 6,177,990 B1 | 1/2001 | Kain et al. |
| 6,221,579 B1 | 4/2001 | Everhart et al. |
| 6,238,869 B1 | 5/2001 | Kris et al. |
| 6,248,539 B1 | 6/2001 | Ghadiri et al. |
| 6,249,593 B1 | 6/2001 | Chu et al. |
| 6,256,088 B1 | 7/2001 | Gordon |
| 6,271,924 B1 | 8/2001 | Ngoi et al. |
| 6,287,783 B1 | 9/2001 | Maynard et al. |
| 6,287,850 B1 | 9/2001 | Besemer et al. |
| 6,312,901 B2 | 11/2001 | Virtanen |
| 6,312,961 B1 | 11/2001 | Voirin et al. |
| 6,319,468 B1 | 11/2001 | Sheppard, Jr. et al. |
| 6,319,469 B1 | 11/2001 | Mian et al. |
| 6,320,665 B1 | 11/2001 | Ngoi et al. |
| 6,327,031 B1 | 12/2001 | Gordon |
| 6,339,473 B1 | 1/2002 | Gordon |
| 6,342,349 B1 | 1/2002 | Virtanen |
| 6,342,395 B1 | 1/2002 | Hammock et al. |
| 6,345,115 B1 | 2/2002 | Ramm et al. |
| 6,350,413 B1 | 2/2002 | Reichert et al. |
| 6,355,429 B1 | 3/2002 | Nygren et al. |
| 6,368,795 B1 | 4/2002 | Hefti |
| 6,376,258 B2 | 4/2002 | Hefti |
| 6,381,025 B1 | 4/2002 | Bornhop et al. |
| 6,387,331 B1 | 5/2002 | Hunter |
| 6,395,558 B1 | 5/2002 | Duveneck et al. |
| 6,395,562 B1 | 5/2002 | Hammock et al. |
| 6,399,365 B2 | 6/2002 | Besemer et al. |
| 6,403,957 B1 | 6/2002 | Fodor et al. |
| 6,416,642 B1 | 7/2002 | Alajoki et al. |
| 6,469,787 B1 | 10/2002 | Meyer et al. |
| 6,476,907 B1 | 11/2002 | Gordon |
| 6,483,585 B1 | 11/2002 | Yang |
| 6,483,588 B1 | 11/2002 | Graefe et al. |
| 6,496,267 B1 * | 12/2002 | Takaoka ...................... 356/497 |
| 6,496,309 B1 | 12/2002 | Bliton et al. |
| 6,518,056 B2 | 2/2003 | Schembri et al. |
| 6,540,618 B1 | 4/2003 | Morath et al. |
| 6,551,817 B2 | 4/2003 | Besemer et al. |
| 6,566,069 B2 | 5/2003 | Virtanen |
| 6,584,217 B1 | 6/2003 | Lawless et al. |
| 6,591,196 B1 | 7/2003 | Yakhini et al. |
| 6,596,483 B1 | 7/2003 | Choong et al. |
| 6,602,702 B1 | 8/2003 | McDevitt et al. |
| 6,623,696 B1 | 9/2003 | Kim et al. |
| 6,624,896 B1 | 9/2003 | Neal et al. |
| 6,649,403 B1 | 11/2003 | McDevitt |
| 6,653,152 B2 | 11/2003 | Challener |
| 6,656,428 B1 | 12/2003 | Clark et al. |
| 6,685,885 B2 | 2/2004 | Nolte et al. |
| 6,687,008 B1 | 2/2004 | Peale et al. |
| 6,709,869 B2 | 3/2004 | Mian et al. |
| 6,720,177 B2 | 4/2004 | Ghadiri et al. |
| 6,733,977 B2 | 5/2004 | Besemer et al. |
| 6,734,000 B2 | 5/2004 | Bhatia |
| 6,737,238 B2 | 5/2004 | Suzuki |
| 6,743,633 B1 | 6/2004 | Hunter |
| 6,760,298 B2 | 7/2004 | Worthington et al. |
| 6,766,817 B2 | 7/2004 | da Silva |
| 6,770,447 B2 | 8/2004 | Maynard et al. |
| 6,783,938 B2 | 8/2004 | Nygren et al. |
| 6,787,110 B2 | 9/2004 | Tiefenthaler |
| 6,791,677 B2 | 9/2004 | Kawai et al. |
| 6,803,999 B1 | 10/2004 | Gordon |
| 6,806,963 B1 | 10/2004 | Walti et al. |
| 6,819,432 B2 | 11/2004 | Pepper et al. |
| 6,836,338 B2 | 12/2004 | Opsal et al. |
| 6,844,965 B1 | 1/2005 | Engelhardt |
| 6,847,452 B2 | 1/2005 | Hill |
| 6,878,555 B2 | 4/2005 | Andersson et al. |
| 6,897,965 B2 | 5/2005 | Ghadiri et al. |
| 6,917,421 B1 | 7/2005 | Wihl et al. |
| 6,917,432 B2 | 7/2005 | Hill et al. |
| 6,918,404 B2 | 7/2005 | da Silva |
| 6,937,323 B2 | 8/2005 | Worthington et al. |
| 6,955,878 B2 | 10/2005 | Kambara et al. |
| 6,958,131 B2 | 10/2005 | Tiefenthaler |
| 6,980,299 B1 | 12/2005 | de Boer |
| 6,980,677 B2 | 12/2005 | Niles et al. |
| 6,987,569 B2 | 1/2006 | Hill |
| 6,990,221 B2 | 1/2006 | Shams |
| 6,992,769 B2 | 1/2006 | Gordon |
| 6,995,845 B2 | 2/2006 | Worthington |
| 7,006,927 B2 | 2/2006 | Yakhini et al. |
| 7,008,794 B2 | 3/2006 | Goh et al. |
| 7,012,249 B2 | 3/2006 | Krutchinsky et al. |
| 7,014,815 B1 | 3/2006 | Worthington et al. |
| 7,026,131 B2 | 4/2006 | Hurt et al. |
| 7,027,163 B2 | 4/2006 | Angeley |
| 7,031,508 B2 | 4/2006 | Lawless et al. |
| 7,033,747 B2 | 4/2006 | Gordon |
| 7,042,570 B2 | 5/2006 | Sailor et al. |
| 7,061,594 B2 | 6/2006 | Worthington et al. |
| 7,066,586 B2 | 6/2006 | da Silva |
| 7,070,987 B2 | 7/2006 | Cunningham et al. |
| 7,077,996 B2 | 7/2006 | Randall et al. |
| 7,083,920 B2 | 8/2006 | Werner et al. |
| 7,087,203 B2 | 8/2006 | Gordon et al. |
| 7,088,650 B1 | 8/2006 | Worthington et al. |
| 7,091,034 B2 | 8/2006 | Virtanen |
| 7,091,049 B2 | 8/2006 | Boga et al. |
| 7,094,595 B2 | 8/2006 | Cunningham et al. |
| 7,094,609 B2 | 8/2006 | Demers |
| 7,098,041 B2 | 8/2006 | Kaylor et al. |
| 7,102,752 B2 | 9/2006 | Kaylor et al. |
| 7,106,513 B2 | 9/2006 | Moon et al. |
| 7,110,094 B2 | 9/2006 | Gordon |
| 7,110,345 B2 | 9/2006 | Worthington et al. |

| | | |
|---|---|---|
| 7,118,855 B2 | 10/2006 | Cohen et al. |
| 7,141,378 B2 | 11/2006 | Miller et al. |
| 7,141,416 B2 | 11/2006 | Krutzik |
| 7,145,645 B2 | 12/2006 | Blumenfeld et al. |
| 7,148,970 B2 | 12/2006 | de Boer |
| 7,200,088 B2 | 4/2007 | Worthington et al. |
| 7,221,632 B2 | 5/2007 | Worthington et al. |
| 7,312,046 B2 | 12/2007 | Chin |
| 7,318,903 B2 | 1/2008 | Link |
| 7,659,968 B2 * | 2/2010 | Wang et al. ............... 356/73 |
| 2001/0055812 A1 | 12/2001 | Mian et al. |
| 2002/0001546 A1 | 1/2002 | Hunter et al. |
| 2002/0008871 A1 | 1/2002 | Poustka et al. |
| 2002/0045276 A1 | 4/2002 | Yguerabide et al. |
| 2002/0051973 A1 | 5/2002 | Delenstarr et al. |
| 2002/0058242 A1 | 5/2002 | Demers |
| 2002/0085202 A1 | 7/2002 | Gordon |
| 2002/0097658 A1 | 7/2002 | Worthington et al. |
| 2002/0106661 A1 | 8/2002 | Virtanen et al. |
| 2002/0127565 A1 | 9/2002 | Cunningham et al. |
| 2002/0135754 A1 | 9/2002 | Gordon |
| 2002/0151043 A1 | 10/2002 | Gordon |
| 2002/0192664 A1 | 12/2002 | Nygren et al. |
| 2003/0026735 A1 | 2/2003 | Nolte et al. |
| 2003/0035352 A1 | 2/2003 | Worthington |
| 2003/0054376 A1 | 3/2003 | Mullis et al. |
| 2003/0112446 A1 | 6/2003 | Miller et al. |
| 2003/0133640 A1 | 7/2003 | Tiefenthaler |
| 2003/0134330 A1 | 7/2003 | Ravkin et al. |
| 2004/0002085 A1 | 1/2004 | Schembri et al. |
| 2004/0078337 A1 | 4/2004 | King et al. |
| 2004/0106130 A1 | 6/2004 | Besemer et al. |
| 2004/0132172 A1 | 7/2004 | Cunningham et al. |
| 2004/0150829 A1 | 8/2004 | Koch et al. |
| 2004/0155309 A1 | 8/2004 | Sorin |
| 2004/0166525 A1 | 8/2004 | Besemer et al. |
| 2004/0166593 A1 | 8/2004 | Nolte et al. |
| 2004/0223881 A1 | 11/2004 | Cunningham et al. |
| 2004/0229254 A1 | 11/2004 | Clair |
| 2004/0247486 A1 | 12/2004 | Tiefenthaler |
| 2004/0258927 A1 | 12/2004 | Conzone et al. |
| 2005/0002827 A1 | 1/2005 | McIntyre et al. |
| 2005/0003459 A1 | 1/2005 | Krutzik |
| 2005/0019901 A1 | 1/2005 | Matveeva et al. |
| 2005/0042628 A1 | 2/2005 | Rava et al. |
| 2005/0084422 A1 | 4/2005 | Kido et al. |
| 2005/0084895 A1 | 4/2005 | Besemer et al. |
| 2005/0106746 A1 | 5/2005 | Shinn et al. |
| 2005/0123907 A1 | 6/2005 | Rava et al. |
| 2005/0131745 A1 | 6/2005 | Keller et al. |
| 2005/0158819 A1 | 7/2005 | Besemer et al. |
| 2005/0176058 A1 | 8/2005 | Zaffaroni et al. |
| 2005/0191630 A1 | 9/2005 | Besemer et al. |
| 2005/0214950 A1 | 9/2005 | Roeder et al. |
| 2005/0226769 A1 | 10/2005 | Shiga |
| 2005/0248754 A1 | 11/2005 | Wang et al. |
| 2005/0254062 A1 | 11/2005 | Tan et al. |
| 2005/0259260 A1 | 11/2005 | Wakita |
| 2006/0040380 A1 | 2/2006 | Besemer et al. |
| 2006/0078935 A1 | 4/2006 | Werner et al. |
| 2006/0204399 A1 | 9/2006 | Freeman et al. |
| 2006/0210449 A1 | 9/2006 | Zoval et al. |
| 2006/0223172 A1 | 10/2006 | Bedingham et al. |
| 2006/0234267 A1 | 10/2006 | Besemer et al. |
| 2006/0256350 A1 | 11/2006 | Nolte et al. |
| 2006/0256676 A1 | 11/2006 | Nolte et al. |
| 2006/0257939 A1 | 11/2006 | Demers |
| 2006/0269450 A1 | 11/2006 | Kim et al. |
| 2006/0270064 A1 | 11/2006 | Gordon et al. |
| 2007/0003436 A1 | 1/2007 | Nolte et al. |
| 2007/0003925 A1 | 1/2007 | Nolte et al. |
| 2007/0003979 A1 | 1/2007 | Worthington |
| 2007/0023643 A1 | 2/2007 | Nolte et al. |
| 2007/0070848 A1 | 3/2007 | Worthington et al. |
| 2007/0077599 A1 | 4/2007 | Krutzik |
| 2007/0077605 A1 | 4/2007 | Hurt et al. |
| 2007/0108465 A1 | 5/2007 | Pacholski et al. |

FOREIGN PATENT DOCUMENTS

| | | |
|---|---|---|
| EP | 1424549 | 6/2004 |
| WO | WO 9104489 | 4/1991 |
| WO | WO 9104491 | 4/1991 |
| WO | WO 9113353 | 9/1991 |
| WO | WO 9214136 | 8/1992 |
| WO | WO 9403774 | 2/1994 |
| WO | WO 9837238 | 2/1998 |
| WO | WO 0000265 | 1/2000 |
| WO | WO 0039584 | 7/2000 |
| WO | WO 0111310 | 2/2001 |
| WO | WO 0144441 | 6/2001 |
| WO | WO 06042746 | 4/2006 |
| WO | WO 2006/075797 A1 * | 7/2006 |

OTHER PUBLICATIONS

S. Balassubramanian, L.Lahiri, Y. Ding, M.R. Melloch, And D.D. Nolte, Two-Wave Mixing Dynamics and Nonlinear Hot-Electron Transport In Transverse-Geometry Photorefractive Quantum Wells Studies by Moving Grantings, Appl. Phys. B. 68, pp. 863-9 (1990).

Bietsch, A. And B. Michel, Conformal Contact and Pattern Stability of Stamps Used For Soft Lithography, J. Appl. Phys., 2000, vol. 88, pp. 4310-4318.

Brecht, A. And Gauglitz, G., Recent Developments in Optical Transducers for Chemical or Biochemical Applications. Sensors and Actuators B, 1997 vol. 38-39, pp. 1-7.

E. Delmarche, A. Bernard, II. Schmid, B. Michel, and H. Biebuyck, Patterned Delivery of Immunoglobulins to Surface Using Microfluidic Networks, Science 276,779-781(1997).

E. Delamarche, A. Bernard, Schmid, B., Bietsch, Michel, and H. Biebuyck, Microfluidic Networks For Chemical Patterning of Substrates: Design and Application to Bioassays, Journal of the American Chemical Society 120, pp. 500-508 (1998).

A. Blouin et al., Detection of Ultrasonic Motion of a Scattering Surface by Two-Wave Mixing In a Photorefractive GaAs Crystal, Appl. Phys. Lett. 65, pp. 932-934 (1994).

P. Delaye, A. Blouin, D. Drolet, L.A. Montmorrillong, A. Roosen, and J.P. Monchal1n, Detection of Ultrasonic Motion of a Scattering Surface by Photorefractive InP:Fe Under An Applied dc Field, J. Opt. Soc. Am. B14, pp. 1723-34 (1997).

Ding, Y. et al., Femtosecond Pulse Shaping By Dynamic Holograms In Photorefractive Multiple Quantum Wells, Optical Society of America, Optics Letters, vol. 22, pp. 718-720, 1997.

Ding, Y. et al., Adaptive All-Order Dispersion Compensation Of Ultrafast Laser Pulses Using Dynamic Spectral Holography, American Institute of Physics, Applied Physics Letters, vol. 77, pp. 3255-3257, 1999.

DuBendorfer, J. and Kunz, R. E., Reference Pads For Miniature Integrated Optical Sensors. Sensors and Actuators B, 1997, vol. 38-39, pp. 116-121.

Effenhauser, C.S., et al., Integrated Capillary Electrophoresis On Flexible Silicone Microdevices: Analysis of DNA Restriction Fragments And Detection Of Single DNA Molecules On Microchips. Anal. Chem., 1997, vol. 69, pp. 3451-3457.

Ekins, R., F. Chu and E. Biggart, Development of Microspot Multi-Analyte Ratiometric Immunoassay Using Dual Flourescent-Labelled Antibodies. Anal. Chim. Acta, 1989, vol. 227, pp. 73-96.

Ekins R et al. Multianalyte Microspot Immunoassay, The Microanalytical Compact Disk Of The Future: Clin. Chem., 1991, Vo. 37(11), p. 1955-1967.

Ekins, R., Ligand Assays, From Electrophoresis to Miniaturized Microarrays, Clin. Chem. 1998, vol. 44(9), pp. 2015-2030.

Fattinger, C., Koller, H., Schlatter, D., Wehrli, P., 1993, The Difference Interferometer-A High Sensitive Optical Probe For Quantification Of Molecular-Surface Concentration, Biosens, Bioelectron 8, pp. 99-107.

Gao, H., et al., Immunosensing With Photo-Immobilized Immunoreagents On Planar Optical Wave Guides. Biosensors and Bioelectronics, 1995, vol. 10, pp. 317-328.

Geissler. M. et al., Microcontact Printing Chemical Patterns With Flat Stamps, J. Am. Chem. Soc., 2000, vol. 122, pp. 6303-6304.

Gruska, B. et al., Fast and Reliable Thickness and Refractive Index Measurement of Antireflection Coatings on Solar-Silicon by Ellipsometry, Sentech Instruments GmbH, CarlOScheele-Str. 16, 12489 Berlin Germany, Sep. 2006.

Grzybowski, B.A., et al., Generation of Micrometer-Sized Patterns For Microanalytical Applications Using a Laser Direct-Write Method and Microcontact Printing, Anal. Chem., 1998, vol. 70, pp. 4645- 4652.

Hagman, M., Doing Immunology On A Chip, Science. 2000, vol. 290, pp. 82-83.

He, B. and F.E. Regnier, Fabrication of Nanocolumns for Liquid Chromatography, Anal. Chem., 1998, vol. 70, pp. 3790-3797.

Hecht, E., Optics, 1987, Addison-Wesely Publishing Co., Inc., Menlo Park, CA, pp. 281-286.

Hu, J. et al., Using Soft Lithography to Fabricate GaAs/AlGaAs Heterostructure Field Effect Transistors. Appl. Phys. Lett., 1997 vol. 71, pp. 2020-2022.

Ing R.K. And Monchalin, LP., Broadband Optical Detection of Ultrasound By Two-Wave Mixing In A Photorefractive Crystal, Appl. Phys. Lett. 59, 3233-5 (1991).

Jenison, R., Yan, S. Haeberli, A. Polisky, B., 2001, Interference-Based Detection of Nucleic Acid Targets on Optically Coated Silicon. Nat. Biotechnol. 19, pp. 62-65.

Jenison, Robert et al. Silicon-based Biosensors for Rapid Detection of Protein or Nucleic Acid Targets, Clinical Chemistry, 47:10, 2001 pp. 1894-1990.

Jones, R. et al., Adaptive Femtosecond Optical Pulse Combining, American Institute of Physics, pp. 3692-3694, 2000.

Kapur, Ravi et al. Streamlining the Drug Discovery Process by Integrating Miniaturization High Throughput Screening, High Content Screening, and Automation on the CeliChip TM System. Biomedical Microdevices, vol. 3, No. 2, 1999, pp. 99-109.

Kricka, L.J., Miniaturization of Analytical Systems. Clin. Chem., 1998, vol. 44(9), pp. 2008- 2014.

Kunz, R. E., Miniature Integrated Optical Modules For Chemical and Biochemical Sensing. Sensors and Actuators B, 1997, vol. 38-39, pp, 13-28.

Kwolek, K.M. et al., Photorefractive Asymmetric Fabry-Perot Quantum Wells: Transverse-field Geometry, Appl. Phys. Lett. vol. 67, pp. 736-738, 1995.

La Clair, J. et al., Molecular Screening On A Compact Disc, The Royal Society of Chemistry, Org. Biomol. Chem., vol. 1, pp. 3244-3249, 2003.

Lahiri, I. et al., Photorefractive p-i-n. Diode Quantum Well Spatial Light Modulators, American Institute of Physics, Applied Physics Letters, vol. 67, pp. 1408-1410, 1995.

I. Lahiri, L.J. Pyrak, Nolte, D.D. Nolte, M.R Melloch, Ra. Kruger, G.O. Backer, and M. B. Klein, Laser-Based Ultrasound Detection Using Photrefractive Uantum Wells, Appl. Phys. Lett. 73, pp. 104-143 (1998).

Maisenholder., B., et al. A GaAs/lGaAs-based Refractometer Platform For Integrated Optical Sensing Applications, Sensors and Actuators S, 1997, vol. 38-39, pp. 324-329.

Martin, B.D., et al., Direct Protein Microarray Fabrication Using a Hydrogel Stamper, Langmuir, 1998, vol. 14, pp. 3971-3975.

Marx, J., DNA Arrays Reveal Cancer In Its Many Forms, Science, 2000, vol. 289, pp. 1670- 1672.

Montmorillon, La Biaggio, I Delaye, P, Launay, J.C., and Roosen, A, Eye Safe Large Field of View Homodyne Detection Using a Photorefractive CdTe:V Crystal. Opt. Commun. 29, pp. 293 (1996).

Morhard, F. et al., Immobilization Of Antibodies in Micropatterns For Cell Detection By Optical Diffraction, Sensors and Actuators B, 2000, vol. 70, pp. 232-242.

Nolte, D.D., Semi-Insulating Semiconductor Heterostructures: Optoelectronic Properties and Applications, Appl. Phys. vol. 85, pp. 6259-6289, 1999.

Nolte, D. D. et al., Adaptive Beam Combining and Interferomety Using Photorefractive Quantum Wells, J. Opt. Soc. Am. B, vol. 19, No. 2, Feb. 2001, pp. 195-205.

Nolte, D.D. et al., Spinning-Disk Interferometry The BioCD, Optics & Photonics News, pp. 48-53, 2004.

Nolte, D. D., Self-Adaptive Optical Holography In Quantum Wells, pp. 1-6, 2005.

Nolte, D., et al., Photorefractive Quantum Wells, 2005.

Peng, Leilei et al., Adaptive Optical Biocompact Disk For Molecular Recognition, Applied Physics Letters 86, pp. 183902-1 - 183902-3, 2005.

Pompe, T., et al., Submicron Contact Printing On Silicon Using Stamp Pads, Langmuir, 1999, vol. 15, pp. 2398-2401.

Pouet. S.F., Ing. R.K., Krishnaswanry S. and Royer D. Heterodyne Interferometer With Two-Wave Mixing In Photo refractive Crystals For Ultrasound Detection On Rough Surface, Appl. Phys. Lett. 69. pp. 3782 (1996).

Regnier, F.E., et al. Chromatography and Electrophoresis On Chips: Critical Elements Of Future Integrated, Microfluidic Analytical Systems For Life Science. Tibtech, 1999, vol. 17, pp. 101-106.

I. Rossomakhin and Stepanov, Linear Adaptive Interferometers Via Diffusion Recording In Cubic Photorefractive Crystals, Opt. Commun. 86, pp. 199-204 (1991).

Sanders, G.H.W. and A. Manz, Chip-based Microsystems For Genomic and Proteomic Analysis, Trends in Anal, Chem., 2000, vol. 19(6), pp. 364-378.

Scruby, C.B. and L.E. Drain, Laser Ultrasonics: Techniques and Applications. 1990, Bristol: Adam Hilger., pp. 116-123.

Varma, M.M, et al., Spinning-Disk Self-Referencing Interferometry of Antigen-Antibody Recognition, Optics Letters, vol. 29. pp. 950-952, 2004.

Wang, J., Survey and Summary From DNA Biosensors To Gene Chips. Nucl. Acids Res., 2000 vol. 28 (16), pp. 3011-3016.

See, C.W. et al., Scanning Differential Optical Profilometer For Simultaneous Measurement Of Amplitude and Phase Variation, Appl. Phys. Lett, vol. 53, No. 1, pp. 10-12, 1988.

Somekh, Michael et al., Scanning Heterodyne Confocal Differential Phase And Intensity Microscope, Applied Optics, vol. 34, No. 22, pp. 4857-4868, 1995.

Burkhart, et al. UCSD Scientists Develop Novel Way to Screen Molecules Using Conventional CDS an Compact Disk Players; UCSD newsletter; pp. 1-4, 2003.

Xia, Y., et al. Non Photolithographic Methods and Fabrication of Elastomeric Stamps for Use in Microcontact Printing, Langmuir, 1996, Vo. 12, pp. 4033-4038.

Suddendorf Manfred, et al., Single-Probe-Beam Differential Amplitude and PhaseScanning Interferometer, Applied Optics, vol. 36, No. 25, pp. 6202-6210, 1997.

Varma, M.M. et al.: High-Speed Label-Free Multi-Analyte Detection Through MicroInterferometry, Proc. of SPIE, vol. 4966, pp. 58-64. 2003.

Varma, M.M., et al., High Speed Label Free Detection By Spinning-Disk Micro-Interferometry, Biosensors & Bioelectronics, vol. 19, pp. 1371-1376, 2004.

St. John et al., Diffraction-Based Cell Detection Using a Microcontact Printed Antibody Grating, Analytical Chemistry, 1998, vol. 70, No. 6, pp. 1108-1111.

Musundi et al, "Approaching Real-Time Molecular Diagnostics: Single-Pair Fluorescence Resonance Energy Transfer (spFRET) Detection for the Analysis of Low Abundant Point Mutations in K-ras Oncogenes," J Am Chem Soc. Jun. 11, 2003;125(23):6937-45.

Lovgren J, Valtonen-Andre C, Marsal K, et al: Measurement of prostate-specific antigen and human glandular kallikrein 2 in different body fluids. J. Androl. 20:348-355, 1999.

J. Homola, "Present and future of surface plasmon resonance biosensors," Analytical and Bioanalytical Chemistry, vol. 377, pp. 528-539, 2003.

Nolte, David D. (2007), "Molecular Interferometry", http://www.nanohub.org/resources/2832/, Jun. 26, 2007 (67 pages).

Michele Ceccarelli, Giuliano Antoniol: A Deformable Grid-Matching Approach for Microarray Images. IEEE Transactions on Image Processing 15(10): 3178-3188 (2006).

Peter Bajcsy: Gridline: automatic grid alignment DNA microarray scans. IEEE Transactions on Image Processing 13(1): 15-25 (2004).

Luis Rueda, Vidya Vidyadharan: A Hill-Climbing Approach for Automatic Gridding of cDNA Microarray Images. IEEE/ACM Trans. Comput. Biology Bioinform. 3(1): 72-83 (2006).

Nagarajan, R., Intensity-based segmentation of microarrays images. IEEE Trans. Med. Imaging. v22. 882-889 (2003).

Faramarzpour, N., Shirani, S. and Bondy, J., Lossless DNA microarray image compression. IEEE Conf. Signal Systems Comput. v2. 1501-1504 (2003).

Katzer, M., Kummert, F. And Sagerer, G., Methods for automatic microarray image segmentation. IEEE Trans. NanoBiosci. v2 i4. 202-214 (2003).

N. Brandle, H. Bischof, H. Lapp: "*Robust DNA Microarray Image Analysis*"; Machine Vision and Applications, 15 (2003), 1; 11-28.

Nagarajan, R and Peterson, C.A. [2002] Identifying Spots in Microarray Images IEEE Trans. Nanobioscience, 1(2), 78-84.

Konstantinos Blekas, Nikolas P. Galatsanos, Aristidis Likas, Isaac E. Lagaris: Mixture model analysis of DNA microarray images. IEEE Trans. Med. Imaging 24(7): 901-909 (2005).

Jinn Ho, Wen-Liang Hwang, Henry Horn-Shing Lu, and D. T. Lee, 'Gridding Spot Centers of Smoothly Distorted Microarray Images', IEEE Trans. on Image Processing, vol. 15, No. 2, Feb. 2006.

Fabri, R: "Towards non-parametric gidding of Microarray images," Digital Signal Processing, 2002. DSP 2002. 2002 14th International Conference publication, vol. 2, pp. 623-626.

H. Vikalo, B. Hassibi, and A. Hassibi, "A statistical model for microarrays, optimal estimation algorithms, and limits of performance," IEEE Transactions on Signal Processing, Special Issue on Genomics Signal Processing, vol. 54, No. 6, Jun. 2006, pp. 2444-2455.

Chiao-Ling Shih, Hung-Wen Chiu, "Automatic spot detection of cDNA Microarray images using mathematical morphology methods," Conference on IEEE EMBS Asian-Pacific, Oct. 2003, pp. 70-71.

Macbeath, G. and S.L. Schreiber. 2000. "Printing proteins as microarrays for high-throughput function determination." Science 289:1760-1763.

Guemouri, L., J. Ogier, and J. J. Ramsden, "Optical properties of protein monolayers during assembly." Journal of Chemical Physics 1998. 109:3265-3268.

Ostroff, R., A. Ettinger, H. La, M. Rihanek, L. Zalman, J. Meador III, A. K. Patick, S. Worland, and B. Polisky. 2001. "Rapid multiserotype detection of human rhinoviruses on optically coated silicon surfaces." J. Clin. Virol. 21: 105-117.

H. Ozen and S. Sozen, "PSA Isoforms in prostate cancer detection," *Eur. Urol. Suppl.*, vol. 5, pp. 495-499, 2006.

N. B. Sheller, S. Petrash, M.D. Foster, "Atomic Force Microscopy and X-ray Reflectivity Studies of Albumin Adsorbed onto Self-Assembled Monolayers of Hexadecyltrichlorosilane," *Langmuir*, 14, 4535-4544, 1998.

M. Varma, D. D. Nolte, H. D. Inerowicz, and F. E. Regnier, "Multi-Analyte Array Micro-Diffraction Interferometry," in *Microarrays: Design, Fabrication and Reading* vol. 4626, B. J. B. e. al., Ed.: SPIE, 2002, pp. 69-77.

D. D. Nolte and M. R. Melloch, "Photorefractive Quantum Wells and Thin Films," in *Photorefractive Effects and Materials*, D. D. Nolte, Ed. Dordrecht: Kluwer Academic Publishers, pp. 373-451, 1995.

D. S. Gerber, R. Droopad, and G. N. Maracas, "A GaAs/AlGaAs Asymmetric FabryPerot Reflection Modulator with very High Contrast Ratio," *IEEE Phot. Tech Lett.*, vol. 5, pp. 55-58, 1993.

M. Whitehead and G. Parry, "High-contrast reflection modulation at normal incidence in asymmetric multiple quantum well Fabry-Perot structure," *Electron. Lett.*, vol. 25, pp. 566-568, 1989.

B. J. Luff, J. S. Wilkinson, J. Piehler, U. Hollenbach, J. Ingenhoff, and N. Fabricius, "Integrated optical Mach-Zehnder biosensor," *Journal of Lightwave Technology*, vol. 16, pp. 583-592, 1998.

B. Drapp, J. Piehler, A. Brecht, G. Gauglitz, B. J. Luff, J. S. Wilkinson, and J. Ingenhoff, "Integrated.optical Mach-Zehnder interferometers as simazine immunoprobes," *Sensors and Actuators B-Chemical*, vol. 39, pp. 277-282, 1997.

L. U. Kempen and R. E. Kunz, "Replicated Mach-Zehnder interferometers with focusing grating couplers for sensing applications," *Sensors and Actuators B-Chemical*, vol. 39, pp. 295-299, 1997.

V. S.-Y. Lin, K. Motesharei, K.-P. S. Dancil, M. Sailor, and M. R. Ghadiri, "A porous silicon-based optical interferometric biosensor," *Science*, vol. 278, pp. 840-843, 1997.

Y. C. Cao, R. Jin, and C. A. Mirkin, "Nanoparticles with Raman Spectroscopic Fingerprints for DNA and RNA Detection," *Science*, vol. 297, pp. 1536-1540, 2002.

T. A. Taton, C. A. Mirkin, and R. L. Letsinger, "Scanometric DNA Array Detection with Nanoparticle Probes," *Science*, vol. 289, pp. 1757-1760, 2000.

C. Gurtner, E. Tu, N. Jamshidi, R. W. Haigis, T. J. Onofrey, C. F. Edman, R. Sosnowski, B. Wallace, and M. J. Beller, "Microelectronic array devices and techniques for electric field enhanced DNA hybridization in low-conductance buffers," *Electrophoresis*, vol. 23, pp. 1543-1550, 2002.

Y. Joon Mo, J. Bell, H. Ping, M. Tirado, D. Thomas, A. H. Forster, R. W. Haigis, P. D. Swanson, R. B. Wallace, B. Martinsons, and M. Krihak, "An integrated, stacked microlaboratory for biological agent detection with DNA and immunoassays," *Biosensors & Bioelectronics*, vol. 17, pp. 605-618, 2002.

M. J. Heller, "An active microelectronics device for multiplex DNA analysis," *IEEE Engineering in Medicine & Biology Magazine*, vol. 15, pp. 100-104, 1996.

D. D. Nolte and K. M. Kwolek, "Diffraction from a Short-Cavity Fabry-Perot: Applications to Photorefractive Quantum Wells," *Opt. Commun.*, vol. 115, pp. 606-616, 1995.

R.-H. Yan, R. J. Simes, and L. A. Coldren, "Analysis and design of surface-normal FabryPerot electrooptic modulators," *IEEE Quant. Electron.*, vol. 25, pp. 2272-2280, 1989.

J. F. Heffernan, M. H. Moloney, J. Hegarty, J. S. Roberts, and M. Whitehead, "All optical high contrast absorptive modulation in an asymmetric Fabry-Perot etalon," *Appl. Phys. Lett.*, vol. 58, pp. 2877-2879, 1991.

A. Larsson and J. Maserjian, "Optically addressed asymmetric Fabry-Perot modulator," Appl. Phys. Lett., vol. 59, pp. 3099-3101, 1991.

K. M. Kwolek, M. R. Melloch, and D. D. Nolte, "Dynamic holography in a reflection/transmission photorefractive quantum-well asymmetric Fabry-Perot," *Appl. Phys. Lett.*, vol. 65, pp. 385-387, 1994.

D. D. Nolte, "Dynamic Holographic Phase Gratings in Multiple Quantum Well Asymmetric Reflection Fabry-Perot Modulators," *Opt. Lett.*, vol. 19, pp. 819-821, 1994.

S. P. Balk, Y.-J. Ko, and G. J. Bubley, "Biology of Prostate-specific antigen," J. Clin. Onc., vol. 21, pp. 383-391, 2003.

Wang, M.C., Papsidero, L.D., Kuriyama, M., Valenzuela, G.P. And Chu, T.M. 1981. Prostate antigen: A new potential marker for prostatic cancer. *The Prostate* 2: 89-96.

T. Cass and F. S. Ligler, "Immobilized Biomolecules in Analysis: A Practical Approach," Oxford: Oxford, 1998.

R. Guersen, I. Lahiri, M. R. Melloch, J. M. Woodall and D. D Nolte, Transient Enhanced Intermixing of Arsenic-Rich Nonstoichiometric AlAs/GaAs Quantum Wells, Phys. Rev. B60,10926-10934 (1999).

D. Crouse, D. D. Nolte, J. C. P. Chang, and M. R. Melloch, "Optical absorption by Ag precipitates in AlGaAs," *J. Appl. Phys.*, vol. 81, pp. 7981-7987, 1997.

G. A. Sefler, E. Oh, R. S. Rana, I. Miotkowski, A. K. Ramdas, and D. D. Nolte, "Faraday Photorefractive Effect in a Diluted Magnetic Semiconductor," *Opt. Lett.*, vol. 17, pp. 1420-1422, 1992.

J. M. Mckenna, D. D. Nolte, W. Walukiewicz, and P. Becla, "Persistent holographic absorption gratings in AlSb:Se," *Appl. Phys. Lett.*, vol. 68, pp. 735-737, 1996.

R. S. Rana, E. Oh, K. Chua, A. K. Ramdas, and D. D. Nolte, "Voigtphotorefractive two-wave mixing in CdMnTe," *J. Lumin.*, vol. 60 & 61, pp. 56-59, 1994.

L. Peng, P. Yu, D. D. Nolte, and M. R. Melloch, "High-speed adaptive interferometer for optical coherence-domain reflectometry through turbid media," Opt. Lett. 28, 396-398 (2003).

R. M. Brubaker, Y. Ding, D. D. Nolte, M. R. Melloch, and A. M. Weiner, "Bandwidth-Limited Diffraction of Femtosecond Pulses from Photorefractive Quantum Wells," *IEEE J. Quant. Electron.*, vol. 33, pp. 2150-2158, 1997.

Y. Ding, D. D. Nolte, M. R. Melloch, and A. M. Weiner, "Real-time edge enhancement of femtosecond time-domain images by use of photorefractive quantum wells," *Opt. Lett.*, vol. 22, pp. 1101-1103, 1997.

Y. Ding, D. D. Nolte, M. R. Melloch, and A. M. Weiner, "Time-domain image processing using dynamic holography," *IEEE J. Sel. Top. Quant. Elect.*, vol. 4, pp. 332-341, 1998.

M. Dinu, D. D. Nolte, and M. R. Melloch, "Electroabsorption spectroscopy of effectivemass AlGaAs/GaAs Fibonacci superlattices," *Phys. Rev. B*, vol. 56, pp. 1987-1995, 1997.

M. Dinu, K. Nakagawa, M. R. Melloch, A. M. Weiner, and D. D. Nolte, "Broadband Low-Dispersion Diffraction of Femtosecond Pulses from Photorefractive Quantum Wells," *J. Opt. Soc. Am. B*, vol. 17, pp. 1313-1319, 2000.

Y. Ding, D. D. Nolte, Z. Zheng, A. Kanan, A. M. Weiner, and G. A. Brost, "Bandwdith Study of Volume Holography in Photorefrative InP:Fe at 1.5 microns for Frequency Domain Femtosecond Pulse Processing," *J. Opt. Soc. B*, vol. 15, pp. 2763-68, 1998.

Y. Ding, I. Lahiri, D. D. Nolte, G. J. Dunning, and D. M. Pepper, "Electric Field Correlation of Femtosecond Pulses Using a Photo-Electromotive Force Detector," *J. Opt. Soc. Am. B*, vol. 15, pp. 2013-17, 1998.

R. Jones, N. P. Barry, S. C. W. Hyde, P. M. W. French, K. M. Kwolek, D. D. Nolte, and M. R. Melloch, "Direct-to-Video holographic readout in quantum wells for 3-D imaging through turbid media," *Opt. Lett.*, vol. 23, pp. 103-105, 1998.

R. Jones, M. Tziraki, P. M. W. French, K. M. Kwolek, D. D. Nolte, and M. R. Melloch, "Direct-to-video holographic 3-D imaging using photorefractive multiple quantum well devices," *Optics Express*, vol. 2, pp. 439-448, 1998.

M. Tziraki, R. Jones, P. M. W. French, M. R. Melloch, and D. D. Nolte, "Photorefractive Holography for Imaging through turbid media using low coherence light," *Appl. Phys. B*, vol. 70, pp. 151-154, 1999.

M. Tziraki, R. Jones, P. French, D. Nolte, and M. Melloch, "Short-coherence photorefractive holography in multiple-quantum-well devices using light-emitting diodes," *Appl. Phys. Lett.*, vol. 75, pp. 363-5, 1999.

I. Lahiri, D. D. Nolte, M. R. Melloch, and M. B. Klein, "Oscillatory mode coupling and electrically strobed gratings in photorefractive quantum-well diodes," *Optics Lett.*, vol. 23, pp. 49-51, 1998.

I. Lahiri, L. J. Pyrak-Nolte, D. D. Nolte, and M. R. Melloch, "Transient Dynamics During Two-Wave Mixing in Photorefractive Quantum Well Diodes using Moving Gratings," *Opt. Express*, vol. 2, pp. 432-438, 1998.

C.-C. Wang, R. A. Linke, D. D. Nolte, M. R. Melloch, and S. Trivedi, "Enhanced detection bandwidth for optical doppler frequency measurements using moving space charge field effects in GaAs multiple quantum wells," *Appl. Phys. Lett.*, vol. 70, pp. 2034-2036, 1997.

C. Wang, R. A. Linke, D. D. Nolte, M. R. Melloch, and S. Trivedi, "Signal strength enhancement and bandwidth tuning in moving space charge field photodetectors using alternating bias field," *Appl. Phys. Lett.*, vol. 72, pp. 100-102, 1998.

D. M. Pepper, G. J. Dunning, M. P. Chiao, T. R. O'Meara, P. V. Mitchell, I. Lahiri, and D. D. Nolte, "Characterization of the photo-EMF response for laser-based ultrasonic sensing under simulated industrial conditions," *Rev. Prog. Quant. Nondestruct. Eval.*, vol. 17, pp. 627-634, 1998.

D. D. Nolte, Mesoscopic Pointlike Defects in Semiconductors: Deep-level Energies, Phys. Rev. B 58, 7994-8001 (1998).

M. Dinu, I. Miotkowski and D. D. Nolte, Magnetic Quenching of Time-Reversed Light in Photorefractive Diluted Magnetic Semiconductors, Phys. Rev. B 58, 10435 (1998).

S. Balasubramanian, S. W. Mansour, M. R. Melloch and D. D. Nolte, Vacancy diffusion Kinetics in arsenic-rich nonstoichiometric AlAs/GaAs heterostructures, Phys. Rev. B 63, 033305-1—033305-3 (2000).

David D. Nolte, Manoj M. Varma, Leilei Peng, Halina D. Inerowicz, Fred E. Regnier, Spinning-disk laser interferometers for immunoassays and proteomics: the BioCD in Proc. SPIE vol. 5328 Microarrays and Combinatorial Techniques: Design, Fabrication, and Analysis II; Dan V. Nicolau, Ramesh Raghavachari; Eds., p. 41-48 (2004).

Manoj M. Varma, Halina D. Inerowicz, Fred E. Regnier, David D. Nolte, Real-time spinning disk interferometric immunoassays, in Proc. SPIE vol. 5328, Microarrays and Combinatorial Techniques: Design, Fabrication, and Analysis II; Dan V. Nicolau, Ramesh Raghavachari; Eds., p. 62-68, 2004.

T. Jensen, L Kelly, A. Lazarides, and G. C. Schatz, "Electrodynamics of noble metal nanoparticles and nanoparticle clusters," Journal of Cluster Science, vol. 10, pp. 295-317, 1999.

H. Kuwata, H. Tamaru, K. Esumi, and K. Miyano, "Resonant light scattering from metal nanoparticles: Practical analysis beyond Rayleigh approximation," Applied Physics Letters, vol. 83, pp. 4625-4627, 2003.

M.J. Jory, P. S. Cann, J. R. Sambles, and E. A. Perkins, "Surface-plasmon-enhanced light scattering from microscopic spheres," *Applied Physics Letters*, vol. 83, pp. 3006-3008, 2003.

K.L. Kelly, E. Coronado, L L Zhao, and G. C. Schatz, "The optical properties of metal nanoparticles: The influence of size, shape, and dielectric environment," *Journal of Physical Chemistry B*, vol. 107, pp. 668-677, 2003.

P. Chakraborty, "Metal nanoclusters in glasses as non-linear photonic materials,"*Journal of Materials Science*, vol. 33, pp. 2235-2249, 1998.

S.J. Oldenburg, S. L. Westcott, R. D. Averitt, and N. J. Halas, "Surface enhanced Raman scattering in the near infrared using metal nanoshell substrates," *Journal of Chemical Physics*, vol. 111, pp. 4729-4735, 1999.

P. Mulvaney, "Surface plasmon spectroscopy of nanosized metal particles," *Langmuir*, vol. 12, pp. 788-800, 1996.

H.F. Ghaemi, T. Thio, D. E. Grupp, T. W. Ebbesen, and H. J. Lezec, "Surface plasmons enhance optical transmission through subwavelength holes," *Physical Review B*, vol. 58, pp. 6779- 6782, 1998.

T.W. Ebbesen, H. J. Lezec, H. F. Ghaemi, T. Thio, and P. A. Wolff, "Extraordinary optical transmission through sub-wavelength hole arrays," *Nature*, vol. 391, pp. 667-669, 1998.

D.A. Genov, A. K. Sarychev, V. M. Shalaev, and A. Wei, "Resonant field enhancements from metal nanoparticle arrays," *Nano Letters*, vol. 4, pp. 153-158, 2004.

V. Koubova, E. Brynda, L. Karasova, J. Skvor, J. Homola, J. Dostalek, P. Tobiska, and J. Rosicky, "Detection of foodborne pathogens using surface plasmon resonance biosensors," Sensors and Actuators B-Chemical, vol. 74, pp. 100-105, 2001.

M. Minunni and M. Mascini, "Detection of Pesticide in Drinking-Water Using Real-Time Biospecific Interaction Analysis (Bia),"*Analytical Letters*, vol. 26, pp. 1441-1460, 1993.

C. Mouvet, R. D. Harris, C. Maciag, B. J. Luff, J. S. Wilkinson, J. Piehler, A. Brecht, G. Gauglitz, R. Abuknesha, and G. Ismail, "Determination of simazine in water samples by waveguide surface plasmon resonance," Analytica Chimica Acta, vol. 338, pp. 109-117, 1997.

A. Rasooly, "Surface plasmon resonance analysis of staphylococcal enterotoxin B in food," *Journal of Food Protection*, vol. 64, pp. 37-43, 2001.

G. Sakai, K. Ogata, T. Uda, N. Miura, and N. Yamazoe, "A surface plasmon resonancebased immunosensor for highly sensitive detection of morphine," Sensors and Actuators B-Chemical, vol. 49, pp. 5-12, 1998.

G. Sakai, S. Nakata, T. Uda, N. Miura, and N. Yamazoe, "Highly selective and sensitive SPR immunosensor for detection of methamphetamine," Electrochimica Acta, vol. 44, pp. 3849-3854, 1999.

E. Kretschmann and H. Raether, "Radiative Decay of Non Radiative Surface Plasmons Excited by Light," *Zeitschrift Fur Naturforschung Part a-Astrophysik Physik Und Physikalische Chemie*, vol. A 23, pp. 2135-2136, 1968.

A. Otto, "Excitation of Nonradiative Surface Plasma Waves in Silver by Method of Frustrated Total Reflection," *Zeitschrift Fur Physik*, vol. 216, pp. 398-410, 1968.

J. Homola, S. S. Yee, and G. Gauglitz, "Surface plasmon resonance sensors: review," Sensors and Actuators B-Chemical, vol. 54, pp. 3-15, 1999.

M. Malmqvist, "Biacore: an affinity biosensor system for characterization of biomolecular interactions," *Biochemical Society Transactions*, vol. 27, 1999.

M. Fivash, E. M. Towler, and R. J. Fisher, "BIAcore for macromolecular interaction," Current Opinion in Biotechnology, vol. 9, pp. 97-101, 1998.

L. D. Roden and D. G. Myszka, "Global analysis of a macromolecular interaction measured on BIAcore," Biochemical and Biophysical Research Communications, vol. 225, pp. 1073-1077, 1996.

C. F. R. Mateus, M. C. Y. Huang, B. T. Cunningham, and C. J. Chang-Hasnaln, "Compact label-free biosensor using VCSEL-based measurement system," IEEE Photonics Technology Letters, vol. 16, pp. 1712-1714, 2004.

P. Y. Li, L. Bo, J. Gerstenmaier, and B. T. Cunningham, "A new method for label-free imaging of biomolecular interactions," Sensors and Actuators B-Chemical, vol. 99, pp. 6-13, 2004.

G. Walter, K. Bussow, A. Lueking, and J. Glokler, "High-throughput protein arrays: prospects for molecular diagnostics," Trends in Molecular Medicine, vol. 8, pp. 250-253, 2002.

J.B. Pendry, L. Martin-Moreno, and F. J. Garcia-Vidal, "Mimicking surface plasmons with structured surfaces," Science, vol. 305, pp. 847-848, 2004.

A.G. Brolo, R. Gordon, B. Leathem, and K. L. Kavanagh, "Surface plasmon sensor based on the enhanced light transmission through arrays of nanoholes in gold films," Langmuir, vol. 20, pp. 4813-4815, 2004.

J. A. Coy, D. D. Nolte, G. J. Dunning, D. M. Pepper, B. Pouet, G. D. Bacher, and M. B. Klein, "Asymmetric Interdigitated MSM Contacts for Improved Adaptive Photo-EMF Detectors," J. Opt. Soc. Am. B, vol. 17, pp. 697-704, 1999.

J. Coy, F. Stedt, I. Lahiri, M. Melloch, and D. Nolte, "Exciton electroabsorption moments and sum rules," Opt. Commun., vol. 176, pp. 17-29, 2000.

R. S. Rana, E. Oh, K. Chua, A. K. Ramdas, and D. D. Nolte, "Magneto-photorefractive effects in a diluted magnetic semiconductor," *Phys. Rev. B*, vol. 49, pp. 7941-7951, 1994.

D. D. Nolte, I. Lahiri, J. Mckenna, F. R. Steldt, J. C. P. Chang, M. R. Melloch, and J. M. Woodall, "%tinier excitons in a Coulomb Cage," presented at 23rd Int. Conf. Phys. Semicond., Vancouver, Canada, 1994.

D. D. Nolte, J. A. Coy, G. J. Dunning, D. M. Pepper, M. P. Chiao, G. D. Bacher, and M. B. Klein, "Enhanced responsivity of non-steady-state photoinduced electromotive force sensors using asymmetric interdigitated contacts," Opt. Lett., vol. 24, pp. 342-344, 1999.

D. M. Pepper, G. J. Dunning, D. D. Nolte, J. Coy, M. B. Klein, G. D. Backer, and B. Pouet, "Enhanced Responsivity of Photo-Induced-emf Laser Ultrasound Sensors Using Asymmetric Interdigitated Contacts," in Review of Progress in Quantitative Nondestructive Evaluation, vol. 19, D. O. Thompson and D. E. Chimenti, Eds. New York: American Institute of Physics Press, 2000, pp. 2013-2020.

Technology paper entitled "Grating-Coupled Surface Plasmon Resonance (GCSPR)"—printed from HTS Biosystems Technologies website (www.htsbiosystems.com/technology/gcspr.htm) on May 2, 2005.

B. Cunningham, P. Li, and J. Pepper, "Colorimetric resonant reflection as a direct biochemical assay technique," Sensors and Actuators B, vol. 81, pp. 316-328, 2002.

X. Wang, M. Zhao, and D. D. Nolte, "Common-path interferometric detection of protein monolayer on the BioCD," Appl. Opt 46, 7836-7849 (2007).

X. Wang and D. Nolte, " The Bragg Side-Band BioCD," in Conference on Lasers and Electro-Optics/Quantum Electronics and Laser Science Conference and Photonic Applications Systems Technologies, OSA Technical Digest (CD) (Optical Society of America, 2007), 2 pages.

Polizzi, M.A., Plocinik, R.M., and Simpson, G.J., "Ellipsometric Approach for the Real-Time Detection of Label-Free Protein Adsorption by Second Harmonic Generation," J. Am. Chem. Soc., 126, 15, 5001 - 5007, 2004.

Plocinik, R. M.; Simpson, G. J., Polarization characterization in surface second harmonic generation by nonlinear optical null ellipsometry. Analytica Chimica Acta 2003, 496, (1-2), 133-142.

P. B. Luppa, L. J. Sokoll, and D. W. Chan, "Immunosensors—principles and applications to clinical chemistry," *Clinica Chimica Acta*, vol. 314, pp. 1-26, 2001.

C. L. Tucker, J. F. Gera, and P. Uetz, "Towards an understanding of complex protein networks," *Trends in Cell Biology*, vol. 11, pp. 102-106, 2001.

P. Uetz and R. L. Finley, "From protein networks to biological systems," Febs Letters, vol. 579, pp. 1821-1827, 2005.

G. Gauglitz, "Direct optical sensors: principles and selected applications," Analytical and Bioanalytical Chemistry, vol. 381, pp. 141-155, 2005.

M. Zhao, D. D. Nolte, W. R. Cho, F. Regnier, M. Varma, G. Lawrence, and J. Pasqua, "High-speed interferometric detection of label-free immunoassays on the biological compact disc," *I Clin. Chem.*, vol. 52, pp. 2135-2140, 2006.

David D. Nolte and Ming Zhao, "Scaling mass sensitivity of the BioCD at 0.25 pg/mm," Proc. SPIE hit. Soc. Opt. Eng. 6380, 63800J (2006), D01:10.1117/12.686307 (6 pages).

* cited by examiner

High-speed amplifier section (C5460-01)

| Parameter | Symbol | Condition | Min. | Typ. | Max. | Unit |
|---|---|---|---|---|---|---|
| Cut-off frequency | fc | High band, -3 dB | 80 | 100 | - | kHz |
| | | Low band, -3 dB | - | DC | - | - |
| Noise equivalent power | NEP | f = 100 kHz, λ = 800 nm | - | 0.02 | 0.04 | pW/Hz$^{1/2}$ |
| Feedback resistance | - | | - | 10 | - | MΩ |
| Photoelectric sensitivity* | - | APD include, λ = 800 nm, Gain = 30 | -1.4 x 10$^8$ | -1.5 x 10$^8$ | -1.6 x 10$^8$ | V/W |
| Maximum input light level | - | | 0.05 | 0.06 | - | µW |
| Minimum detection limit | - | | - | 0.005 | 0.01 | nW r.m.s. |

FIG. 5

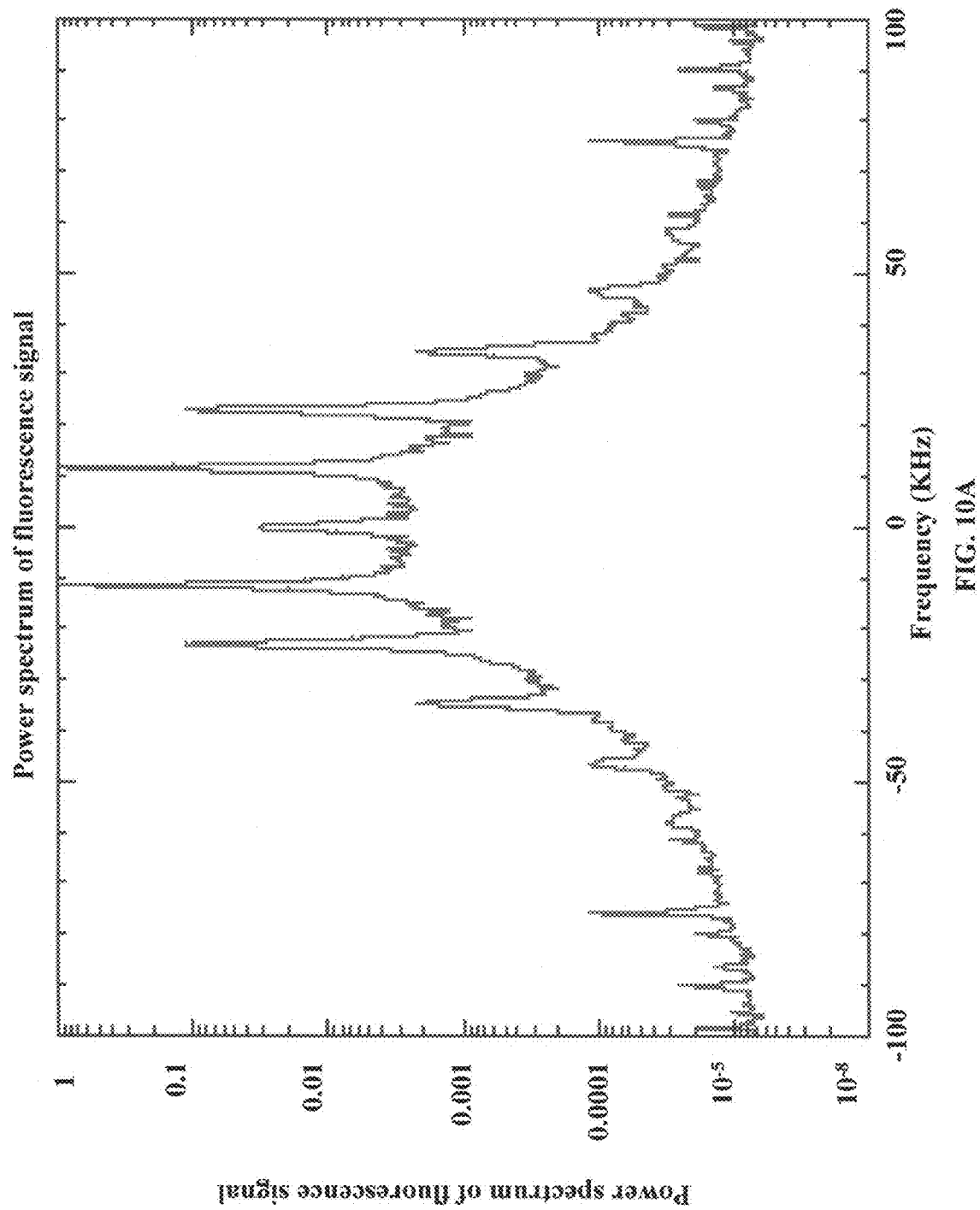

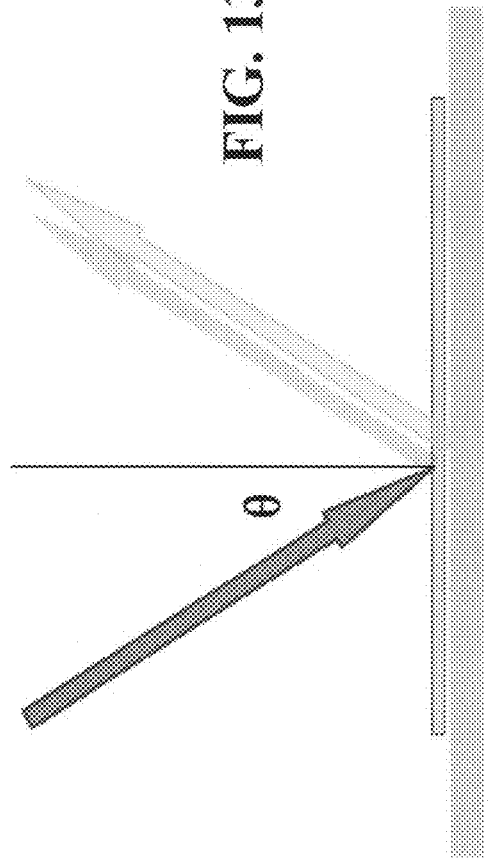
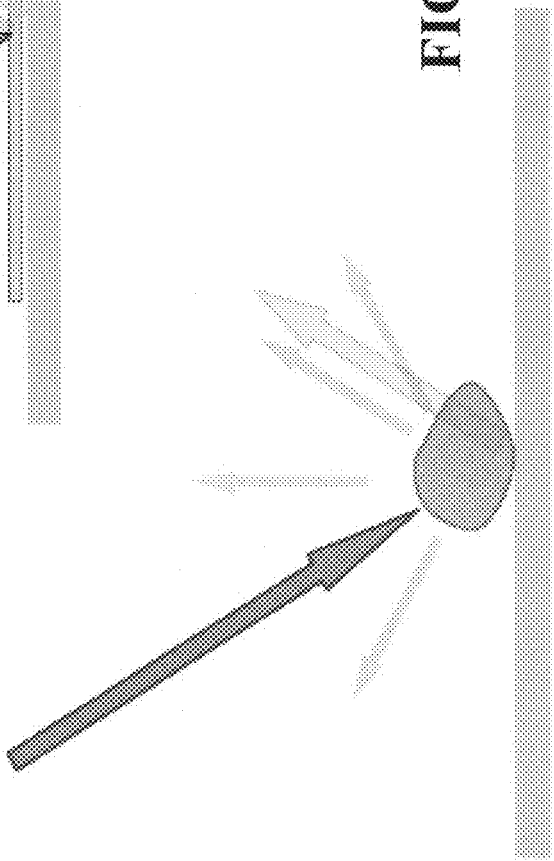
FIG. 13A
FIG. 13B

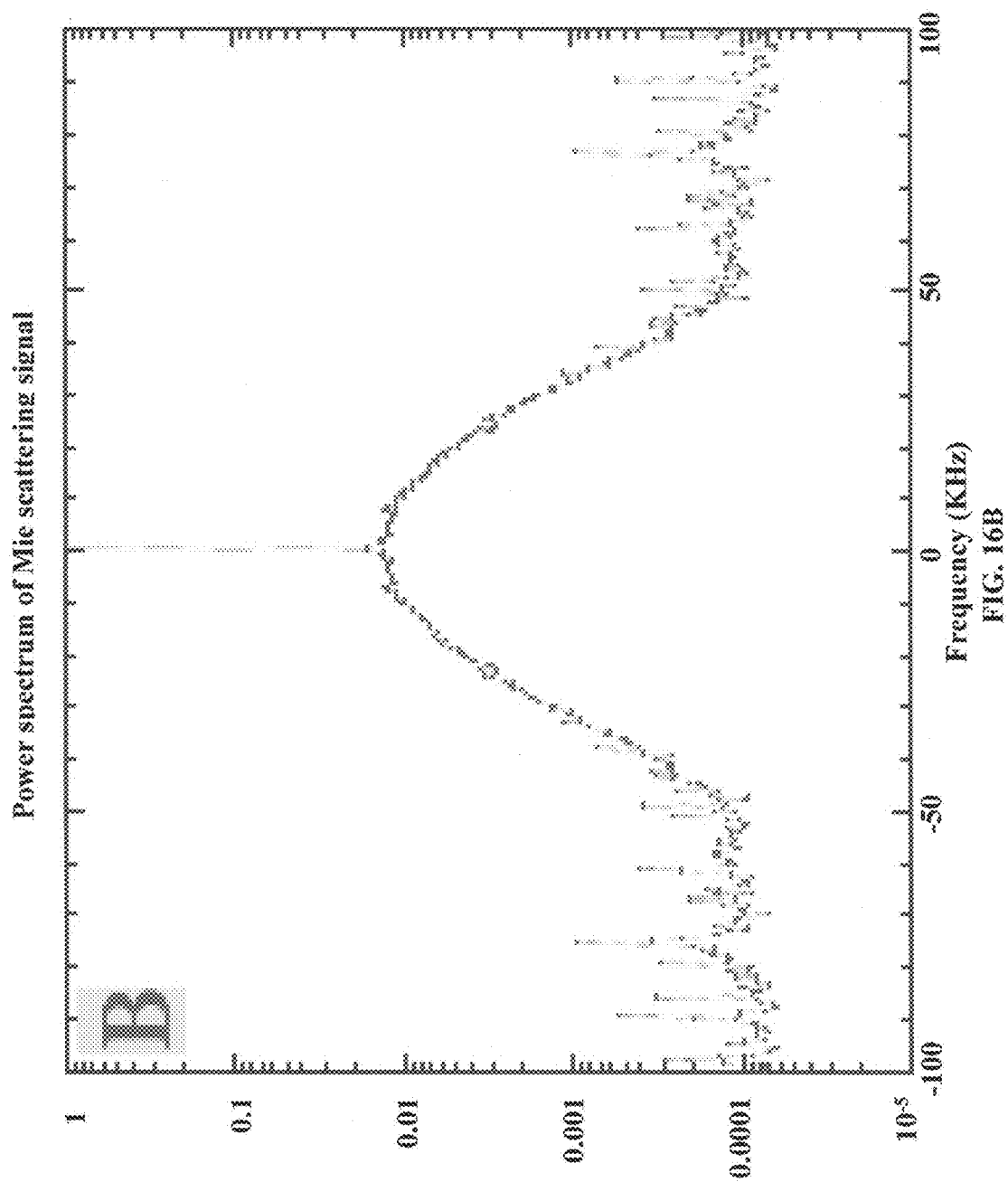

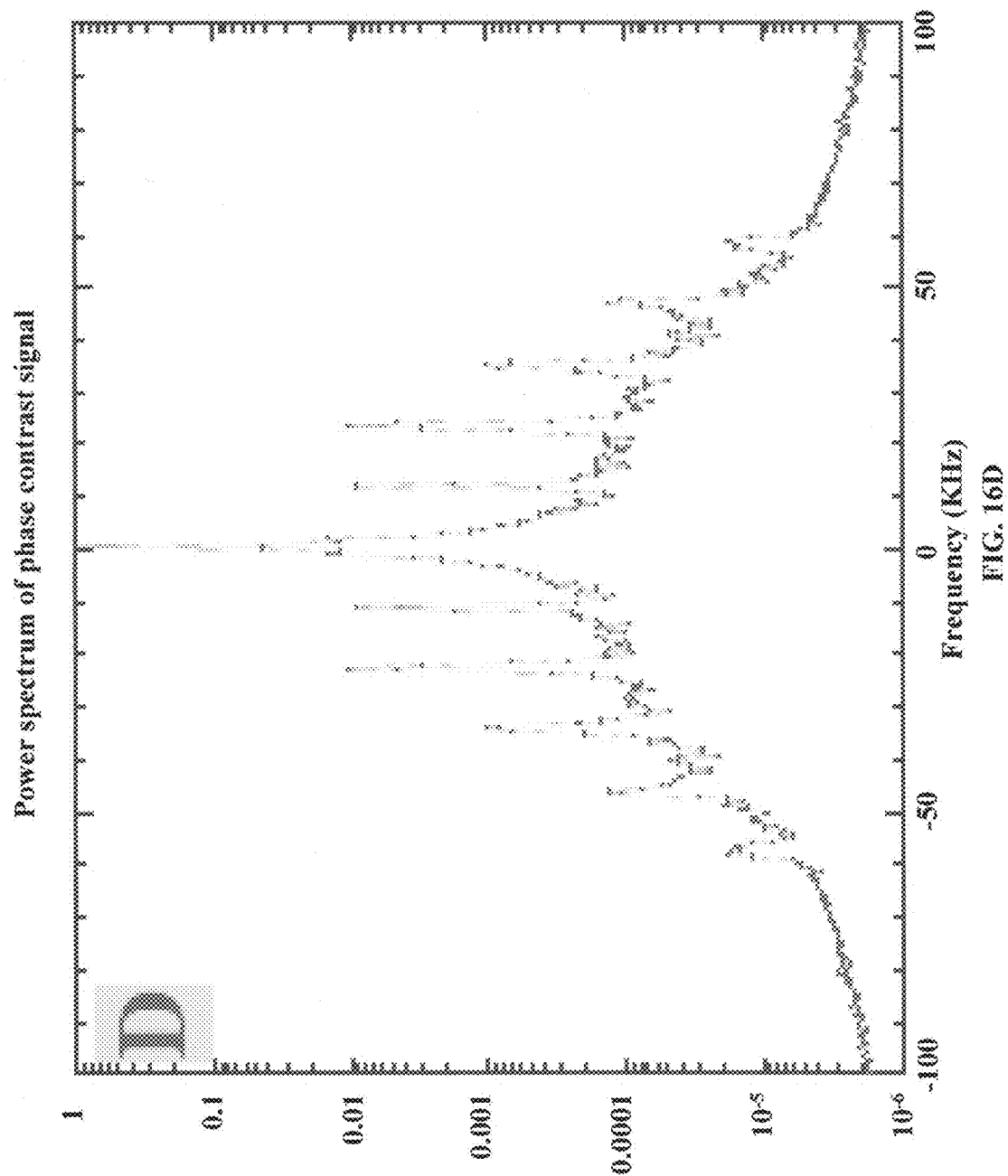

SYSTEM WITH EXTENDED RANGE OF MOLECULAR SENSING THROUGH INTEGRATED MULTI-MODAL DATA ACQUISITION

CROSS-REFERENCE TO RELATED APPLICATIONS

This application is a continuation of U.S. patent application Ser. No. 12/018,108, filed on Jan. 22, 2008, now U.S. Pat. No. 7,659,968 entitled "System with Extended Range of Molecular Sensing Through Integrated Multi-Modal Data Acquisition;" which claims priority to U.S. Provisional Application Ser. No. 60/885,698, filed on Jan. 19, 2007, entitled "Four Channel Optical Detection on Protein-Patterned Biological Compact Disk" and to U.S. Provisional Application Ser. No. 60/916,177, filed on May 4, 2007, entitled "System with Extended Range of Molecular Sensing Through Integrated Multi-Modal Data Acquisition" the disclosures of which are all incorporated herein by this reference.

This application is related to U.S. application Ser. No. 11/675,359, filed on Feb. 15, 2007, entitled "In-Line Quadrature and Anti-Reflection Enhanced Phase Quadrature Interferometric Detection"; U.S. patent application Ser. No. 10/726,772, entitled "Adaptive Interferometric Multi-Analyte High-Speed Biosensor," filed Dec. 3, 2003 (U.S. Pat. Pub. No. 2004/0166593); U.S. Pat. No. 6,685,885, entitled "Bio-Optical Compact Disk System," filed Dec. 17, 2001 and issued Feb. 3, 2004; U.S. patent application Ser. No. 11/345,462 entitled "Method and Apparatus for Phase Contrast Quadrature Interferometric Detection of an Immunoassay," filed Feb. 1, 2006 (U.S. Pat. Pub. No. 2007/0003436); U.S. patent application Ser. No. 11/345,477 entitled "Multiplexed Biological Analyzer Planar Array Apparatus and Methods," filed Feb. 1, 2006 (U.S. Pat. Pub. No. 2007/0003925); U.S. patent application Ser. No. 11/345,564, entitled "Laser Scanning Interferometric Surface Metrology," filed Feb. 1, 2006 (U.S. Pat. Pub. No. 2006/0256350); U.S. patent application Ser. No. 11/345,566, entitled "Differentially Encoded Biological Analyzer Planar Array Apparatus and Methods," filed Feb. 1, 2006 (U.S. Pat. Pub. No. 2007/0023643), the disclosures of which are all incorporated herein by this reference.

BACKGROUND AND SUMMARY OF THE INVENTION

The present invention generally relates to an apparatus capable of simultaneous acquisition of data from multiple molecular sensing modalities, for example and not by way of limitation, a labeled process (such as a fluorescence process) and a label-free process (such as an interferometric process).

Generally, labeled and label-free detection modalities for molecular sensing possess complimentary advantages and drawbacks. For instance, label based sensing systems are not susceptible to background effects as much as label-free systems. Susceptibility to background effects often limits the sensitivity of label-free systems. On the other hand, labeled systems such as fluorescence, which is the most common molecular detection modality in use today, suffer from low photon fluxes which limit their sensitivity, while label-free sensing systems (e.g., the Quadraspec biological compact disc system, such as described in the U.S. Pat. No. 6,685,885) have photon fluxes that are several orders of magnitude higher.

Fluorescence label based systems suffer from additional problems such as photobleaching, which limits the ability to perform time-resolved studies beyond a certain length of time. Label-free systems generally do not suffer from such problems.

Label based systems require an additional chemical processing step of attaching the "label" molecule to the molecule of interest. This process, in addition to increased processing time and cost, can alter the behavior of the molecules of interest. Label-free systems do not require this additional processing step.

In spite of drawbacks such as the ones described above, fluorescent label based detection remains a widely used technology for molecular sensing applications, such as immunosensing and drug discovery, and possesses high sensitivity, especially in the detection of low molecular weight analytes and even single molecule detection.

There are two main reasons for the observed performance of fluorescent label based systems compared to current label-free technologies. First, as mentioned earlier, fluorescent label based systems are not as susceptible to variations in background effects as label-free systems. Susceptibility to background effects can limit the sensitivity of label-free systems. Second, signal transduction in label-free systems is based on some physical property of the molecule of interest, which is often related to its molecular size. Coupled with the background problem, this molecular size dependency restricts the range of molecular size that can be detected reliably with label-free systems. For example, detection of low-molecular weights in immunoassay continues to be a challenge for many label-free systems and they try to get around the molecular size dependency through alternate assay formats such as reverse phase or inhibition assays. While the success of such approaches in circumventing the molecular weight dependency has been demonstrated, these approaches may not always be feasible. Label based systems on the other hand rely only on the properties of the "label" molecule and consequently work independent of the size of the molecule of interest. Thus they work equally well for large as well as small molecules and meet the demand for low molecular weight detection in many application areas.

Even though fluorescent based systems have good performance compared to current label-free systems, the increasing demand for multiplexing is expected to put a significant strain on fluorescent based systems. This is because each molecule of interest requires a unique label. Although some approaches, such as Quantum Dots, have been proposed to address the "unique label" problem, considerable understanding of their interaction with bio-molecules will need to be built for them to emerge as a ubiquitous molecular sensing format. Label-free systems do not suffer from this limitation and as a result are attractive from the multiplexing point of view.

From the items described above, it can be seen that the labeled and label-free molecular detection modalities can provide complimentary performance attributes. However, commercially available molecular sensing platforms do not exploit these complementary properties. Integrating these complementary molecular sensing modalities in a single platform can enhance the capabilities of either mode by providing capability to perform low molecular weight detection with high sensitivity as well as the ability of multiplexing without label limitations for suitable applications.

With this objective in mind, exemplary embodiments of systems incorporating complementary molecular sensing modalities in a single platform are disclosed below. One embodiment integrates fluorescence based detection (most widely used label based detection) and interferometric based detection (most inherently sensitive label-free technology)

into a single instrument. This instrument is capable of simultaneous data acquisition from both channels. The acquired data from both channels can be analyzed, and biologically relevant information, such as the amount of bound protein, can be extracted.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 5 shows specifications for a C5460-01 avalanche photodiode;

FIG. 10A shows the power spectrum corresponding to FIG. 10A;

FIG. 13A illustrates that the reflection change is proportional to the thickness of the protein layer when the protein layer on the surface is thin enough (much less than the probe light wavelength);

FIG. 13B illustrates that if protein molecules agglomerate on the surface, then Mie scattering dominates and the scattering can be detectable in the Mie scattering channel;

FIG. 21a shows a portion of 6,800 spots printed on a region of a biological compact disc of which 3,400 are antibody spots and 3,400 are control spots, each antibody spot being adjacent to a control spot;

FIGS. 21b1-b3 shows scans at different times in the experimental process by the interferometry channel in a simultaneous two-channel scan of interferometry and fluorescence channels: FIG. 21b1 shows a scan of initial thickness, FIG. 21b2 shows a scan after antigen binding; and FIG. 21b3 shows a scan after secondary antibody binding;

FIGS. 21c1-c3 shows scans at different times in the experimental process by the fluorescence channel in a simultaneous two-channel scan of interferometry and fluorescence channels: FIG. 21c1 shows a scan of initial thickness, FIG. 21c2 shows a scan after antigen binding; and FIG. 21c3 shows a scan after secondary antibody binding;

DETAILED DESCRIPTION OF EXEMPLARY EMBODIMENTS

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Fluorescence and interferometric signals have different angular distributions. Fluorescence excitation leads to isotropic (but not homogeneous) incoherent emission of radiation while the interferometric signal comes from coherently scattered radiation in the direction of the reflected light. This difference in angular distribution can be exploited in separating signals from the two channels in the instrument.

Typically, fluorescence wavelength is longer than that of excited light due to energy loss of the excited molecules. The wavelength difference, called the Stokes' s shift, provides another way to separate fluorescence from background light by using optical filters.

Figure 1:
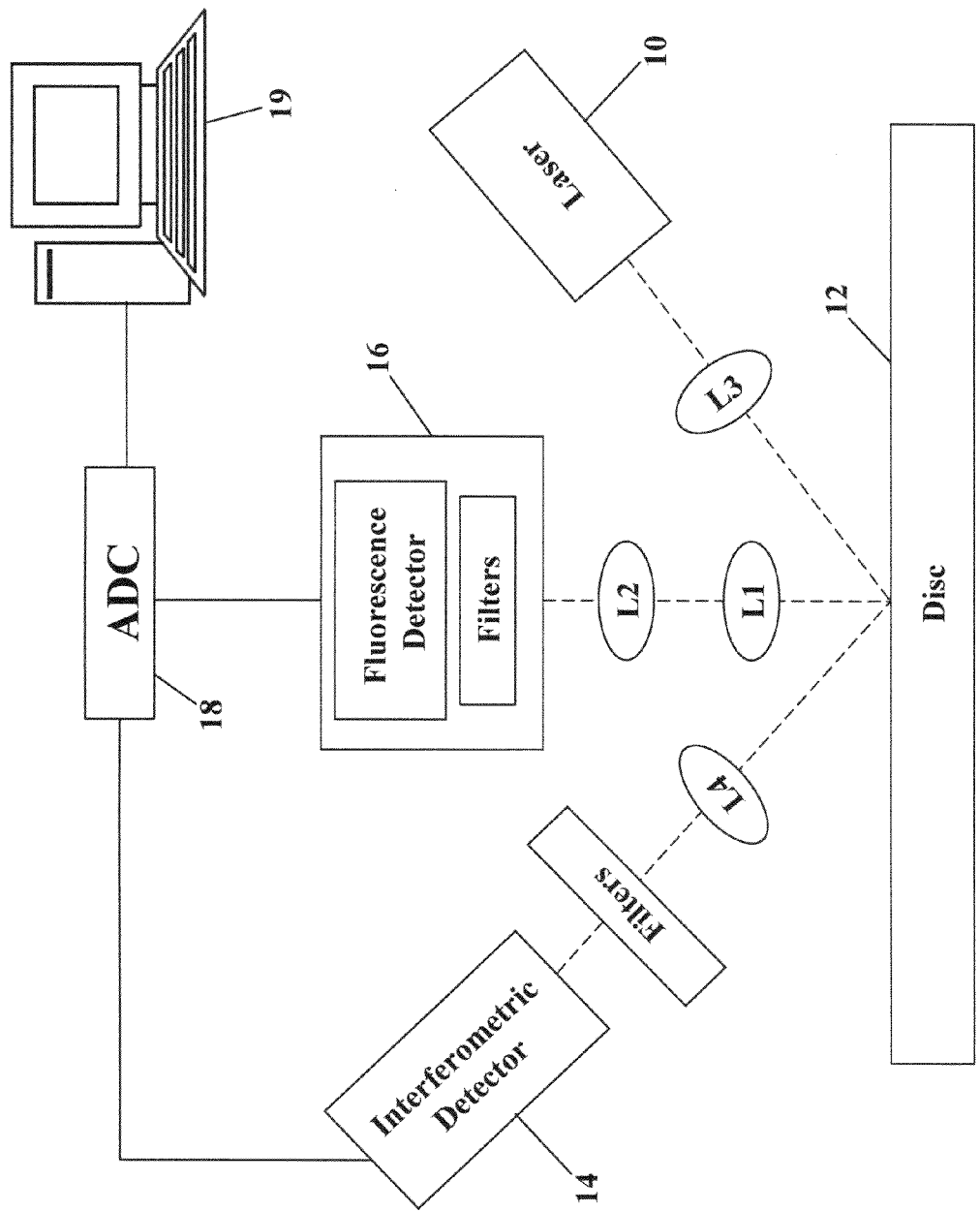
FIG. 1 shows a schematic of an embodiment of a data acquisition system.

An exemplary embodiment of a data collection system that collects both fluorescence and interferometric signals is shown schematically in FIG. 1. The system comprises a laser 10, a linear stage (not shown), a spin motor (not shown) (e.g., Scanner motor from Laser Lines Ltd), a biological compact disc 12, a photodetector 14, an avalanche photodiode detector ("APD") 16, an analog-to-digital converter ("ADC") 18, a computer 19 and optical components such as minors, filters and lens.

The biological compact-disc 12 is mounted on the spin motor capable of spinning at user defined speeds from 20 Hz to 100 Hz in increments of 20 Hz. The optical assembly is fixed to the linear stage which is capable of scanning with a resolution of 0.1 um. The combination of the spinning disc 12 and stage translation creates a polar coordinate system for referencing any point on the disc. Data from a given position of the linear stage constitutes a "track" on the disc 12. Several such "tracks" are acquired with a user defined resolution, typically 20 microns, to build up the disc surface data in both acquisition channels.

In the embodiment illustrated in FIG. 1, the illumination laser light from the laser 10 has a wavelength of 532 nm and serves as the probing light. The incoming laser beam is focused on to the disc using a lens L3, at oblique incidence. The reflected beam containing the interferometric signal is focused on to the photodetector 14 using another lens L4. Filters can be placed in front of the photodetector 14 to eliminate background radiation at wavelengths different from the incident laser wavelength. As mentioned earlier, fluorescence emission is isotropic. A fraction of fluorescence is collected using a high NA lens L1 and is focused onto the APD 16 by a lens L2. Although, in principle, the fluorescence emission can be separated from the probe beam and direct reflection using differences in the angular distribution of fluorescence and interferometric signals, in practice, it is preferable to incorporate filters to eliminate stray scatter, such as from dust or sharp features on the disc, from making its way to the APD 16.

Figure 2:
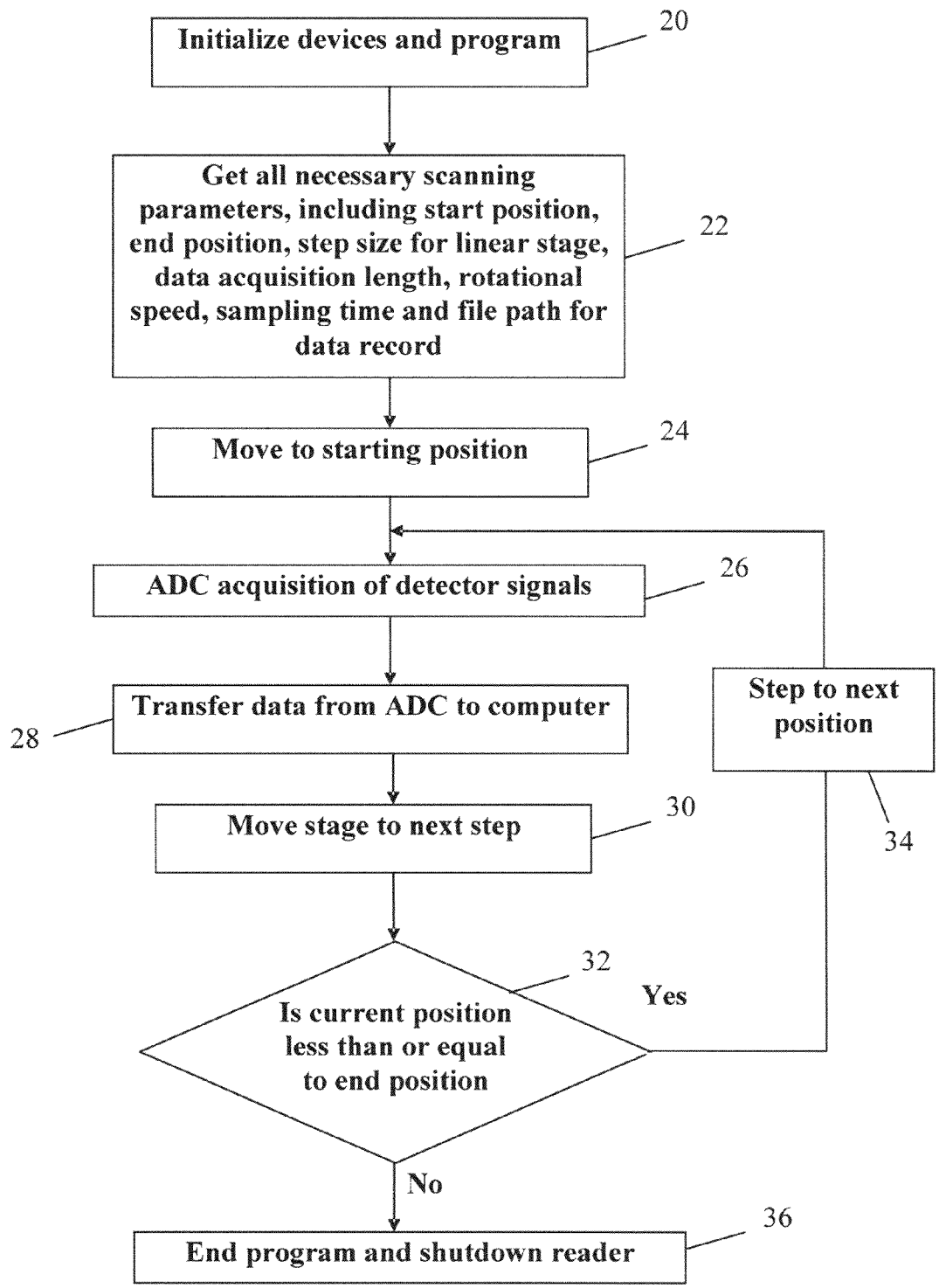
FIG. 2 is a flowchart for an instrument control program that can be used with the embodiment of FIG. 1.

The signals from the APD 16 and the photodetector 14 are sent to a 2 channel ADC 18 for analog-to-digital conversion, after which they are sent to a computer 19. Computerized data acquisition can be done using a system management program. A flowchart for an exemplary system management is shown in FIG. 2.

At step 20, the system devices and program are initialized for a data collection. At step 22, the necessary scanning and data collection parameters are obtained and stored for use in the collection process. At step 24, the system is moved to the starting position for data collection. At step 26, the fluorescence signals from the APD 16 and the interferometric signals from the photodetector 14 are sent to the ADC 18 for analog-to-digital conversion, and, at step 29, the converted signals are sent to the computer 19. At step 30, the stage is used to move the optical assembly to the next step for further data collection. At step 32, the system determines whether the current position of the stage is less than or equal to the end position for data collection. If the current position is less than or equal to the end position, then control is transferred to step 34 which starts data collection at the next position and transfers control to step 26. If the current position is greater than the end position, then control is transferred to step 36 which ends the collection program and shuts down the reader.

The oblique incidence design incorporated in the instrument exploits the differences in the angular distribution of fluorescence and interferometric signals. The oblique design enables the spinning biological compact disc system to possess sufficient photon fluxes without using multiple filters for separation of the fluorescence emission from background light.

Many, commercial fluorescence readers use Photo-Multiplier Tubes (PMTs) for detecting fluorescence emission. PMT's necessitate tight requirements on background shielding, protection from shock and so on. Alternatively, high-gain APDs such as the Hamamatsu C5460-01 can give comparable performance to PMTs but without the problems mentioned earlier. One important design consideration is the bandwidth of the APD which limits the acquisition speed. The high-gain APD 16 used in the embodiment of FIG. 1 has a bandwidth of 100 kHz, which is sufficient to acquire data from a biological compact disc 12 spinning at 4800 rpm.

Sufficient fluorescence emission efficiency is possible over a wide range of substrates. Therefore, the biological compact disc 12 is designed primarily based on the requirements for the label-free systems, which in this case is interferometric. Exemplary biological compact discs of the present embodiment include silicon discs coated with 100 nm of silica film. These discs are useful for commercial applications, particularly as they are inexpensive to manufacture yet still exhibit robustness and good sensitivity for all channels. Such discs are particularly useful for in-line interferometric channel sensitivity applications.

Figure 3A:
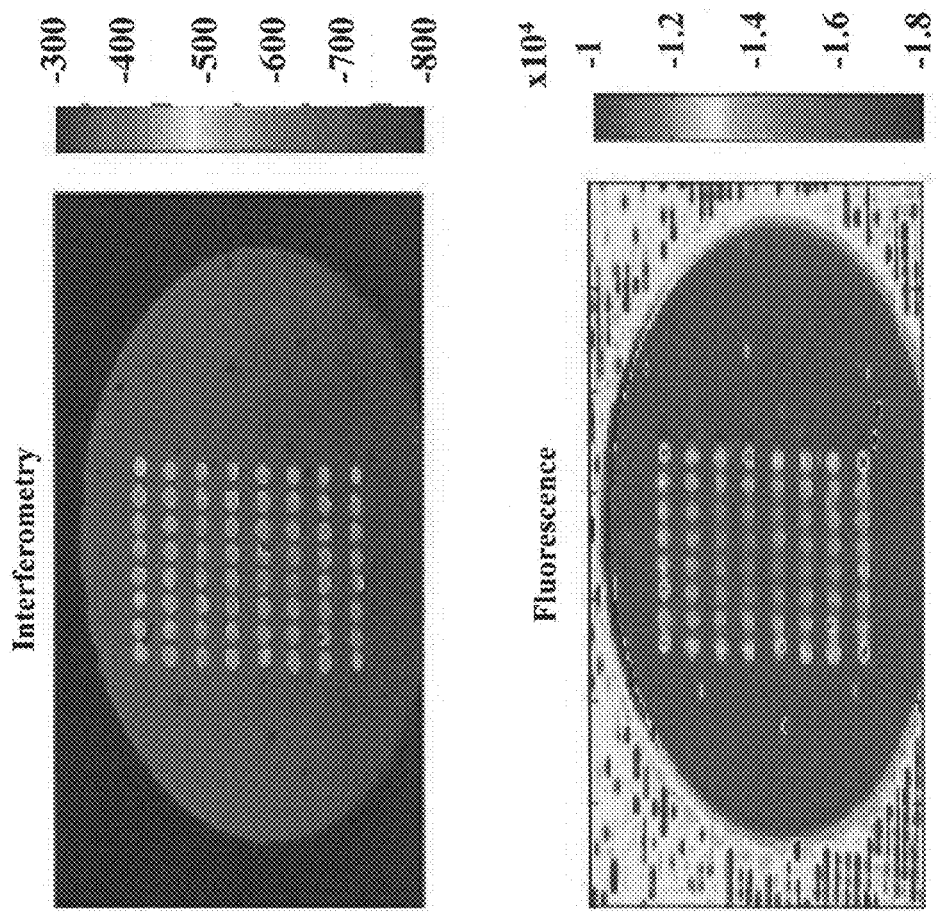
FIG. 3A shows an example of the results of the simultaneous acquisition of fluorescence and interferometric data.
Figure 3B:
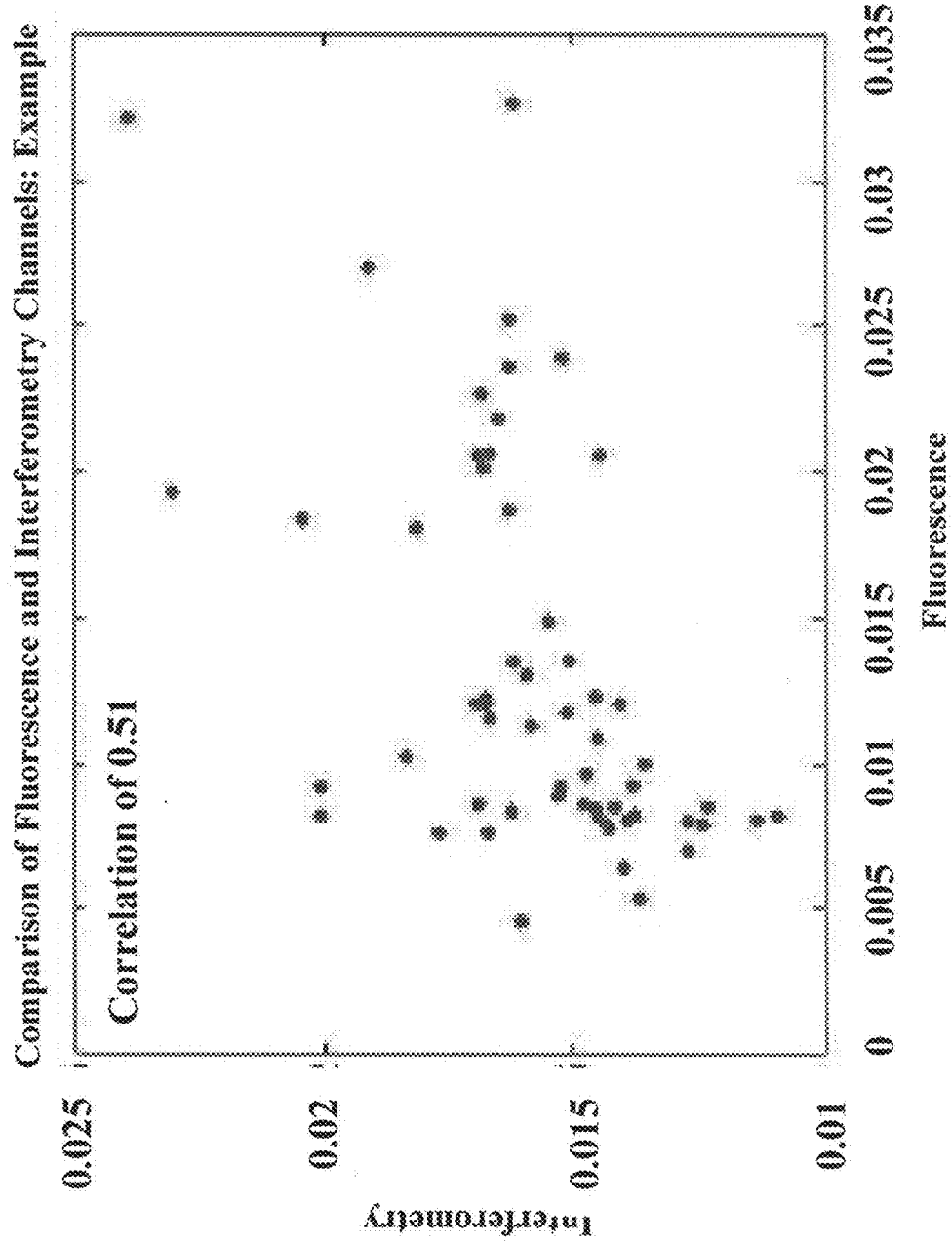
FIG. 3B shows an example of the correlation between fluorescence and interferometric data from fluorescently labeled proteins immobilized on the surface of the biological compact disc.

For the embodiment illustrated in FIG. 1, FIG. 3A shows an example of the readings from the simultaneous acquisition of fluorescence and interferometric data from an exemplary biological compact disc; and FIG. 3B shows an example of the quantitative correlation between the fluorescence and interferometric data. Such correlations can provide valuable information about the various biochemical processes involved in disc processing and molecular detection processes. For instance, in this example, fluorescently labeled antibodies are immobilized on the biological compact disc. The fluorescence channel quantifies the amount of the antibody while the interferometric channel quantifies the sum total of the interactions of all molecules present in the incubating solution, such as buffer, salts and other chemicals. In this case, the degree of correlation, or lack of correlation, between the two channels can tell us about the relative strength of the parasitic process such as binding of foreign molecules on the disc surface. Such information can help in optimizing disc processing steps by eliminating possible parasitic effects. This is a unique capability made possible by the integration of these complementary molecular detection modalities in a single platform.

Figure 4:
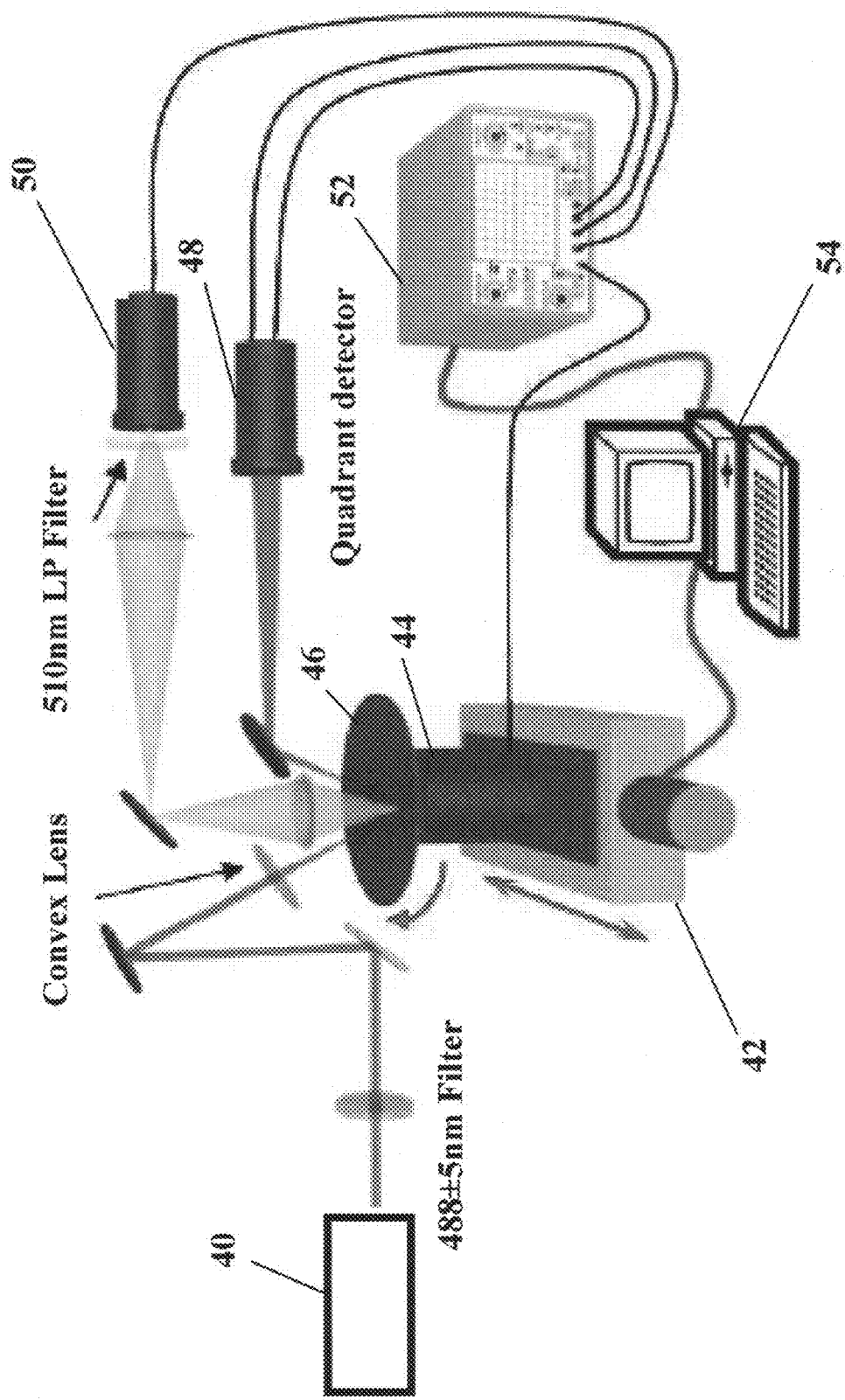
FIG. 4 illustrates an exemplary embodiment of an integrated fluorescence and interferometric microarray detection system.

Another exemplary embodiment of a system for simultaneously acquiring fluorescence and interferometric signals on a substrate, such as a spinning microarray disk is shown in FIG. 4. Although fluorescence and interferometric signals both have scattering effects on probing light beams, their scattering properties have fundamental differences, such as their scattering distributions. With respect to interferometric signals, the scattering is mostly coherent (i.e., each molecule's scattering light is coherent with that of other molecules, and the total scattering light is coherent with incident and reflected light) and specular, in which Rayleigh scattering dominates. When illuminated with a coherent probe light, scattered light from the molecules superposes in the far field. The superposition induces the strongest intensity distribution of the scattering light along the reflected (specular) direction in the far field, and the scattered light interferes with the reflected light. As such, the signal of the target molecules is modulated in the reflected light.

Fluorescence can be treated as incoherent scattered light within the dipole approximation. The incoherence is induced by the random relaxation time and phase of the fluorophore's excited energy level. As such, the fluorescence is incoherent, which means that without coherent superposition, the emitted fluorescence does not form a strong directional distribution, but rather emits into all solid angles. It should be noted that the distribution is also not homogenous and its distribution function can be determined without difficulty. Moreover, the unique spatial property of the fluorescence can help one to separate fluorescence and interferometric signals.

FIG. 4 illustrates an exemplary embodiment of an integrated fluorescence and interferometric microarray detection system. The embodiment shown in FIG. 4 comprises a laser 40 (e.g., INNOVA300 laser from Coherent Inc.), a linear stage 42 (e.g., MM2K stage from Newport), a spin motor 44 (e.g., Scanner motor from Laser Lines Ltd), a biological compact disk 46, a quadrant detector 48 (e.g., PC50-6 from Pacific Silicon Sensor Inc.), an avalanche photodiode detector ("APD") 50 (e.g., C5460-01 from Hamamatsu Company), an oscilloscope 52, a computer 54 and some optical components such as mirrors, filters and lens. This embodiment is designed to acquire three channels simultaneously. The quadrant detector 48 is responsible for two interferometric channels, and the APD detector 50 acquires fluorescence signals from an analyte on the biological compact disk 46.

For mapping a whole disk, two free coordinates are established to form a polar coordinate system. The spinning motor 44 is used to rotate the biological compact disk 46 and serves as the angular coordinate when the motor spins in a selectable frequency ranging from about 20 Hz to about 80 Hz. The linear stage 42 serves as the polar coordinate and moves back and forth with 0.1 µm linear precision and 300 mm maximum travel distance. The motor 44 is fixed to the linear stage 42 so that two-dimensional mapping can be realized with appropriate computer control. This system is capable of mapping a 100 mm diameter biological compact disk in about 30 minutes with 2 µm by 2 µm pixel resolution.

In this embodiment, the illumination from the laser 40 has a wavelength of about 488 nm and serves as the probing light. The laser beam is filtered, steered and focused onto the surface of the biological compact disk 46 with a filter, several mirrors and one 10 cm convex lens. The radius of the focal spot is about 20 µm on the disk 46; however, higher resolution can be achieved by switching to a 10 cm short focal length lens or even a microscope objective lens. The reflected light is guided into the quadrant detector 48, which is responsible for acquiring the interferometric signals (i.e., phase contrast and in-line signals), and a 4 cm convex lens above the disk 46 gathers fluorescence and sends it into an APD 50 equipped with a 510 nm long-pass optical filter to block the scattered laser light.

An oscilloscope 52 is responsible for acquiring the waveform for each scanned track of the disk 46. The APD 50 and quadrant detector 48 are connected with three channels (e.g., channels 1, 2, 3) of the oscilloscope 52 via coaxial cables (see the lines from the oscilloscope to the detectors in FIG. 1). Two of these cables are for the quadrant detector 48 so that it can acquire the two types of interferometric signals (i.e., phase contrast and in-line signals). Another coaxial cable connects the spin motor 44 to the oscilloscope 52. The spin motor 44 generates a trigger signal for the oscilloscope 52. The computer 54 controls the movement of the linear stage 42 and records data from the oscilloscope 52. Two SCSI cables (see the lines from the computer in FIG. 1) are used to connect the computer 54 to the linear stage 42 and to the oscilloscope 52.

The embodiment shown in FIG. 4 has an oblique incidence design to benefit from the two distinct solid angular emission distributions caused by the different coherent properties of the fluorescence and interferometric signals. In an oblique incidence design, the probe laser beam is adapted to be incident obliquely and focus on the surface of the biological compact disk 46 to collect fluorescence with the convex lens above the disk. In this configuration, the reflected light does not enter the fluorescence collection lens, but the fluorescence can be acquired with good efficiency. Meanwhile, interferometric signals can be detected via acquiring the reflected probing light. In this way, two types of signals are detected simultaneously without influencing each other.

As opposed to an oblique incidence design, traditional fluorescence detection systems collect fluorescence and reflected probing light together and then separate them with optical filters. While this method is practical for most common biosamples, when applied to a biological compact disk, the detection efficiency of the fluorescence can be low from the fluorophore monolayer (1~10 nm thickness) on the surface. Empirically speaking, the photon flux ratio between the fluorescence and the probe light is about $1:10^7$. If the reflected probe light is mixed into the fluorescence channel, the extremely strong background light causes a large influence on the fluorescence detection precision. However, it has been found that if one or more long-pass filters are used, the background light can be minimized. In order to decrease the background light to a reasonable extent, 4 to 5 filters (as a filter stack) may be used in some embodiments.

Since the photon flux of the fluorescence is low (about 1 nw for collection efficiency), the addition of the filter stack can negatively influence the low flux. More particularly, fluorescence flux is decreased by 25% for each filter used (i.e., when four filters are used, only 0.4% fluorescence survives). Moreover, the probe laser is not 100% pure. For instance, the INNOVA300 Argon laser generates mostly 488 nm wavelength light with 0.1 W operation power. However, there are still some long light wavelengths (e.g., 514 nm and 528 nm) with a ratio constituent above 0.01%. These wavelengths are inside the spectrum band of fluorescence so they are mostly immune to the 510 nm LP filter. As such, extra optical filters would be needed to purify the laser beam beforehand.

Oblique incidence greatly minimizes the above-mentioned issues. More particularly, since reflected probe light does not affect fluorescence, only one filter is needed for wavelength filtering, and only one, or possibly even zero, optical filters are needed for laser purification. Thus, to achieve a low fluorescence flux, spatial filtering processes (such as the oblique incidence method) can help improve fluorescence collection efficiency and suppress background noise.

Figure 6A:
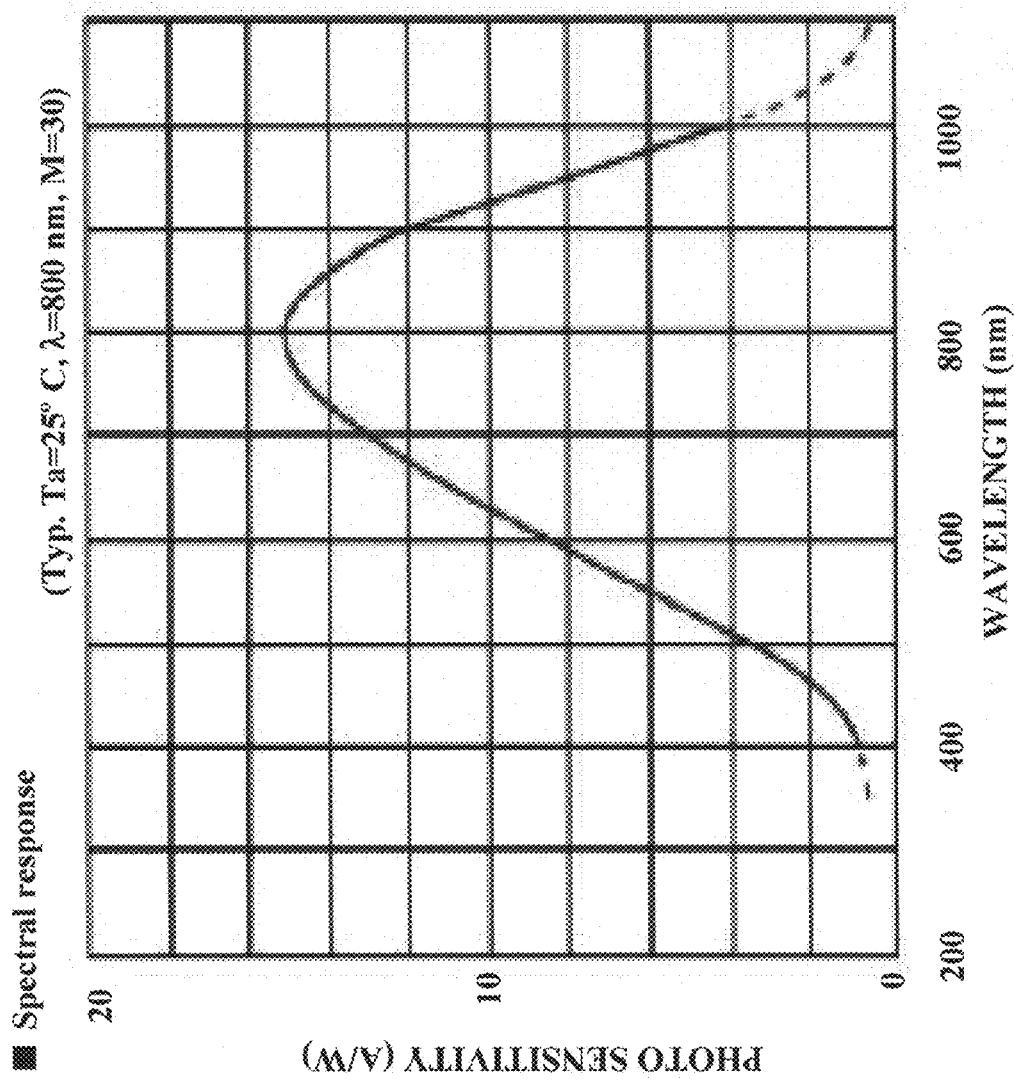
FIGS. 6A and 6B show the spectral response and sampling frequency response for the −01 avalanche photodiode.
Figure 6B:
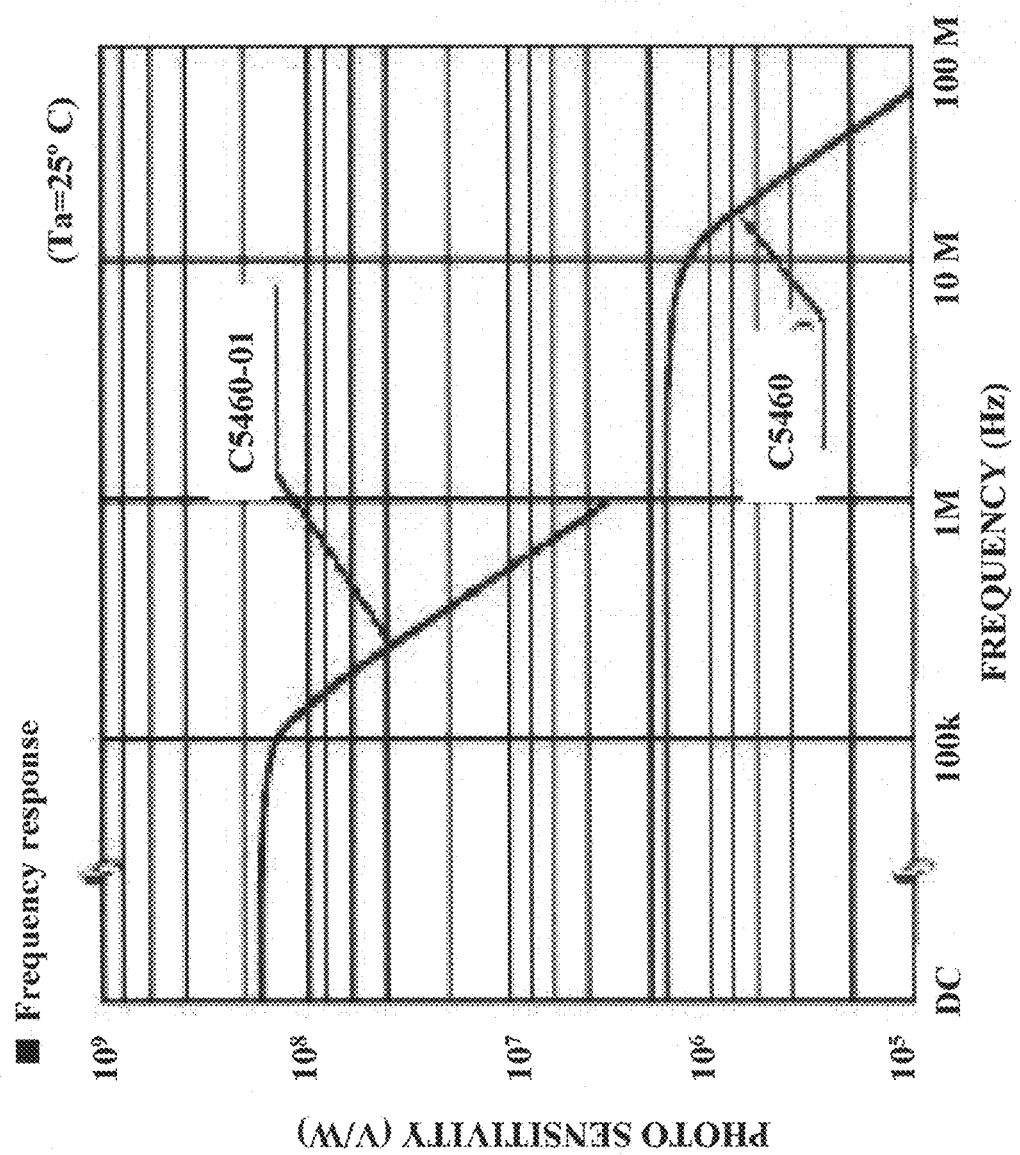

High speed and sensitivity Avalanche photodiodes (APD) are widely used in low photon flux detection processes. In one exemplary embodiment of the present system, an APD (e.g., C5460-01 from Hamamatsu Photonics K.K.) serves as the fluorescence detector. As is seen in the exemplary datasheet of FIG. 5, the amplification of the APD is approximately 0.15 Gigavolt/W at 800 nm. Considering 520 nm as the central emission wavelength for fluorescein, it can be estimated that the real amplification for fluorescence, according to the spectral response curve, is 0.05 Gigavolt/W (see FIGS. 6A and 6B).

Background noise of the APD is expected to be 6 pW according to the noise equivalent power from the datasheet (FIG. 5). Therefore, the detection limit of fluorescence is about 6 pW, without the aid of electronics (e.g., op-amp, frequency filters) or numerical signal enhancement approaches (e.g., signal processing such as FFT). According to tests of the present system, the detection limit is equivalent to 0.3 pm thickness of the protein layer conjugated with fluorescein, i.e. 0.3 pg/mm² protein planar density on the disk.

Frequency response is another important parameter of the APD. This parameter sets the upper limit for the detection speed. As can be seen in FIG. 5, the signal frequency response is approximately 100 kHz, such that if the system scans 100 μm diameter protein spots on a biological compact disk with 0.05 second spin period (20 Hz), the central frequency for the spot signal can be estimated to equal 60 kHz (i.e., 20 Hz×0.3 m/0.1 mm) on the outer ring of disk. Therefore, a spin frequency of 20 Hz would be acceptable for a scanning system operating with a C5460-01 APD. If a higher spin frequency is demanded, then a lower amplification but higher response rate (such as C5460) could accommodate this requirement.

As mentioned above, the fluorescence detection limit can be extended if the APD's noise is carefully analyzed and exploited, particularly since the frequency band of the fluorescence signal can be separated from the major band of the noise spectrum.

Figure 7:
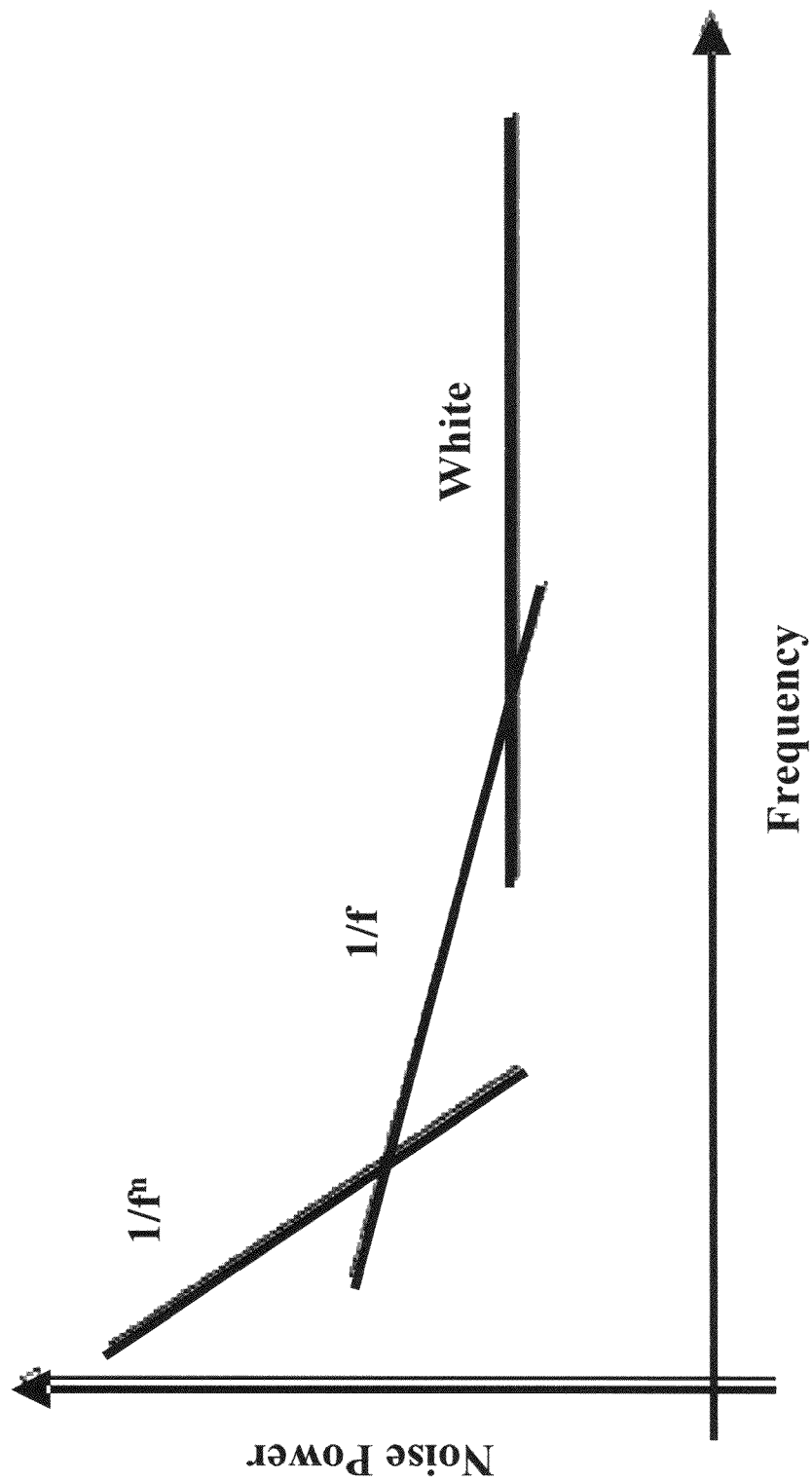
FIG. 7 illustrates the noise character in fluorescence systems for different frequencies.

Noise in fluorescence systems tends to be dominated by amplifier noise because of the associated low photon flux and high gain of these systems. This noise can have a 1/f character at low frequencies, and may have white noise properties at higher frequencies. The change in signal-to-noise with a change in the detection bandwidth depends on the frequency dependence. The different conditions are shown generically in FIG. 7.

In the exemplary embodiment of the current invention, the laser beam passes rapidly over a succession of protein spots. Therefore, this embodiment constitutes a laser scanning configuration. Laser scanning can be accomplished either by a linear raster of the laser beam while the target remains fixed, or the laser beam can remain fixed while the target moves. In our case, the laser remains fixed and the target moves. The rotation of the spinning disc brings the same protein spot back to the probe laser many times. This represents high-speed sampling that has a strong advantage in the signal-to-noise ratio for scanning systems relative to static measurement systems. To show the advantages of high-speed spinning and scanning, we show how the signal-to-noise is improved over static measurements for the case of 1/f noise.

Static Measurement with 1/f noise: For a static measurement, the signal from a target location is measured with an integration time T, after which the laser is moved (or the target is moved) to a new location to begin the next measurement. The effective sampling frequency in this case is f=1/T, and the effective bandwidth is BW=f=1/T. The noise in the signal is given by:

$$P_N = P_f * BW/f = P_f$$

and the detection bandwidth cancels the 1/f component of the noise, and no advantage is obtained by averaging.

High-Speed Repetitive Measurements with 1/f noise: In this case, the sampling frequency is set by the transit time Δt from one spot on the disc to the next so f=1/Δt. The detection bandwidth is set by the integration time BW=1/T. The noise power is then given by $$P_N = P_f * BW/f = P_f * \Delta t/T$$

which is made smaller by choosing a shorter transit time (higher speed) and integrating longer. The comparison of the spinning detection noise to the static detection noise described above shows the clear advantages of high-speed spinning that are embodied in the biological compact disc concept. These noise arguments hold equally for both fluorescence and interferometry. The dual-mode detection we describe here therefore benefits directly from the high-speed spinning in the presence of 1/f noise.

The following discussion about the electrical field of the disk is based on the condition that the incident light's polarization is parallel with the disk's surface.

The surface of the biological compact disk is designed to enhance in-line and phase contrast sensitivities of the disk. This sensitivity can be predicted by determining the reflection coefficient r of the surface. Fluorescence sensitivity can also be determined by the reflection coefficient r. Because the analyte monolayer of the surface is thin (less than 10 nm, about 1/50 of the wavelength), the optical properties of the surface influence the fluorescence excitation efficiency, particularly since the surface electrical field is determined by the interference between the reflected light and the incident light. For example, when the reflection coefficient of the microarray surface is −1, the surface will be at the standing wave's node position. In this case, the electrical field is almost zero in the proximity of the surface so that the fluorophore will not be excited and the biolayer will not contribute a phase change. On the other hand, when the reflection coefficient of the microarray surface is +1, the electric field is a maximum in the proximity of the surface so that the fluorophore will be excited, and the biolayer contributes a maximum phase shift that would be detected in a phase-contrast detection system.

A primary concept for the current embodiment of the invention is the optimum excitation of both fluorescence and phase-sensitive detection (either phase-contrast or in-line). In the case of r=+1, the maximum field automatically gives the maximum fluorescence and maximum phase contrast signal together. This is one exemplary embodiment of the current invention.

In the case of in-line detection, there is a trade off between electric field strength at the surface and the condition of phase quadrature that must be set by the substrate structure. For in-line interferometry, the optimum phase condition is a pi/2 phase shift, but this phase condition produces half the electric field at the surface, which decreases both the phase contribution of the biolayer for interferometric detection and the fluorescence intensity. Therefore, a balance must be set in the design that keeps the surface field as large as possible, while also keeping a phase condition reasonably near to quadrature.

Because the fluorescence excitation efficiency is proportional to the intensity of the electrical field, if the incident light's amplitude is E, then the surface electrical field is $$(1+r)E \cos \omega t$$

on the disk surface, where r is the reflection coefficient. This relationship helps to predict the fluorescence excitation efficiency due to the optical property of the disk surface. As a result, the following conclusions can be reached: (1) if r=−1, the excitation efficiency is zero; (2) if r=1, the excitation efficiency is maximized; (3) if r=0, the excitation efficiency is half of the maximum value; and (4) the requirement for r is quite loose. In most situations, fluorescence excitation efficiency is rather large. This provides freedom to design a suitable reflection coefficient to accommodate the interferometric channel's sensitivity, since it is more rigorous for a suitable r.

Figure 8A:
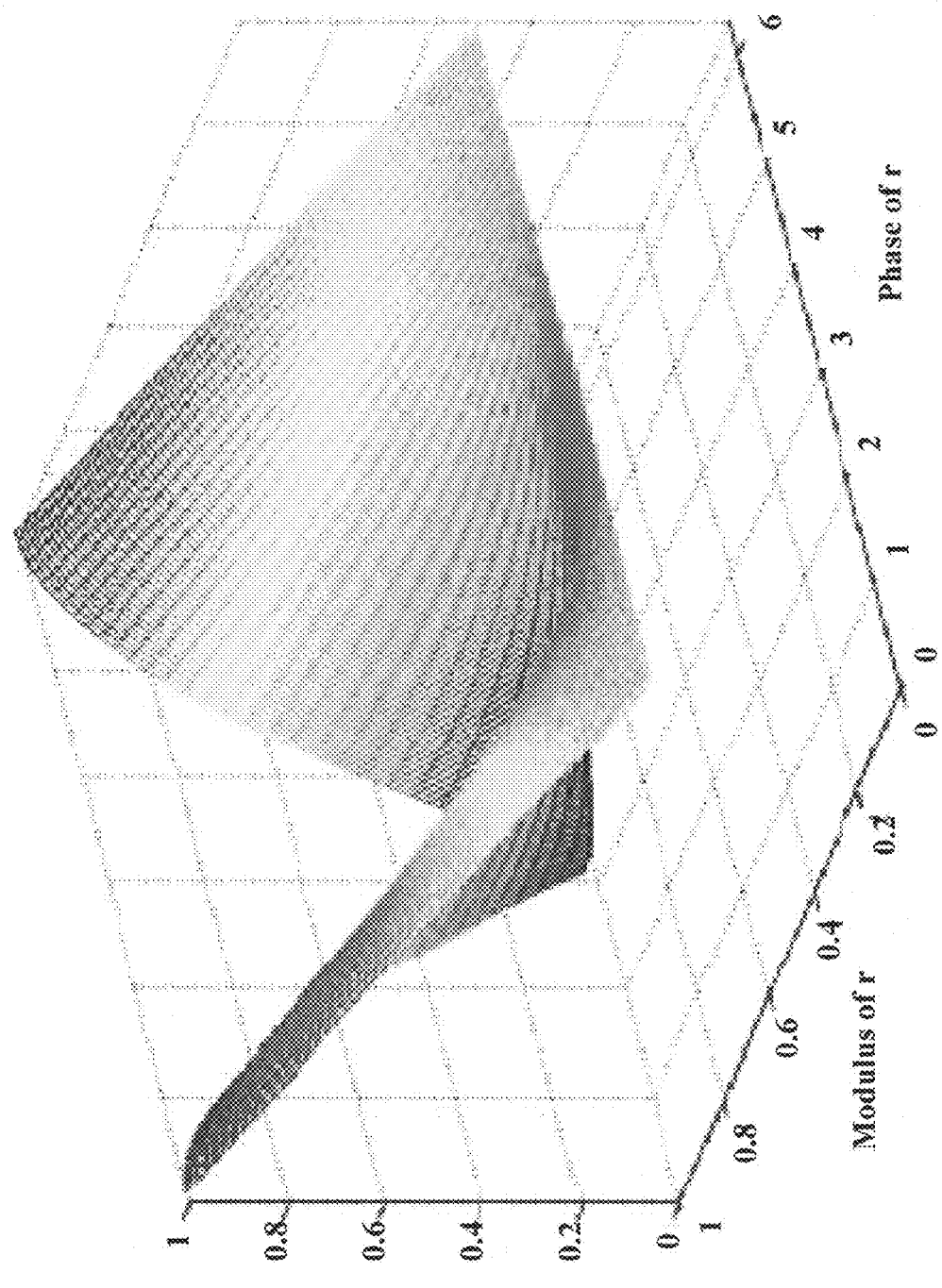
FIG. 8A shows the relationship between the fluorescence excitation efficiency and the reflection coefficient of the biological compact disc.
Figure 8B:
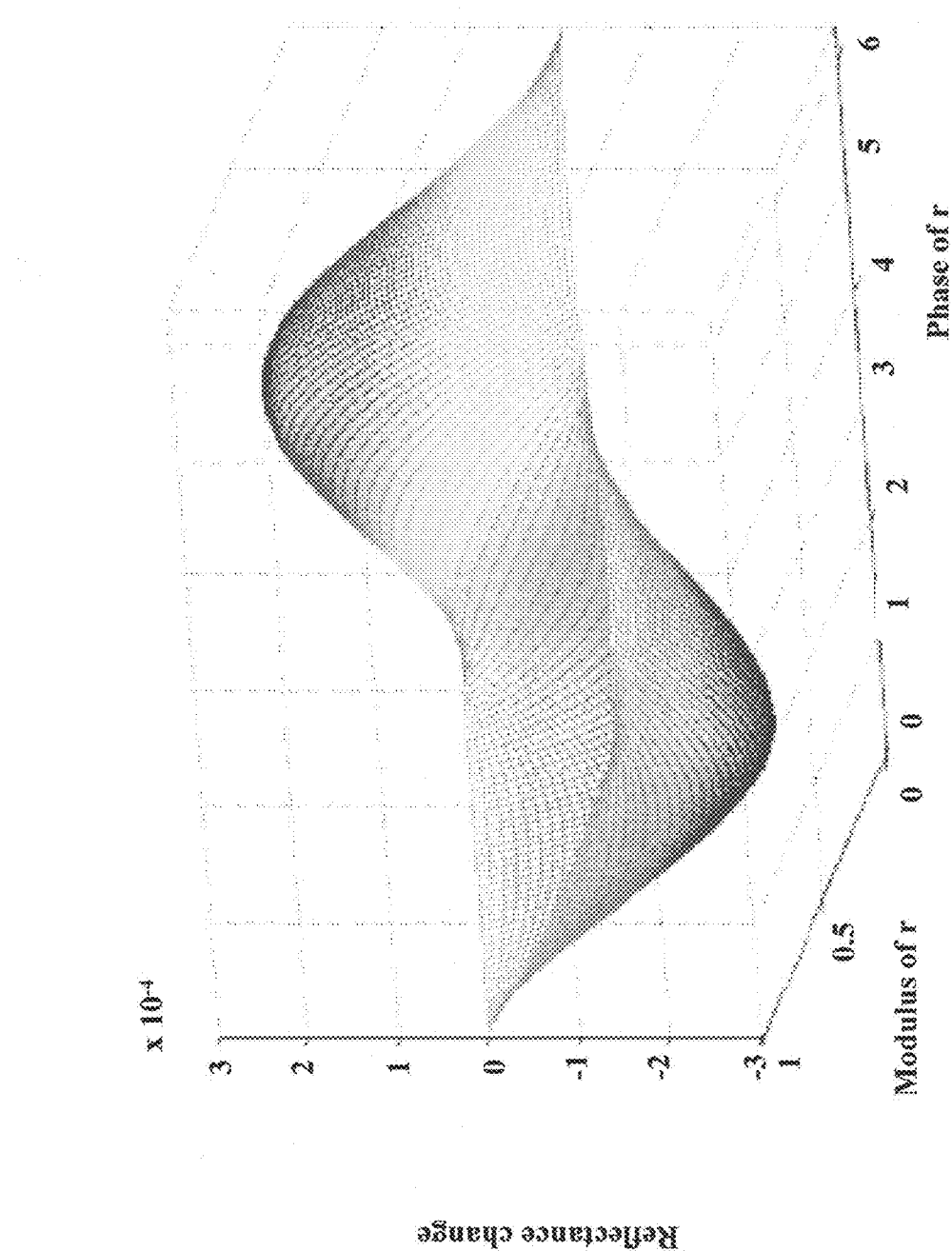
FIG. 8B shows the relationship between the sensitivity of in-line interferometric channel and the reflection coefficient of the biological compact disc.
Figure 8C:
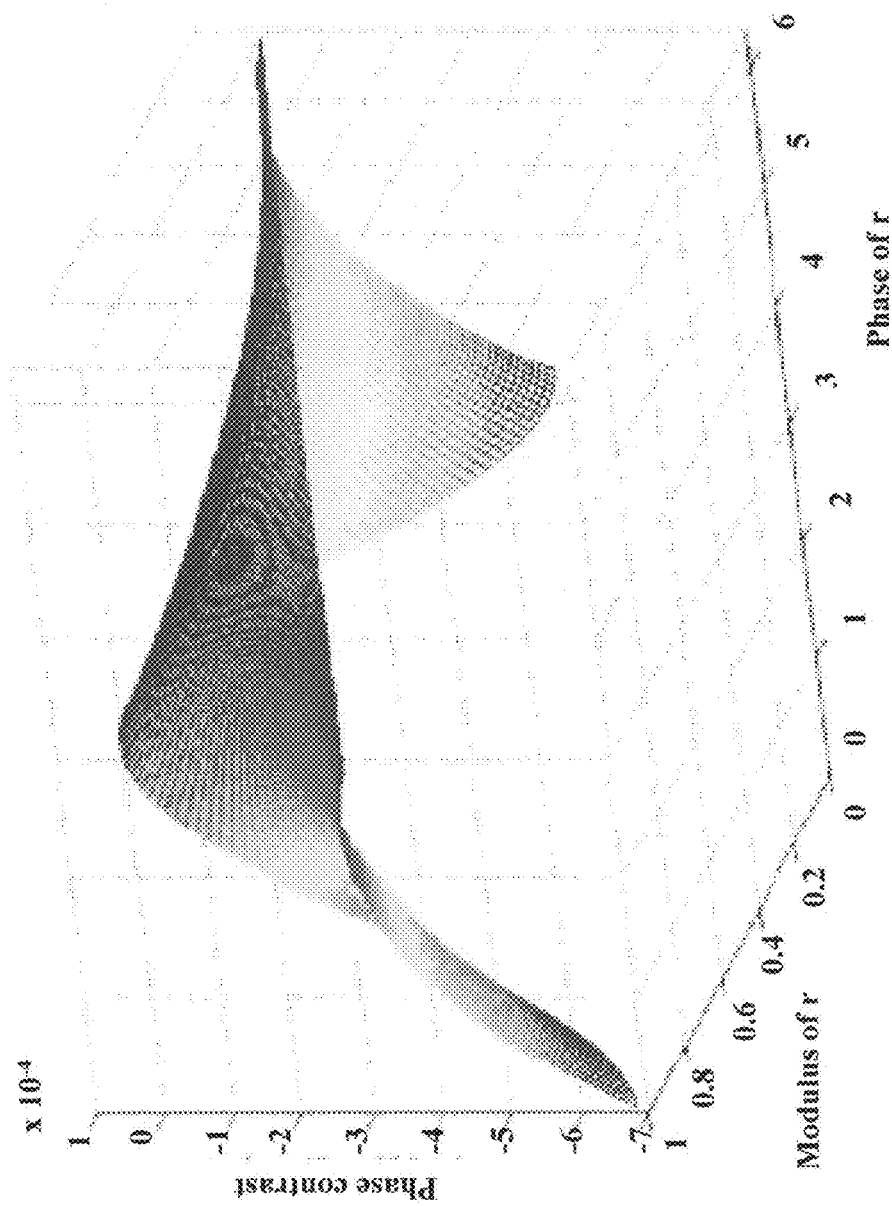
FIG. 8C shows the relationship between the sensitivity of phase contrast interferometric channel and the reflection coefficient of the biological compact disc.

The three-dimensional plots of FIG. 8 illustrate the relationship between r and the channel's sensitivity. Since r is a complex quantity, it needs two dimensions (modulus and phase) to be expressed. FIG. 8A shows the relationship between the fluorescence excitation efficiency and the reflection coefficient of the biological compact disc. FIG. 8B shows the relationship between the sensitivity of in-line interferometric channel and the reflection coefficient of the biological compact disc. FIG. 8C shows the relationship between the sensitivity of phase contrast interferometric channel and the reflection coefficient of the biological compact disc.

Biological compact disks used in this embodiment can include silicon disks coated with 100 nm of silica film. These disks are useful for commercial applications, particularly because they are inexpensive to manufacture yet still exhibit robustness and good sensitivity for all channels. Such disks are particularly useful for in-line interferometric channel sensitivity applications. With respect to fluorescence detection applications, since fluorescence excitation efficiency is $\propto |1+r|^2$, r can be calculated by considering the following factors:

| | |
|---|---|
| Incident angle | 30 degrees |
| Polarization direction | parallel with disk's surface |
| index of air | 1 |
| index of silicon dioxide | 1.46313 |
| index of Silicon | 4.379 |

It can be calculated that r=0.27−0.24i. Therefore, $|1+r|^2=1.67$. This value is quite large considering that the maximum value is 2. In this case, the fluorescence excitation coefficient should be good, while the phase shift is close to the pi/2 phase required for in-line interferometric detection.

The present embodiment has been tested with gel-printed protein grating patterns and spot-style immunoassays. The former pattern can provide a periodic signal for system calibration and for the analysis of the signal power spectrum. The latter shows the system's potential applications for biological research.

Figure 9A:
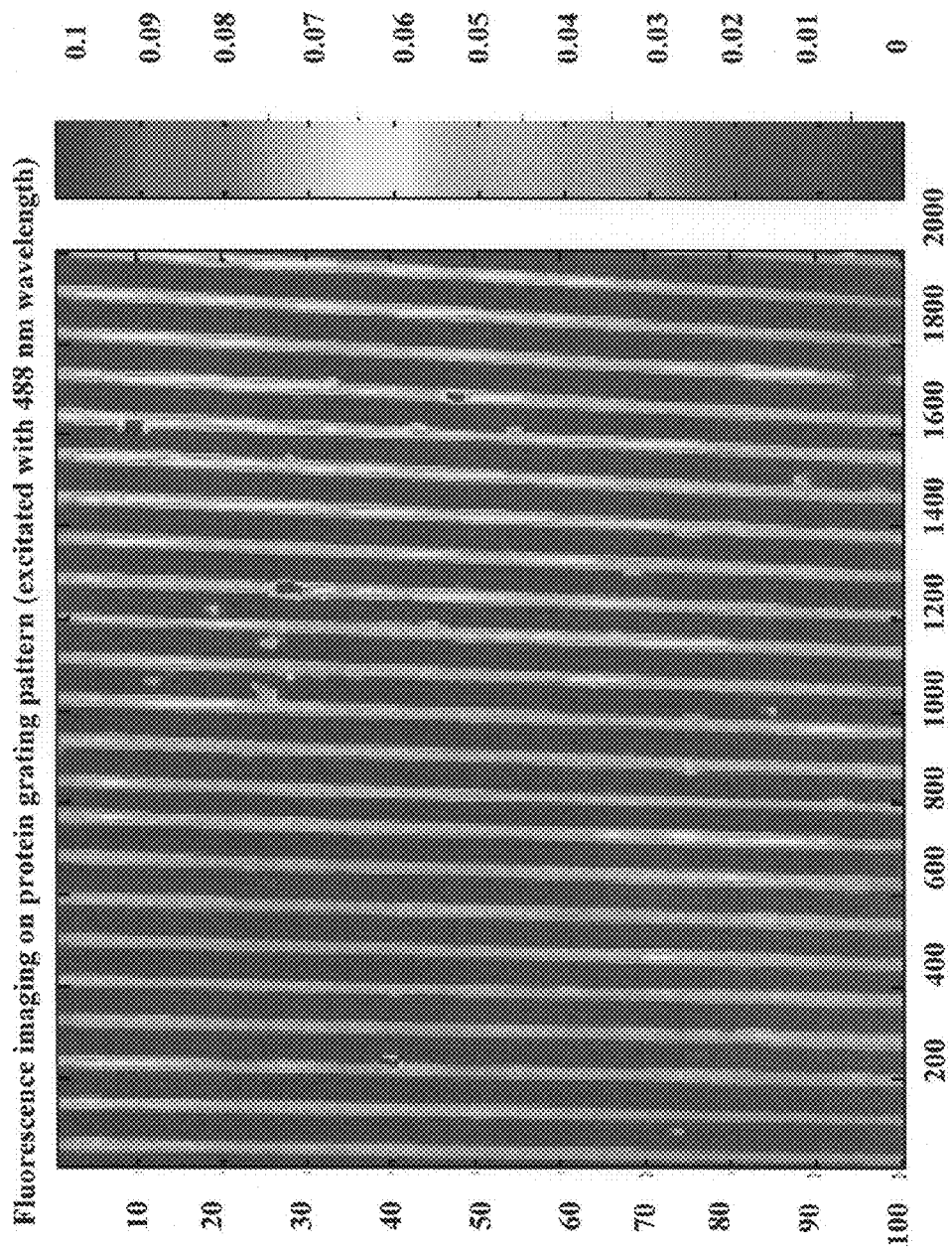
FIG. 9A shows an image of the fluorescence for a biological compact disk imaged simultaneously with both fluorescence and interferometric methods on the same protein grating pattern region shown in FIG. 9B.
Figure 9B:
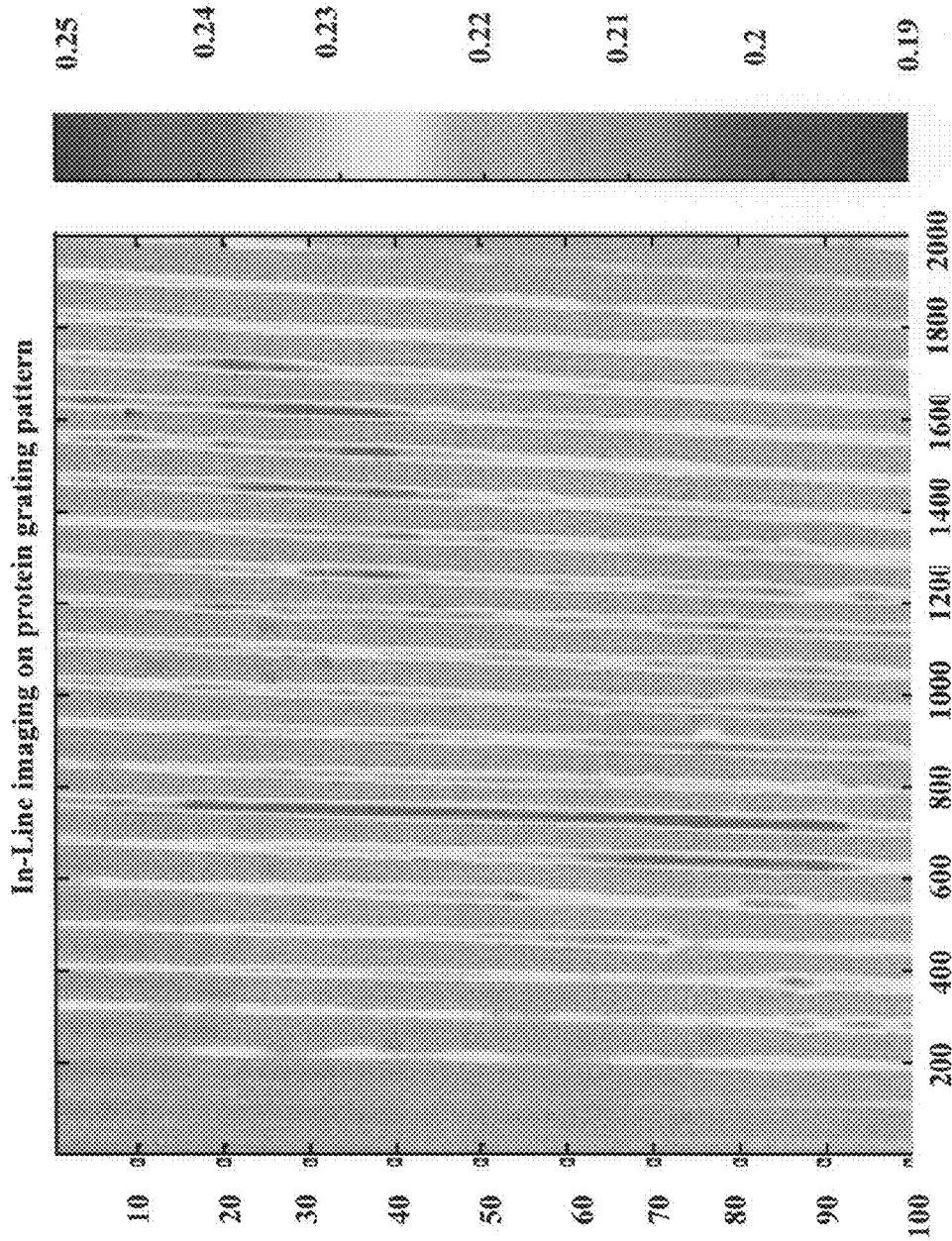
FIG. 9B shows an image of the in-line interferometry for a biological compact disk imaged simultaneously with both fluorescence and interferometric methods on the same protein grating pattern region shown in FIG. 9A.

For the gel printed protein pattern, a physical adsorption method is used to immobilize protein molecules on the substrate surface. According to this example, a hydrophobic activation was performed on the silicon dioxide layer of the disk by surface silanization (the disks were soaked in 0.02M chlorooctadecylsilane Toluene solution for 12 hours). The proteins adhere to the silanized disk surface through hydrophobic interaction. Bovine serum albumin conjugated with fluorescein (A9771, Sigma corp.) is then printed on the disk in a grating pattern with a gel stamp method. The width of each protein stripe is about 100 um, and the gap between stripes is about 120 um. After printing, the surface of the disk is rinsed with de-ionized water and then blown dry with purified nitrogen to establish the protein layer as a monolayer. The results of two-channel scanning are shown in FIG. 9. On the same protein grating pattern region (whose thickness is about 1~4 nm—approximately a monolayer), an imaging scan is performed simultaneously with two channels. FIG. 9A shows the light-scattering fluorescence, and FIG. 9B shows the in-line interferometry illuminated at 488 nm. The cross correlation value between FIGS. 9A and 9B is 0.83, thereby showing that the two results are highly correlated in this case.

Figure 10B:
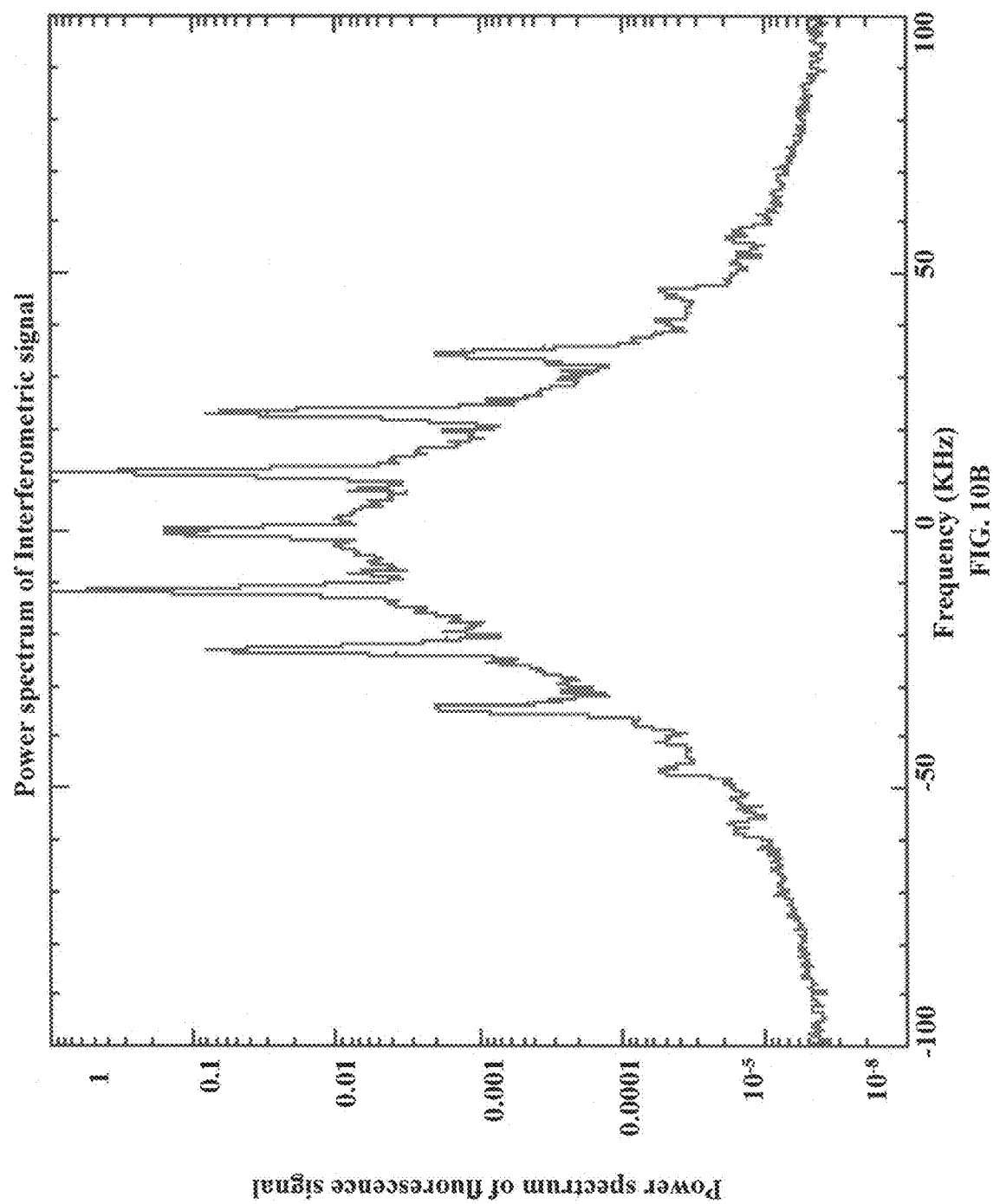
FIG. 10B shows the power spectrum corresponding to FIG. 10B.

FIGS. 10A and 10B show the power spectra that correspond to FIGS. 9A and 9B, respectively, using the Fast Fourier Transform Method. The spikes on the spectrum shoulder come from the periodic protein stripe pattern. The Signal-to-Background Ratio (SBR) can then be derived from the spectrum chart. Here, since it is known that the thickness of the protein layer is about 1-3 nm (monolayer), the SBR for the fluorescence and interferometry channels are in the range of 300:1~500:1. The detection limit for the lowest protein layer can be estimated as 1~2.5 pm, i.e. 1~2.5 pg/mm$^2$ planar density, which is close to the detection limit (i.e., 0.3 pg/mm$^2$), which is estimated from the APD detection limit as discussed above.

It was also found that the first 'spike', which is the fundamental harmonic, is almost at the top of the spectrum shoulder, which exhibits the 1/f noise of the system (mostly originating from the APD). This indicates that target signal is not separated away from the 1/f noise frequency domain on this sample. This is because of the motor's low spinning frequency (20 Hz) and the relatively large distance between the protein stripes. When scanning smaller samples (e.g., submillimeter spots with 80 Hz spinning frequency), the SBR could be improved by about a factor of 10, which means that the detection limit can be extended to 0.1~0.25 pg/mm$^2$.

This embodiment's capacity to quantify immunoassays with high background protein concentration was then tested. Only the fluorescence and amplitude channels were used because they have the highest SBR. In this exemplary illustration, the "sandwich model" immunoassay strategy is applied to a biological compact disk (i.e., 100 nm silica coated silicon disk). To detect the target antigen's concentration in the solution sample, which has a high background concentration, the corresponding antibody is immobilized on the disk, and then the disk is incubated with the analyte solution. Consequently, the antibody binds with the target antigen so that the antigen is anchored on the disk, while the background non-specific protein is washed off. When the target antigen is captured on the disk, the antigen can be incubated with a fluorescein-conjugated antibody (for fluorescence detection) or an unconjugated antibody (for interferometric detection). The fluorescence intensity or interferometric signal's increment is linearly related to the antigen concentration in the original solution. Using a standard responsive curve illustrating the relationship between the antigen concentration and the signal increment, it is possible to acquire the antigen concentration quantitatively.

In an experimental procedure, eight wells of antibody spots are printed on an oxidized silicon disk. Each well includes a 2×2 array of spots arranged in a unit-cell configuration. The unit-cell configuration for this experiment comprises two spots on a first diagonal of anti-rabbit IgG, and two spots on the other diagonal of non-specific Horse IgG which are a control. These eight wells are incubated respectively with 0, 0.01, 0.03, 0.1, 0.3, 1, 3 and 10 ug/ml Rabbit IgG in 7 mg/ml rat lysate and then scanned. Thereafter, the spots are sequentially incubated with 20 ug/ml anti-rabbit-biotin, 20 ug/ml avidin, 20 ug/ml anti-avidin, with a scan being performed after each incubation process.

Figure 11A:
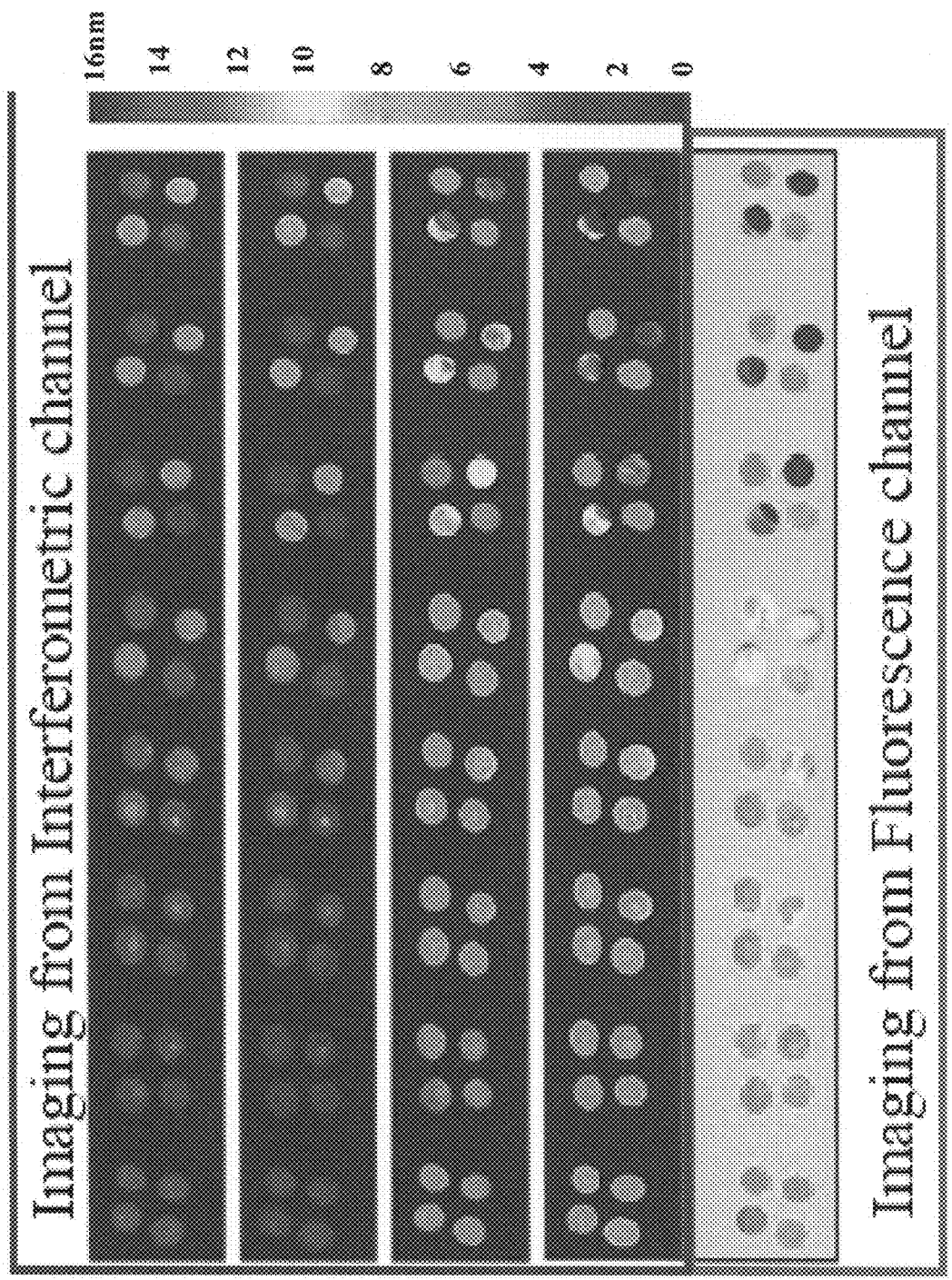
FIG. 11A shows the imaging from the interferometric channel at different phases in the experimental procedure in the upper four rows, and shows the imaging from the fluorescence channel in the bottom row.

The upper four rows of FIG. 11A show the thickness of the protein spots acquired from the interferometric channel. The first row shows the thickness of the spots after incubation with the series of rabbit IgG solutions in the concentration ladder. The second row shows the thickness of the spots after incubation with the anti-rabbit-biotin. The third row shows the thickness of the spots after incubation with the avidin. The fourth row shows the thickness of the spots after incubation with the anti-avidin-FITC. The fifth row shows fluorescence signals after incubation with anti-avidin-FITC.

Figure 11B:
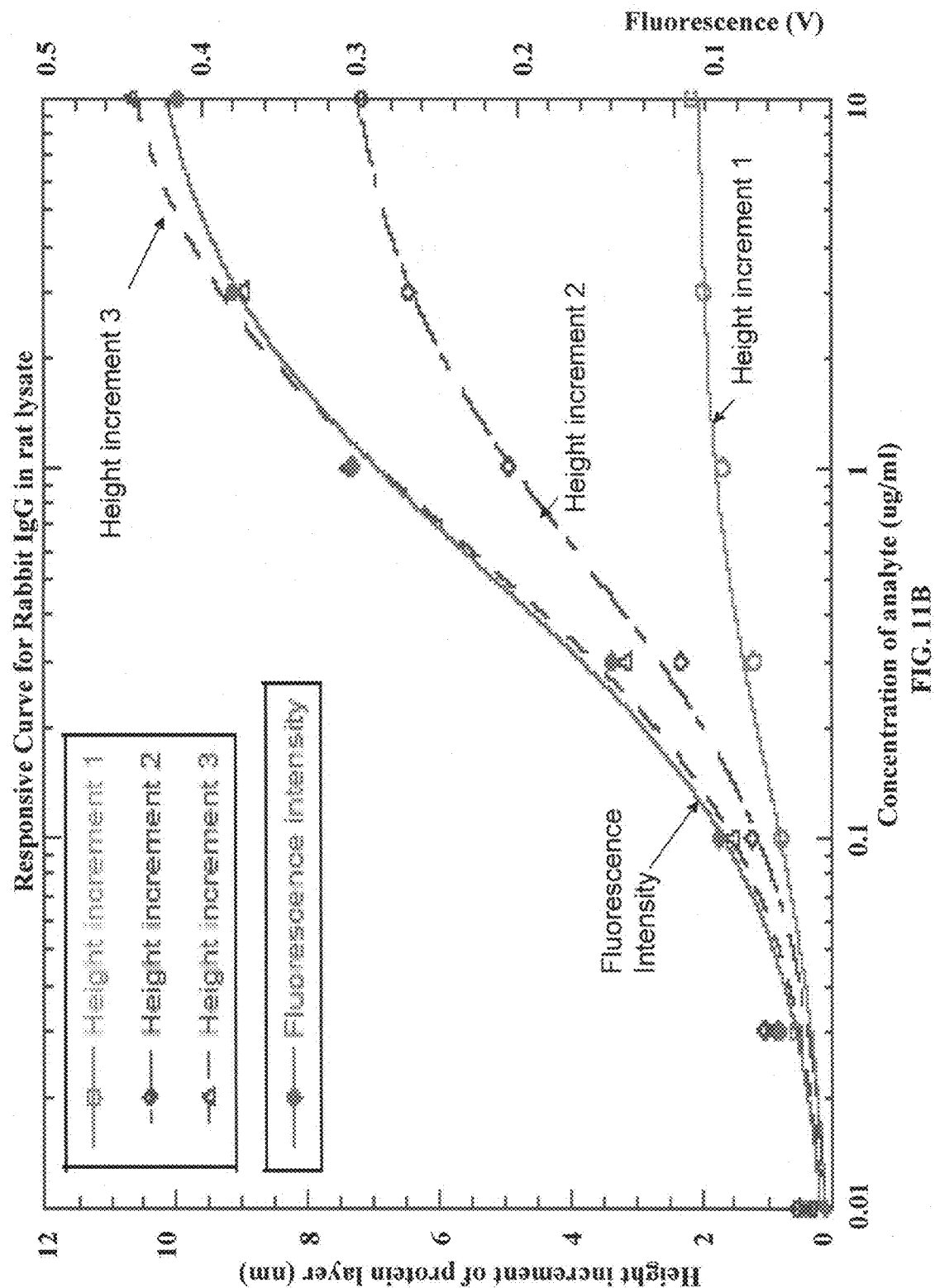
FIG. 11B shows the response curve for the analyte concentration ladder on both the fluorescence and interferometric channels.

FIG. 11B shows the response curves for the analyte concentration ladder on both the fluorescence and interferometric channels. In FIG. 11B, the curves show spot thickness increments after each incubation process as a function of concentration. All of the curves are fitted with the Langmuir binding equation:

$$\Delta d = C \frac{[\text{antibody}]}{K_D + [\text{antibody}]}$$

where $K_D$ is the dissociation constant between antigen and antibody, or between avidin and biotin-conjugated protein. In the three curves for the interferometric channel, the increments increase monotonically with increasing concentrations indicating that the detection limit is below 10 ng/ml. The fluorescence response curve (upper solid curve) shows the same trend. As such, this experiment shows that the system succeeds in reaching 0.01 ug/ml detection limits on both the fluorescence and interferometric channels in the presence of 7 mg/ml complex protein background.

Another exemplary embodiment comprises a four-channel detection method for protein-patterned biological compact disks that simultaneously measures fluorescence, Rayleigh scattering and/or diffraction, and two interferometric channels in orthogonal quadratures (i.e., a differential phase channel and a direct phase channel). The latter two channels constitute label-free interferometric protein detection, while fluorescence and Mie scattering detection provide complementary tools.

Optical biosensors normally include a probe light and one or more detectors. When illuminated by probe light, protein molecules containing a fluorophore are excited and then emit fluorescence, or protein by itself scatters the probe light. By detecting fluorescence or scattered light, the protein information is obtained. For both cases, a discrete dipole approximation can be used to analyze the absorption, fluorescence, or scattering due to molecules. One sub-wavelength size molecule is considered as one discrete dipole when fluorescence or scattering occurs. Subsequently, a protein agglomerate or a protein layer on a surface could be treated as a group of dipoles. Within this approximation, the optical properties of the four channels are analyzed.

Protein molecules are immobilized on the dielectric layers on the biological compact disk with complex reflection coefficient r. In the simplest model, molecules are distributed evenly (from a macroscopic view), and they are illuminated with a focused Gaussian laser beam whose waist diameter is D. The polarization is parallel with the surface, shown as the arrow parallel to the x-axis in FIG. 12. Other polarizations are also possible. Every molecule is a discrete dipole when illuminated with the probe light.

Figure 12A:
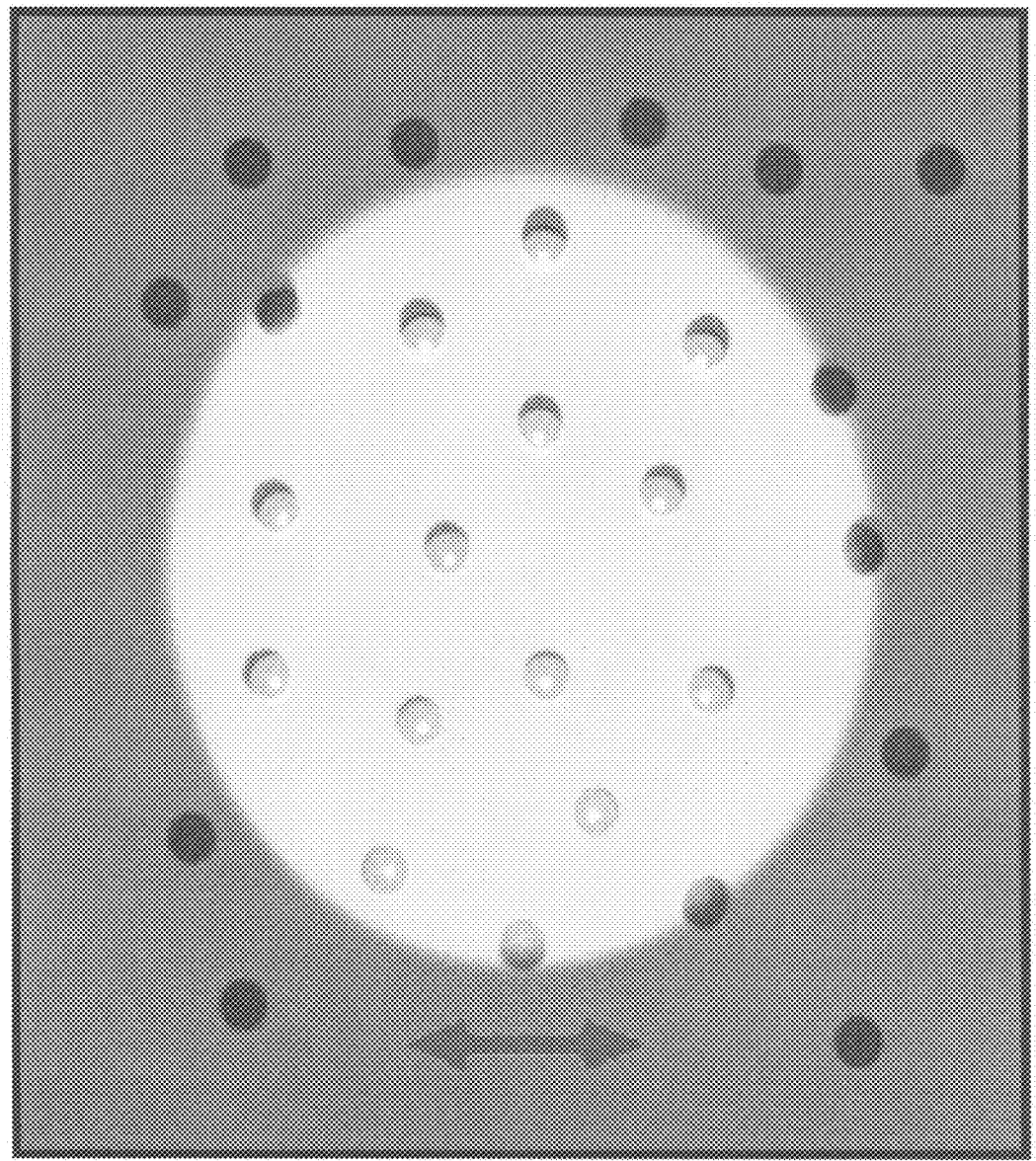
FIG. 12A illustrates protein molecules on the biological compact disk being illuminated with a focused Gaussian beam, polarization being indicated by the arrow.
Figure 12B:
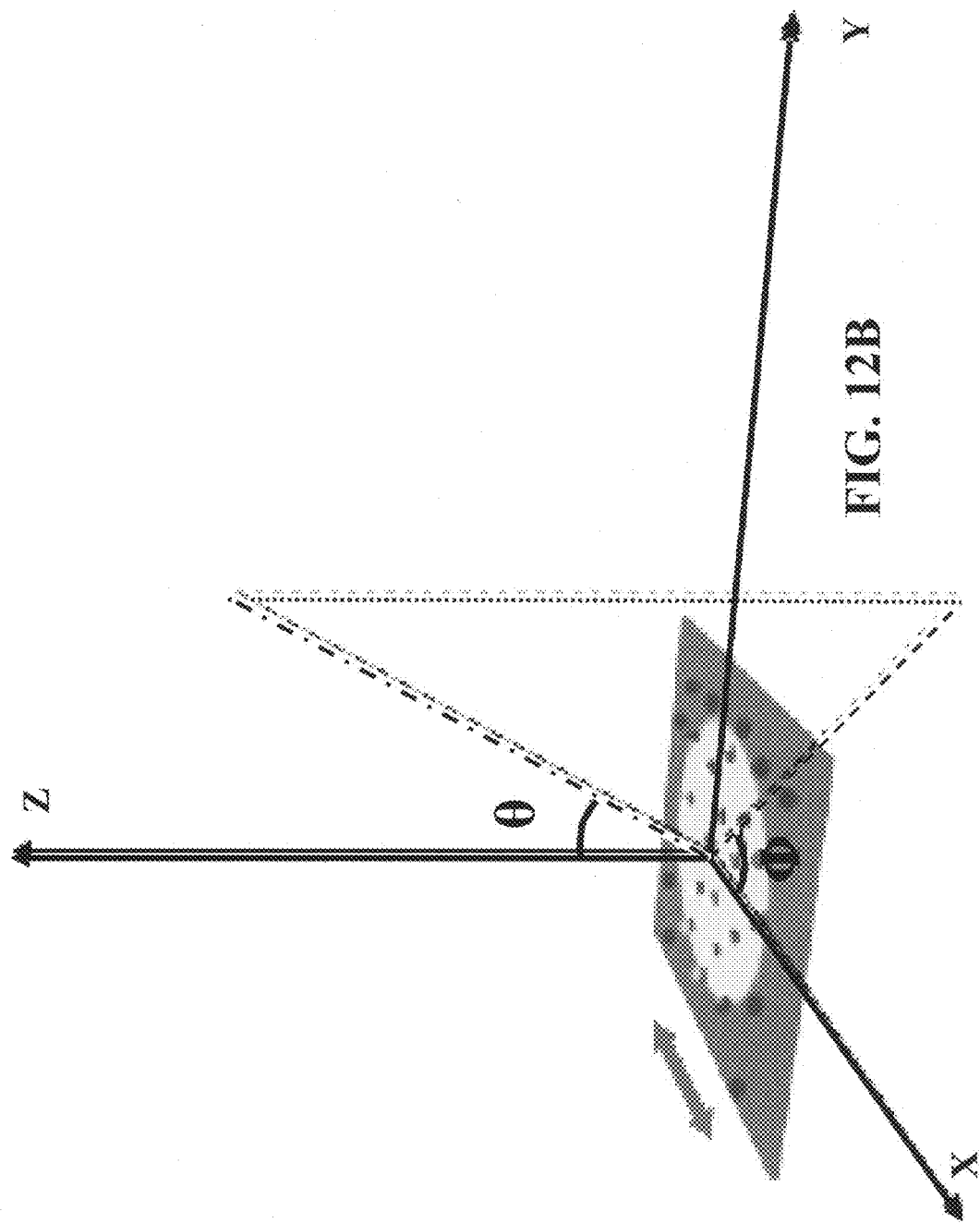
FIG. 12B illustrates an angular coordinate system that can be used to calculate the angular distribution of intensity.

FIG. 12A illustrates protein molecules on a biological compact disk being illuminated with a focused Gaussian beam. Polarization is indicated by the arrow in FIGS. 12A and 12B. Each molecule radiates fluorescence or scatters probe light in the manner of one discrete electric dipole. FIG. 12B illustrates a set of angular coordinates that can be used to calculate fluorescence, Rayleigh scattering (for interferometric channels) and Mie scattering angular distribution of intensity.

A protein molecule has an inherent dipole moment $\vec{P}$ even before excitation. The excitation probability of this dipole is proportional to $\sin^2 \theta \cos^2 \phi$ (where $\theta$ and $\phi$ are angles of $\vec{P}$ in the angular coordinates, shown in FIG. 12B). Within the mean lifetime (usually larger than 1 nanosecond) of the excited energy level, the dipole emits one photon. The probability of emission direction is proportional to $\sin^2 \alpha$ (where $\alpha$ is the angle between the dipole moment and emission direction). To simplify this model, it can be assumed that the dipole moments are oriented isotropically in space. Because the relaxation time of excited molecules is random, and has at least one nanosecond variation, fluorescence from different molecules is incoherent. As a result, the fluorescence intensity distribution in the far field equals the algebraic sum of all the dipole intensities in the far field.

Under these conditions, the fluorescence intensity angular distribution in the far field is:

$$F(\theta, \phi) = \frac{d\sigma}{d\Omega} = K \int_{\phi=0}^{2\pi} \int_{\theta'=0}^{\pi} \sin^2\theta' \cos^2\phi \sin^2\alpha \, d\Omega'$$

$$= K \int_{\phi=0}^{2\pi} \int_{\theta'=0}^{\pi} \sin^2\theta' \cos^2\phi (1 - \cos^2\alpha) d\Omega'$$

$$= K \int_{\phi=0}^{2\pi} \int_{\theta'=0}^{\pi} \sin^3\theta' \cos^2\phi' (1 - (\sin\theta\cos\phi\sin\theta'\cos\phi' + \sin\theta\sin\phi\sin\theta'\sin\phi' + \cos\theta\cos\theta')^2)$$

$$d\theta' d\phi' = \frac{8\pi}{15} K(2 - \sin^2\theta\cos^2\phi)$$

where K is a constant. From this equation, it is obvious that the fluorescence intensity reaches a maximum when $$\phi = \frac{\pi}{2} \text{ or } \frac{3\pi}{2},$$

i.e. along the plane perpendicular to the polarization direction of the probe light. This conclusion suggests the best fluorescence collection position. In the present system, the fluorescence collection lens is immediately above an illuminated region while the probe light is incident obliquely at 30 degrees.

The reflection coefficient r of the biological compact disk surface also affects the fluorescence sensitivity. Because the protein layer on the surface is thin (less than 10 nm, about λ/50), the electromagnetic boundary condition of the surface imposes a large influence on fluorescence excitation efficiency. This is because the surface electric field is determined by interference between reflected and incidence light. For example, when the reflection coefficient r=−1 on the microarray surface, the surface will be at the nodal position of the resulting standing wave. In this case, the electric field is almost zero in the proximity of the surface so that the fluorophore will not be excited.

Fluorescence excitation efficiency is proportional to the magnitude of the electric field. If the incident light amplitude is E, then the surface electric field is $(1+r)E \cos \omega t$ on the disk surface, where the reflection coefficient r is a complex number. Therefore, the fluorescence excitation efficiency is proportional to $|1+r|^2$. The fluorescence intensity angular distribution becomes:

$$F(\theta,\phi) \propto |1+r|^2 (2-\sin^2\theta \cos^2\phi)$$

This equation is valid even after considering fluorescence reflected by the dielectric surface.

Although both interferometric signals and fluorescence can be treated as dipole radiation from molecules, the optical properties have a fundamental difference and thus have different intensity distributions within the solid angle. Interferometric signals arise from coherent Rayleigh scattering. When illuminated with coherent probe light the dipole radiation superposes in the far field. The superposition causes the scattered light to be strongest in the reflected (specular) direction in the far field. For a thin protein layer, the superposed field calculated for dipole radiation coincides with the reflected light calculated using a thin film model. Therefore, to simplify computation the protein layer is treated as a dielectric thin film.

Changes in the protein film changes the reflection coefficient of the biological compact disk. Interferometric channels detect the presence and thickness of the film by monitoring the reflection change. The change can be optimized by careful selection of r. The biological compact disk surface coating is designed to optimize the interferometric and fluorescence channel sensitivities. To optimize the response, the relationship between the reflection coefficient r of the biological compact disk and the reflection change due to a protein layer (see FIG. 13A) is determined. FIG. 13A illustrates that the reflection change is proportional to the thickness of the protein layer when the protein layer on the surface of the disk is thin enough (much less than the probe light wavelength). If the thickness of the protein layer is d, the refractive index is $n_p$, and the reflection coefficient of the biological compact disk surface is r, then the protein layer on the biological compact disk has a new reflection coefficient r' caused by the protein layer which is solved with the matrix method for calculating multiple dielectric layers to be:

$$r' = \frac{(e^{i\delta} - e^{-i\delta})r_0 + r(e^{-i\delta} - r_0^2 e^{i\delta})}{(e^{i\delta} - r_0^2 e^{-i\delta}) + r(e^{-i\delta} - e^{i\delta})r_0}$$

where $r_0$ is the reflection coefficient of the air-protein interface, and $$\delta = \frac{2\pi n_p d \cos\theta}{\lambda}$$

is the phase change caused by the protein layer (single pass). Using this relationship along with the original reflection coefficient r, the new reflection coefficient r', and the thickness of protein layer d, the presence and mass areal density of the protein molecule can be detected by monitoring the change of the reflection coefficient of the biological compact disk. There are two interferometric channels to monitor the reflection change.

The amplitude channel directly detects the reflectance of the biological compact disk. It is called "amplitude channel" because this channel detects the intensity of the reflected radiation that interferes with the light scattered by the protein molecules. Because of the condition of phase quadrature that is established when the reflection coefficient has a pi/2 phase shift, or nearly so, the phase associated with the protein layer is transduced into intensity (amplitude) at the detector. When the system is scanning a protein layer, the reflectance change is:

$$\Delta I_R = I_0(|r'|^2 - |r|^2)$$

If the thickness of the protein layer is thin (much less than the probe light wavelength), $\Delta I_R$ is approximately proportional to the protein layer thickness. With knowledge of r and the reflectance change, the thickness of the protein layer is calculated.

The phase-contrast channel detects the differential phase change of the reflection coefficient. When the system scans the edge of the protein layer, part of the focused spot is reflected with r while the other part is reflected with r'. In the far field, the reflected direction will slightly depart from the original direction, and the shifted angle is proportional to the phase difference between r and r'. A quadrant photodetector (position-sensitive detector) is used to detect this angle shift. The detector sensing window is divided into four quadrants. The center of the reflected light falls evenly on the center so that all quadrants have the same signal. When the reflection angle shifts, the photon flux on the quadrants acquire a small difference. The relation between this difference and the thickness of the protein layer is:

$$\Delta I_\phi = TI_0(\phi' - \phi + 2\delta \tan\theta_p / \tan\theta_0)|r|^2$$

where $\phi'$ and $\phi$ are the phase of r' and r, $\theta_0$ is the incident angle, $\theta_p$ is the refraction angle in the protein layer, and T is the coefficient which converts phase shift into center shift signal $M_T$. Simulations calculate T to be approximately 0.5 in this embodiment.

FIG. 13B illustrates that if protein molecules agglomerate on the surface, Mie scattering dominates, and the scattering can be detectable in the Mie scattering channel. In this embodiment, the Mie scattering channel shares the same optical path with the fluorescence channel, but it could have a separate lens and detector, or share the same lens and use a beamsplitter to direct the scattering channel to a separate detector. Usually, Rayleigh scattering is centered along the reflection direction because of the interference and the redistribution of the scattered electric field. But for larger agglomerations of protein molecules, if the agglomeration size is comparable or even larger than the wavelength of the probe light, then scattered light is detectable away from the reflection direction (see FIG. 13B). This provides an opportunity to separate a scattered signal from light reflected by the dielectric surface to eliminate the background. With appropriate filters, the system can switch between fluorescence and Mie scattering channels, or with the beamsplitter the two channels could be acquired simultaneously with separate detectors. The potential of the Mie scattering channel can be further exploited because protein agglomeration is a common phenomenon on a microarray surface. When the particles are large, even Mie scattering can be predominantly in the forward direction. Therefore, in one embodiment, the Mie channel photodetector could be situated on either side of the interferometric channel. It is also possible to use different quadrants of a quadrant detector to detect the Mie scattering and the interferometric channels separately. In this embodiment, the lower quadrants could be summed or differenced to obtain the in-line and phase-contrast signals, respectively, while the upper quadrant could be used to detect the low-angle forward-scattered Mie scattering.

In the current embodiment, experiments were performed with a biological compact disk having a multilayer dielectric stack structure of ten repeated layers of $SiO_2$ and $Ta_2O_5$ with thicknesses of 113.4 nm and 72.2 nm, respectively, on a glass substrate. Working under the condition of a 30° obliquely incident s-polarized 488 nm laser beam, the surface reflection coefficient is r=−0.58−0.35i. The fluorescence and interferometric channels were appropriately optimized for this biological compact disk.

An oblique incidence design was established for this system to benefit from two distinct solid angular emission distributions due to the different coherent properties of fluorescence and interferometric signals. In oblique incidence, the probe laser beam is incident obliquely on the biological compact disk, and fluorescence is collected with a convex lens above the disk. In this configuration, the reflected light does not enter the fluorescence collection lens, but fluorescence can be acquired with high efficiency. Interferometric signals are detected by acquiring the reflected probe light. In this way, two types of signals are detected simultaneously without influencing each other. The reason for this design is that the fluorescence efficiency is very low from the fluorophore-conjugated protein layer (1~10 nm thickness) on the surface. Empirically, the ratio of photon flux between fluorescence and probe light is about $1:10^7$. If reflected probe light is mixed into the fluorescence channel, the extremely strong background causes a large influence on the fluorescence detection precision. Long-pass filters alone may not be enough to eliminate the background. Spatial filtering, as from oblique incidence, improves the fluorescence collection efficiency and suppresses background.

Figure 14:
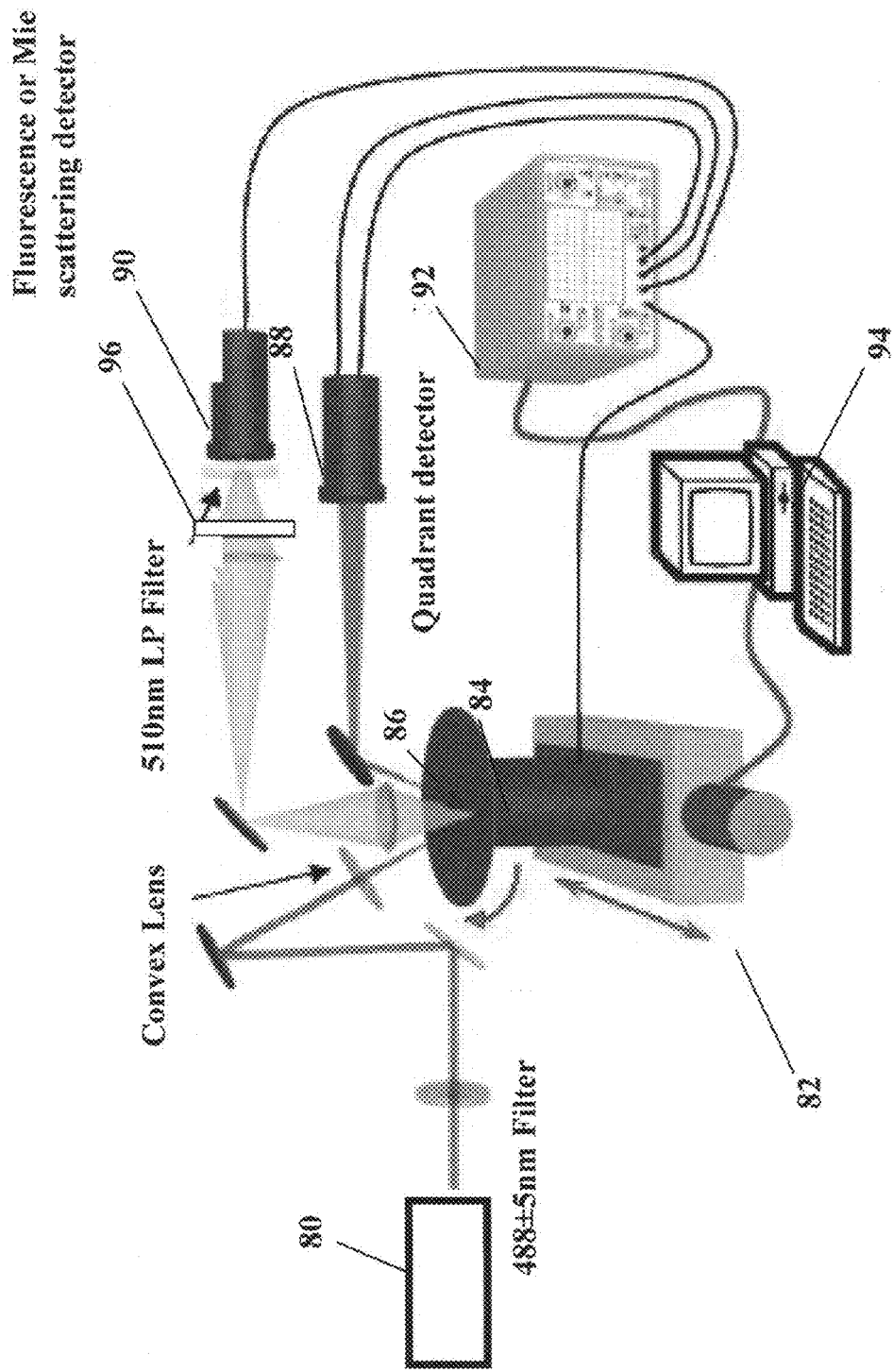
FIG. 14 illustrates schematically an embodiment of a four-channel microarray detection system that is capable of simultaneously acquiring four different signals from protein molecules on a biological compact disk, including fluorescence and Mie scattering channels (detected by a high-amplification APD), and amplitude and phase-contrast channels (interferometric channels, detected by a quadrant photodiode)

One embodiment of a four-channel microarray detection system is shown schematically in FIG. 14. This system is capable of simultaneously acquiring four different signals from protein molecules on a biological compact disk. These four channels are: fluorescence and Mie scattering channel (detected by a high-amplification APD 90), amplitude and phase contrast channel (interferometric channels, detected by a quadrant photodiode 88). The embodiment illustrated in FIG. 14 comprises a laser 80 (Innova300, Coherent Inc.), a linear stage 82 (MM2K, Newport), a spinning motor 84 (Scanner motor, Lincoln Laser, Inc.), a biological compact disk 86, a quadrant detector 88 (PC50-6, Pacific Silicon Sensor Inc.), an APD 90 (C5460-01, Hamamatsu Company), an oscilloscope 92, a computer 94 and optical components such as mirrors, filters and lenses. The system is now discussed with a focus on the following three categories: light path, scanning mechanism, and electronics.

To map the entire disk, the scanning mechanism uses a polar coordinate system. The spin motor 84, on which the biological compact disk 86 is mounted, provides the angular coordinates when the motor 84 spins in a selectable frequency ranging from 20 Hz to 80 Hz. A linear stage 82 provides the radial coordinate. In the experimental embodiment, the linear stage 82 can move back and forth with 0.1 um linear precision and 300 mm maximum travel distance. The spin motor 84 is fixed on the linear stage 82 so that two-dimensional mapping can be realized with appropriate control by the computer 94. This system is capable of mapping a 100 mm diameter of the biological compact disk in 30 minutes with 2 um by 2 um pixel resolution.

The illumination laser light emitted by the laser 80 has a wavelength of 488 nm. The laser beam is steered and focused onto the surface of the biological compact disk 86 with a filter, several mirrors and one 10 cm convex lens. The radius of the focal spot is about 20 um on the disk 86. Higher resolution can be achieved by switching the 10 cm lens with a short focal-length lens or a microscope objective lens. The reflected light is guided into the quadrant detector 88 which is responsible for acquiring the interferometric signals (amplitude and phase contrast channels). A 4 cm convex lens above the biological compact disk 86 gathers fluorescence or Mie scattering radiation and sends it to the APD 90. A 510 nm long-pass optical filter 96 effectively blocks the scattered laser light for fluorescence detection. The long-pass optical filter 96 is removed from the optical path for detection of the Mie scattering signal with this channel.

The oscilloscope 92 acquires waveforms for each scan track. The APD 90 and the quadrant detector 88 are input into three channels of the oscilloscope 92 by coaxial cables. Two cables are connected to the quadrant detector 88 to acquire the two types of interferometric signals (i.e., amplitude and phase contrast). One cable is connected to the APD 90 to sequentially acquire the fluorescence signal and the Mie scattering signal depending on whether the long pass filter 96 is in the optical path. One more coaxial cable connects the stage 82 to the oscilloscope 92 for the stage 82 to send a trigger signal to the oscilloscope 92. The computer 94 controls the linear stage 82 and records data from the channels of the oscilloscope 92.

This system has been tested with Gel-printed protein grating patterns and spotted patterns of antibodies. The former provide a periodic signal for system calibration and signal power spectrum analysis. The latter shows the system detection for immunological assays.

In the gel-printed protein patterns, the protein molecules are immobilized by physical adsorption following hydrophobic activation of the silicon dioxide surface of the disk by silanization (disks soak in 0.02M chlorooctadecylsilane toluene solution for 12 hours). Proteins bind with the silanized disk surface through hydrophobic interaction. Bovine serum albumin (BSA) conjugated with fluorescein (A9771, Sigma Corp.) is printed on the disk in a grating pattern with a gel stamp method. Each protein stripe width is 100 um, and the gap between two stripes is 120 um. After printing, the disk surface is rinsed with deionized water then blown dry with purified nitrogen. Because the protein is conjugated with fluorescein (absorption wavelength of 492 nm), the four-channel system is able to image the protein pattern in both the fluorescence and the interferometric channels.

FIG. 15 shows the signals collected from the four channels with this biological compact disk. On the same region of the protein grating pattern, whose thickness is about 1~4 nm (approx. a monolayer), imaging is simultaneously performed with the four channels. FIG. 15A shows the fluorescence signal captured by the APD 90. FIG. 15B shows the Mie scattering signal captured by the APD 90. FIG. 15C shows the amplitude signal captured by the quadrant detector 88. FIG. 15D shows the phase contrast signal captured by the quadrant detector 88.

Figure 15A:
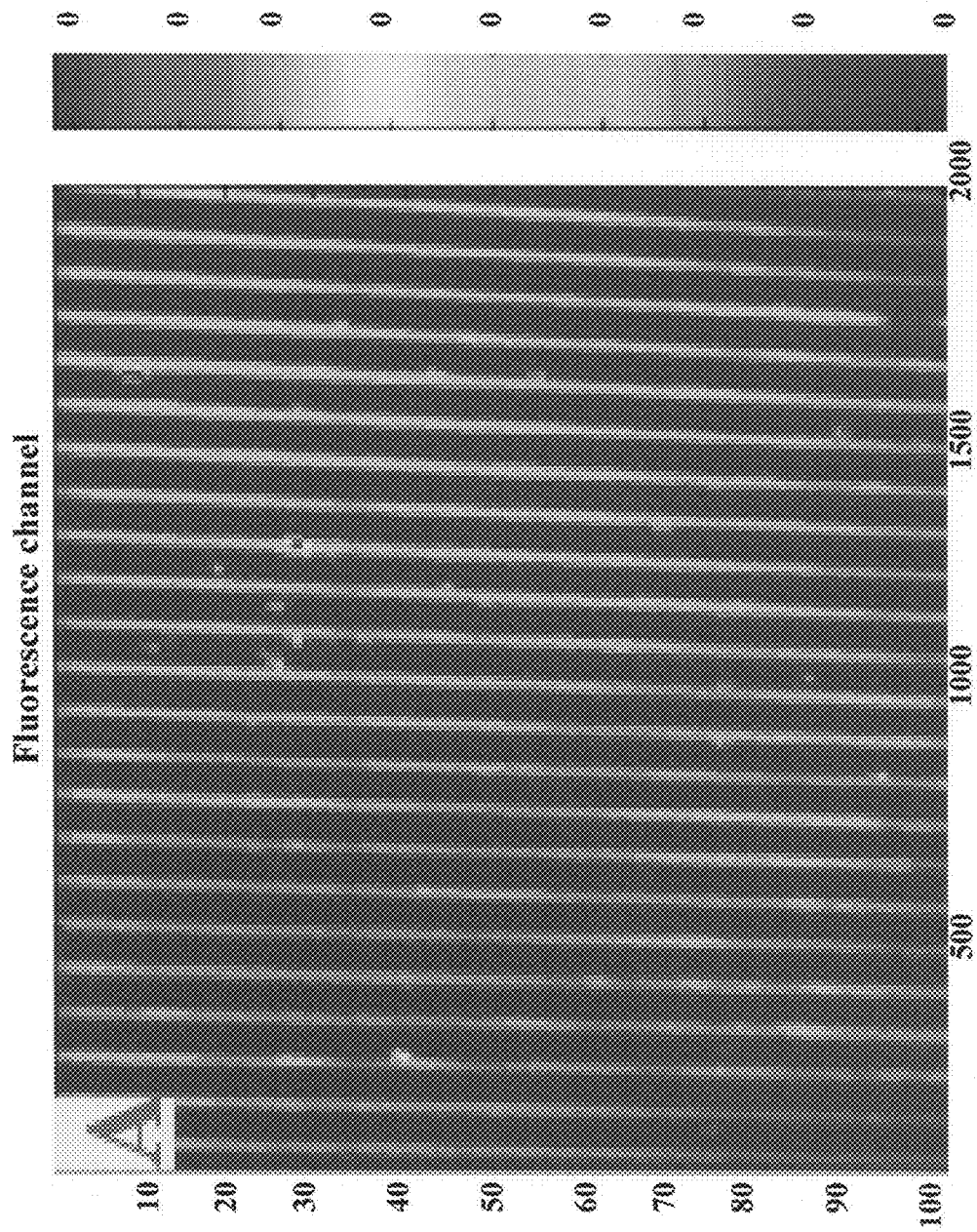
FIG. 15 shows biological compact disk images with fluorescence and interferometric methods, the images were simultaneously captured with 4 channels: (A) Fluorescence; (B) Mie scattering; (C) Amplitude and (D) Phase contrast, on the same region of a protein grating pattern with a thickness of about 1~4 nm (approx. a monolayer) that was illuminated at 488 nm.
Figure 15B:
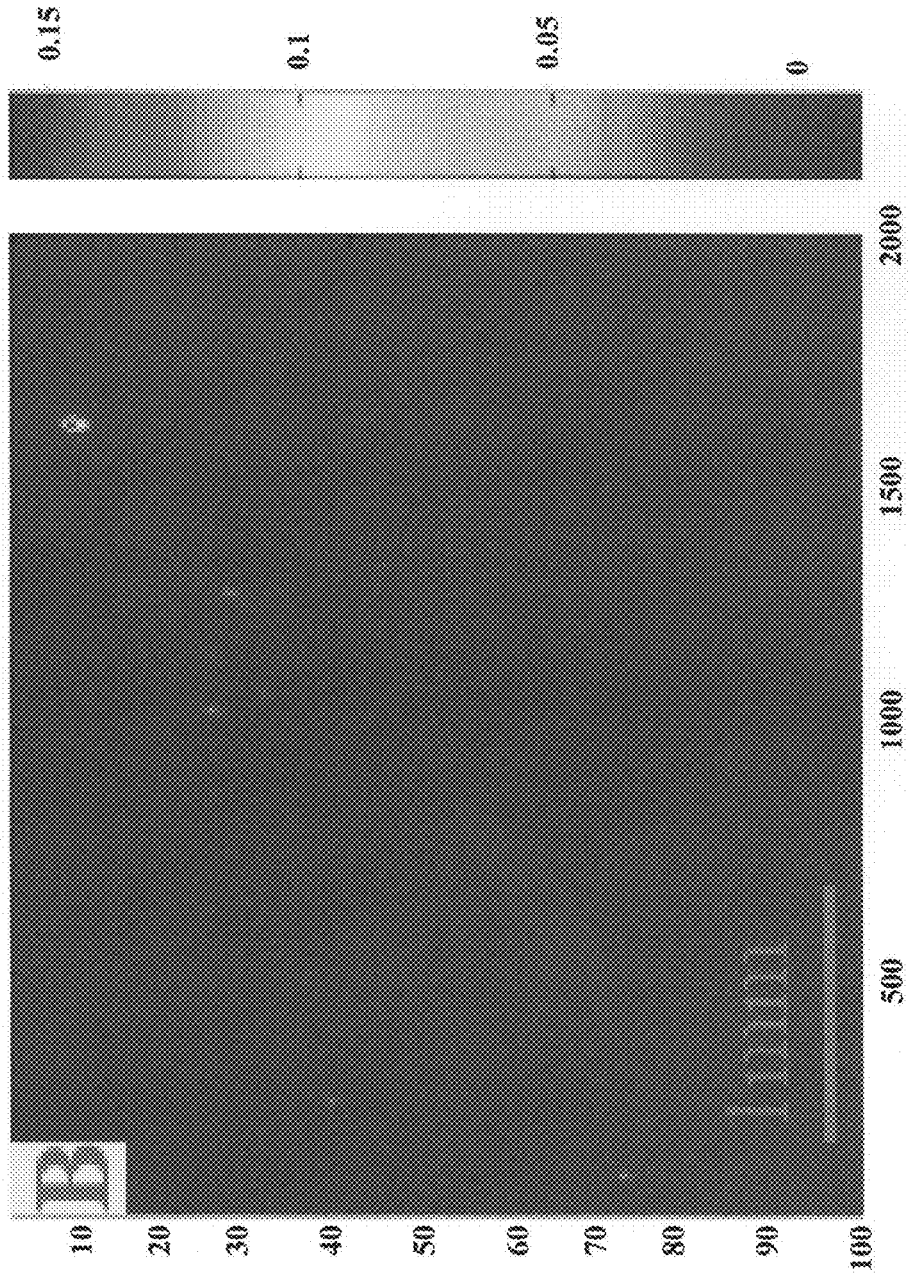
Figure 15C:
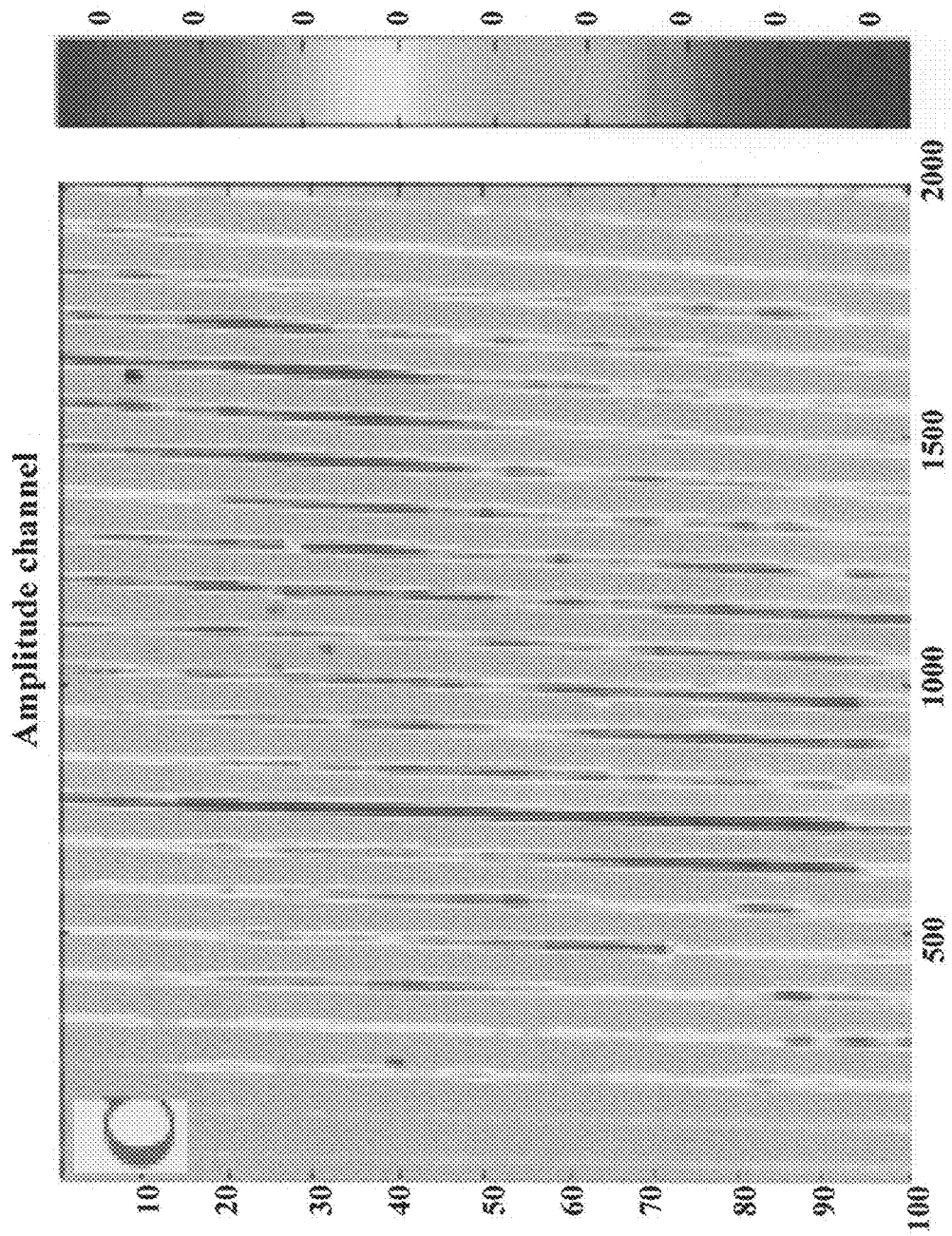
Figure 15D:
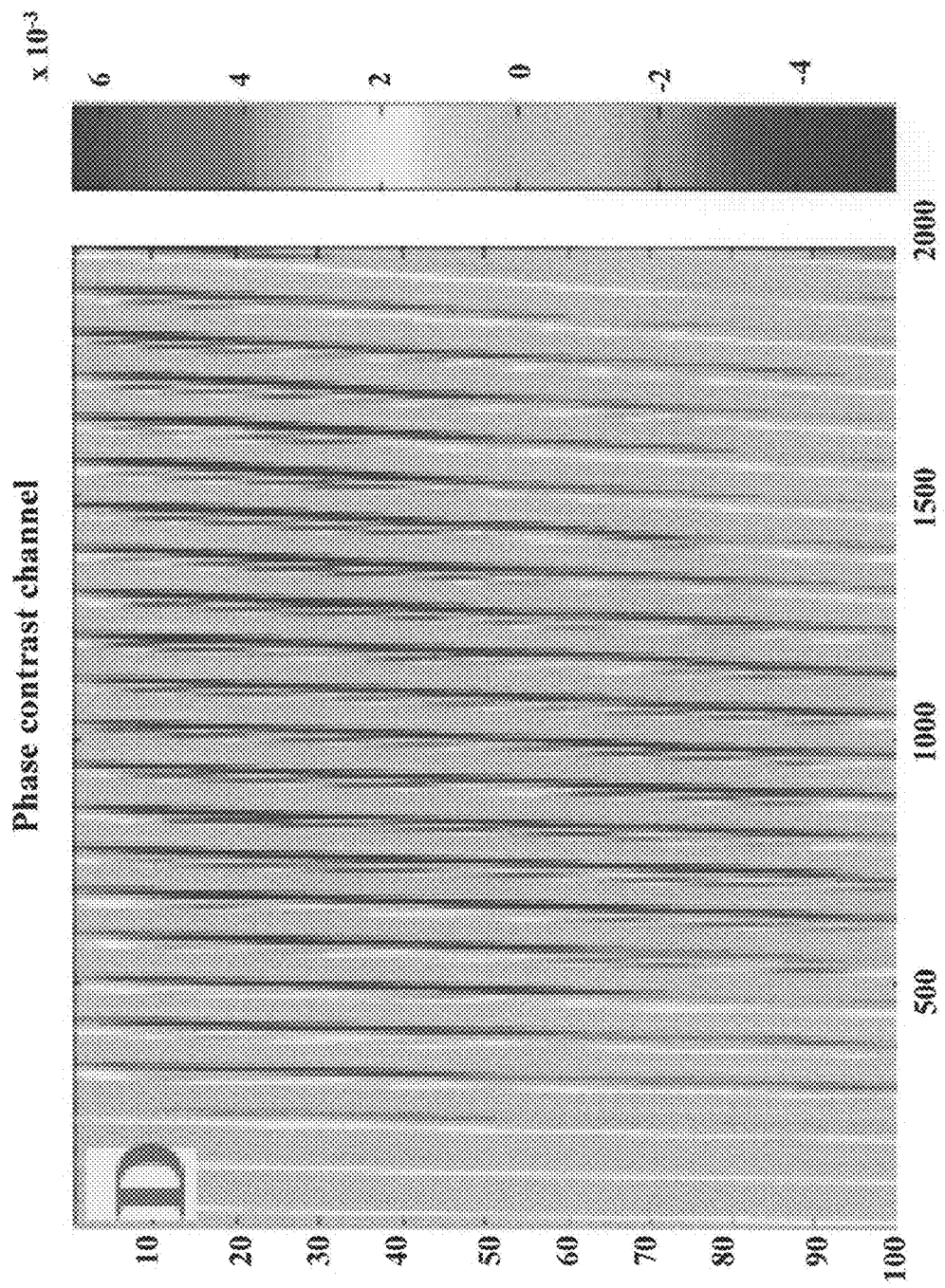

The data in FIGS. 15A, 15C, and 15D show strong signals from the patterned protein, while the Mie scattering data in FIG. 15B is virtually blank. This means that protein molecules are printed evenly and did not agglomerate. However in other experiments, strong Mie scattering has been observed in this channel. Upon observing the Mie scattering data more carefully, a "stain" was found near the top-right corner which could be due to a dust particle or agglomerated protein. The cross-correlation value is 0.83 between the fluorescence channel in FIG. 15A and the amplitude interferometry channel in FIG. 15C, demonstrating that the fluorescence and amplitude channels are highly correlated, although not identical, with the differences caused by differences between specific and nonspecific mass binding, and also caused by differences in fluorophore microenvironments on the disc.

Figure 16A:
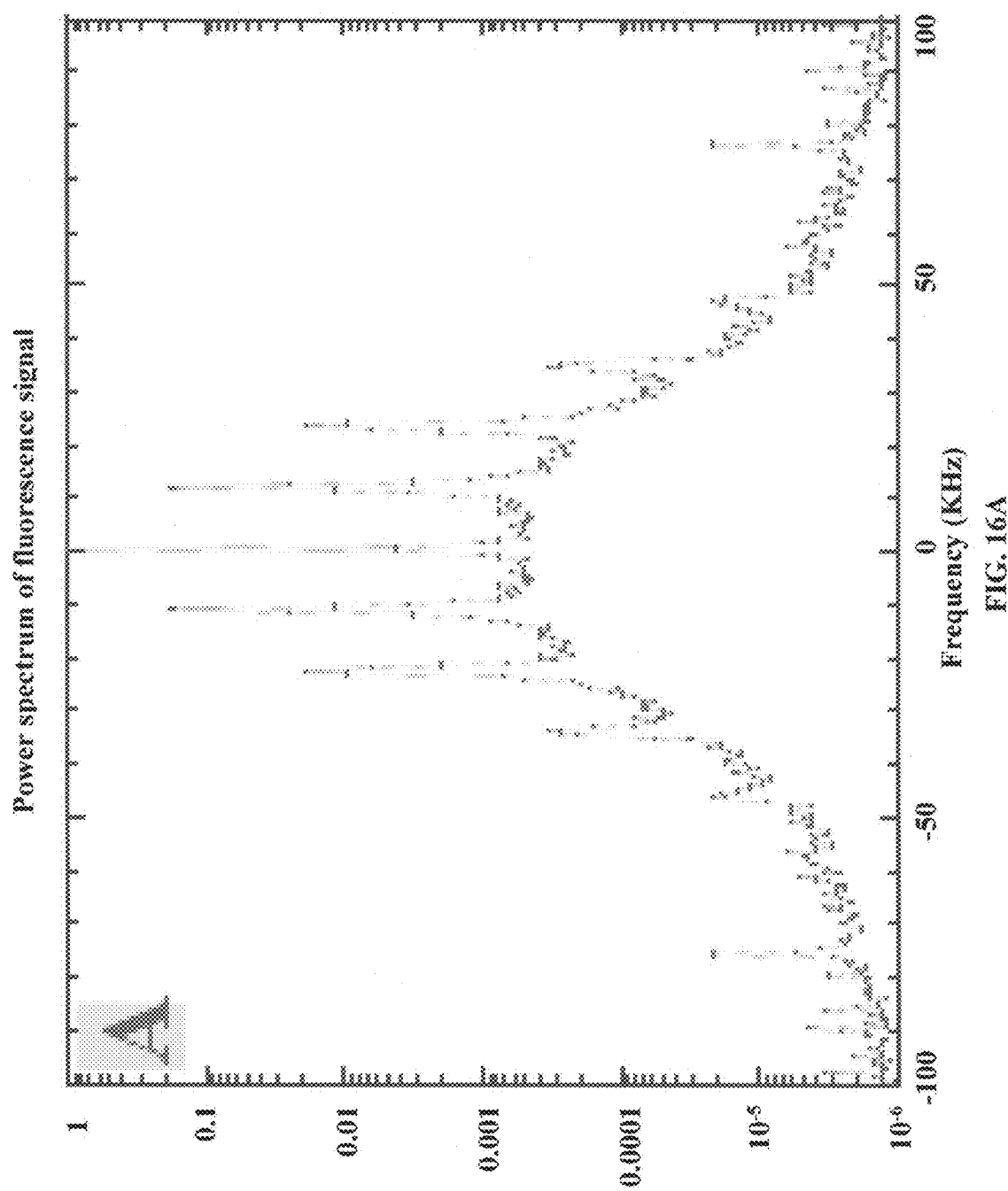
FIG. 16 shows the power spectra for the images shown in FIG. 15: (A) Fluorescence; (B) Mie scattering; (C) Amplitude and (D) Phase contrast channels.
Figure 16C:
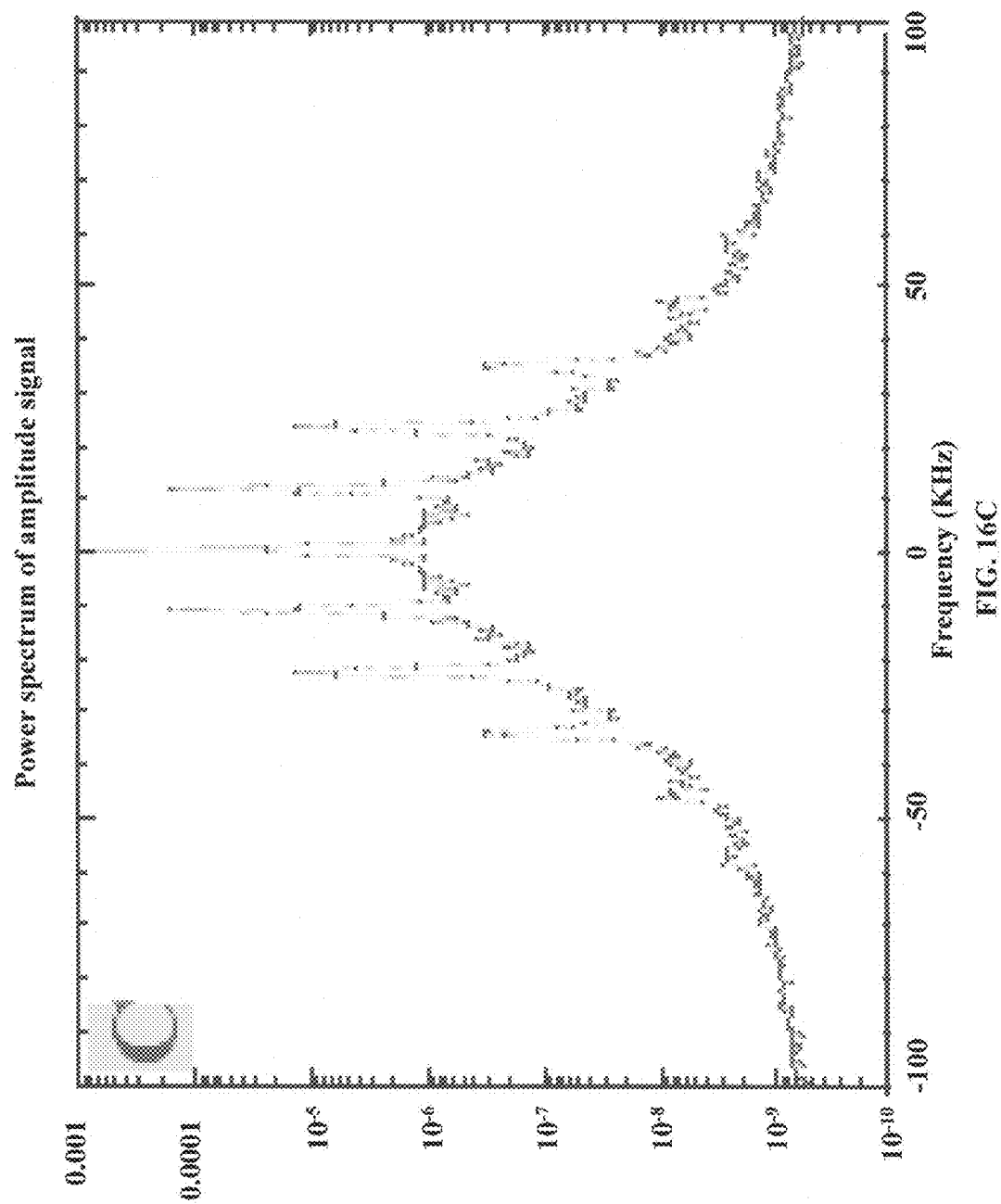

FIGS. 16A-D show the power spectra corresponding to the data in FIGS. 15A-D, respectively. The power spectra for fluorescence is shown in FIG. 16A; the power spectrum for Mie scattering is shown in FIG. 16B; the power spectrum for the amplitude interferometric channel is shown in FIG. 16C, and the power spectrum for the phase contrast interferometric channel is shown in FIG. 16D. The family of peaks in the spectra comes from the periodic protein stripe pattern. The signal-to-background ratio (SBR) for the power spectra in FIGS. 16A, 16B, 16C and 16D are respectively: 532:1, 1:1, 617:1, and 98:1. The amplitude channel and the fluorescence have similar SBR values, indicating that the sensitivities are almost equal in these cases. The phase-contrast channel SBR is relatively low but still considered strong. The thickness of the protein layer is 1~3 nm in this experiment. The detection limit for the lowest detectable protein density is estimated to be 2~6 pm, or about 2~6 pg/mm$^2$ areal density.

In the power spectra graphs of FIG. 16, the first-order signal frequency is almost at the top of the spectrum shoulder, which arises from the 1/f noise of the system combined with surface roughness of the disc. This indicates that the target signal may not be separated from the 1/f noise frequency domain in this experiment. This is because of the low spin frequency of the motor 84, about 20 Hz, and the relatively large distance between the protein stripes. By scanning on smaller protein patterns, such as submillimeter spots, with 80 Hz spinning frequency the SBR can be improved by more than a factor of 10 which extends the detection sensitivity to 0.2~0.6 pg/mm$^2$.

It is important to note that 1/f noise is not equivalent to surface roughness. Noise is stochastic and changes from circuit to circuit of the disc. In contrast, surface roughness is a fixed property of the disc and can be measured with the high accuracy of the interferometric metrology. Therefore, this surface roughness is not noise, but can be measured accurately and subtracted accurately between a pre- and a postscan that seeks to measure the amount of bound protein. It is when the surface is measured accurately and subtracted that the sensitivity of this technique achieves low values such as 0.2 to 0.6 pg/mm$^2$.

This embodiment of an integrated protein microarray detection system, can perform fluorescence, interferometry and Mie scattering simultaneously on a protein-patterned biological compact disk. Biological compact disk structures optimized for each channel were fabricated and tested with periodic protein patterns. The results show that both interferometric and fluorescence channels can achieve a 5 pg/mm$^2$ detection limit. The immunoassay experiment showed the four-channel system potential for immunoassays with high-concentration backgrounds. The system detected 10 ng/ml target protein in 7 mg/ml lysate.

Figure 17A:
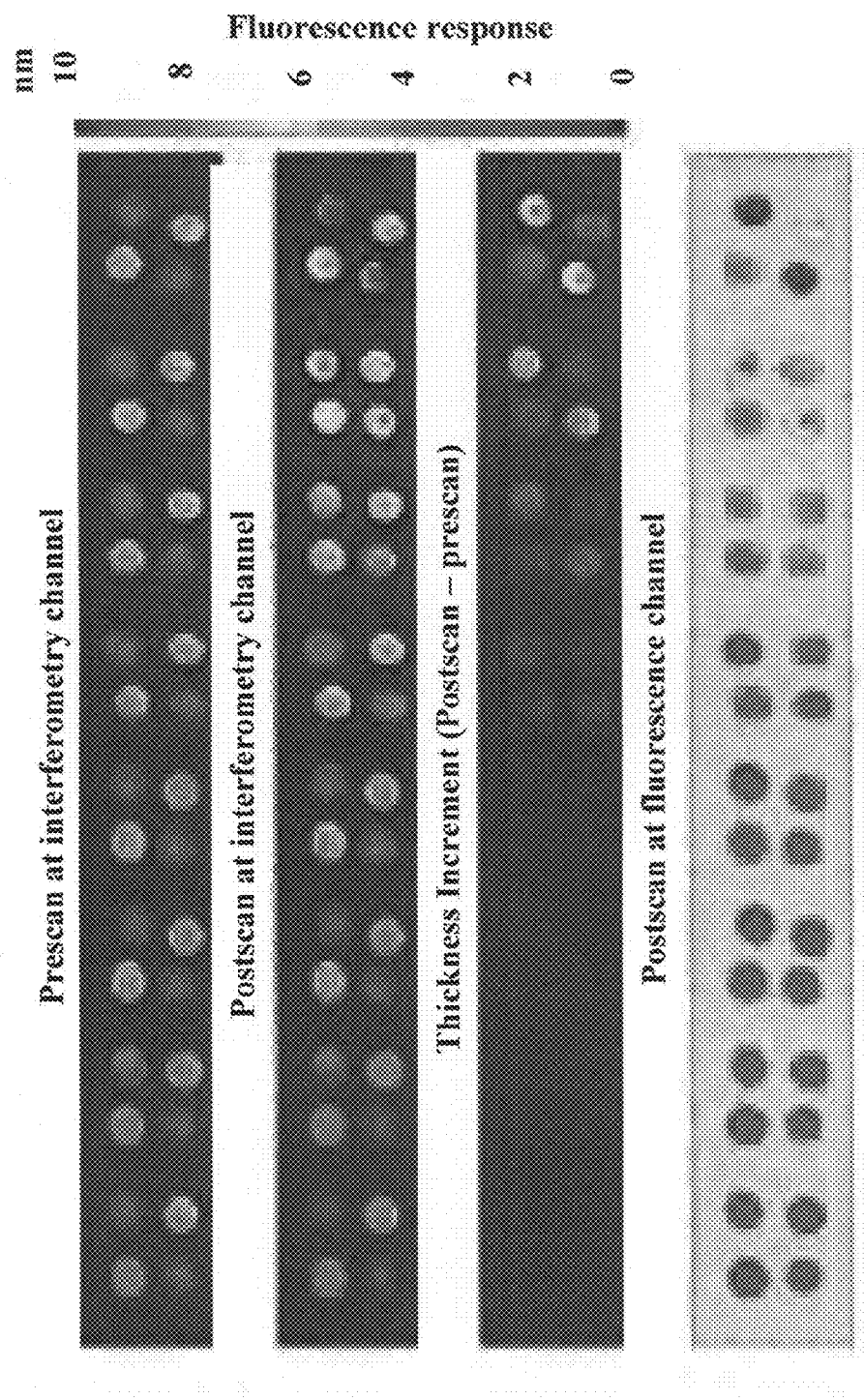
FIG. 17A shows the spot intensities from the interferometry and fluorescence channels.
Figure 17B:
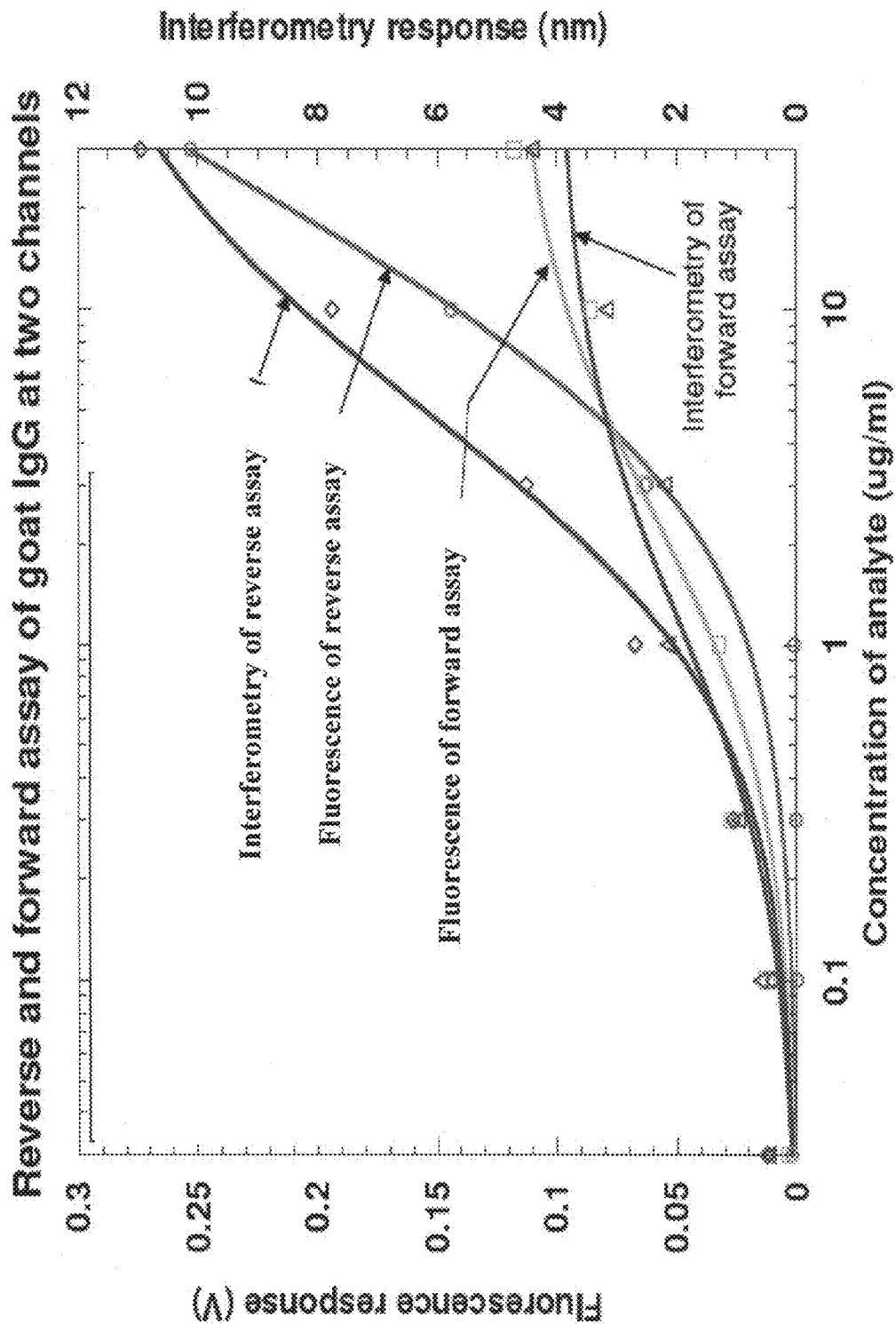
FIG. 17B shows the response curves for both the forward and reverse assays.
Figure 18A:
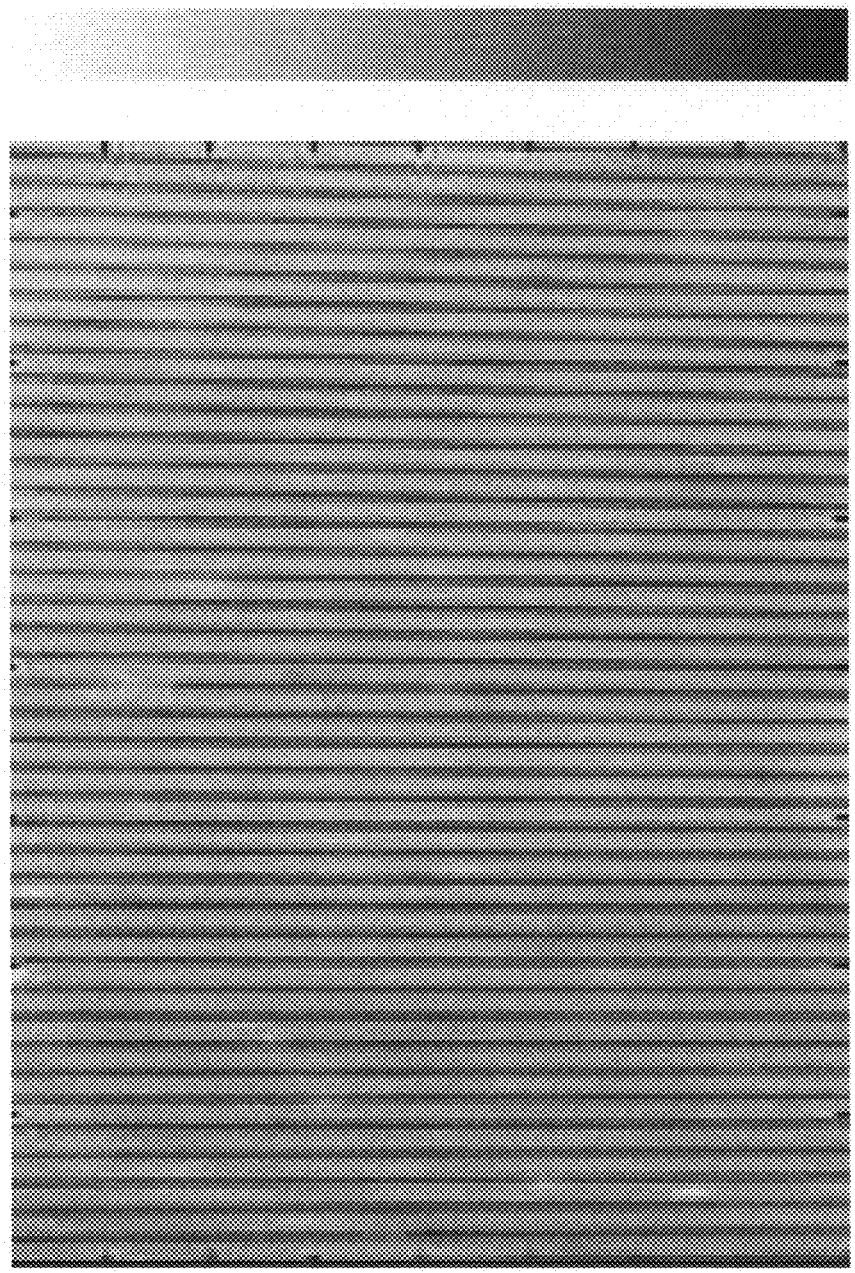
FIG. 18A shows the fluorescence channel for a two-channel acquisition of backfilled protein stripes at a concentration of 10 ug/ml collected simultaneously with the interferometry channel shown in FIG. 18B.
Figure 18B:
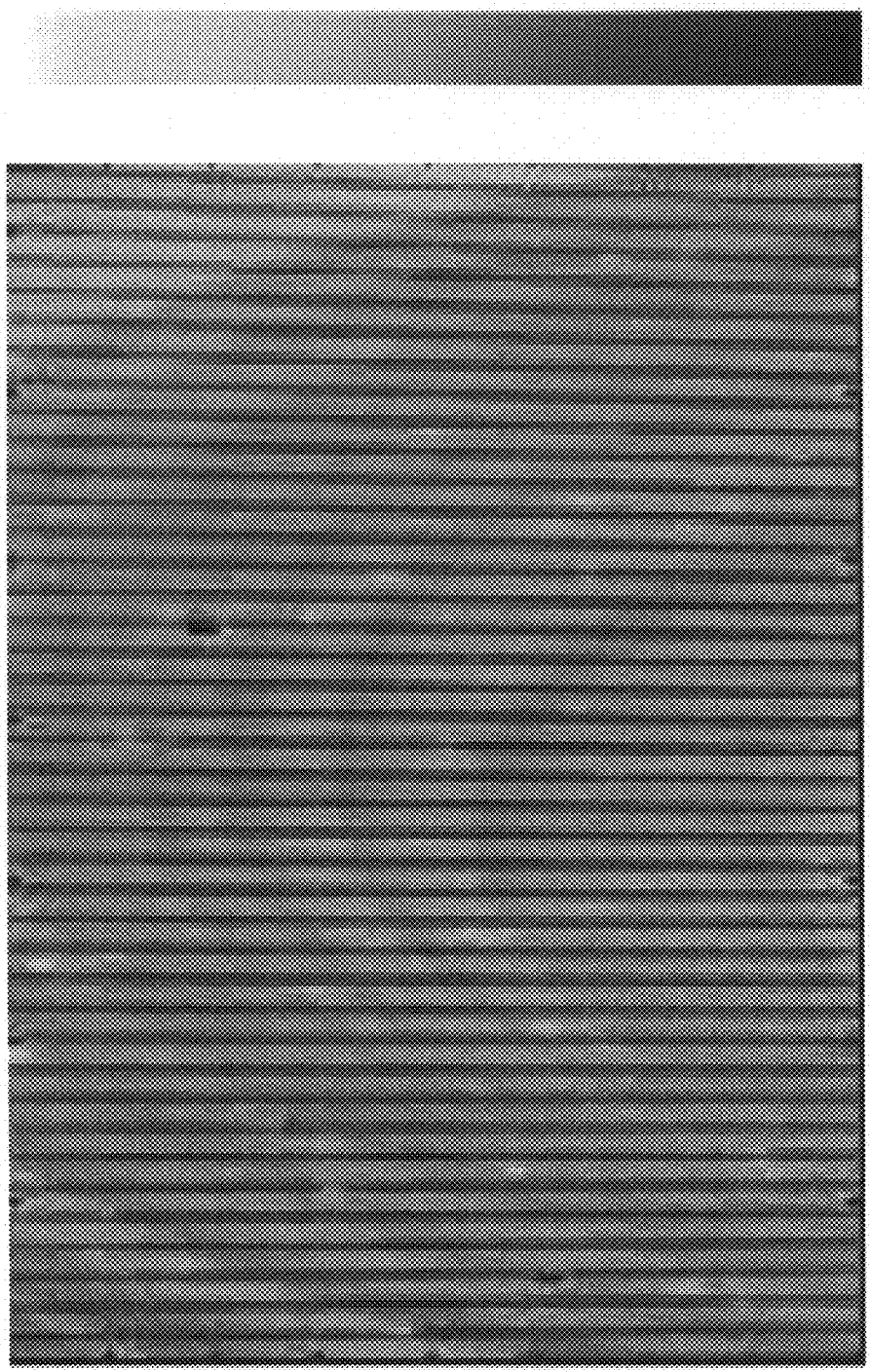
FIG. 18B shows the interferometry channel for a two-channel acquisition of backfilled protein stripes at a concentration of 10 ug/ml collected simultaneously with the fluorescence channel shown in FIG. 18A.
Figure 18C:
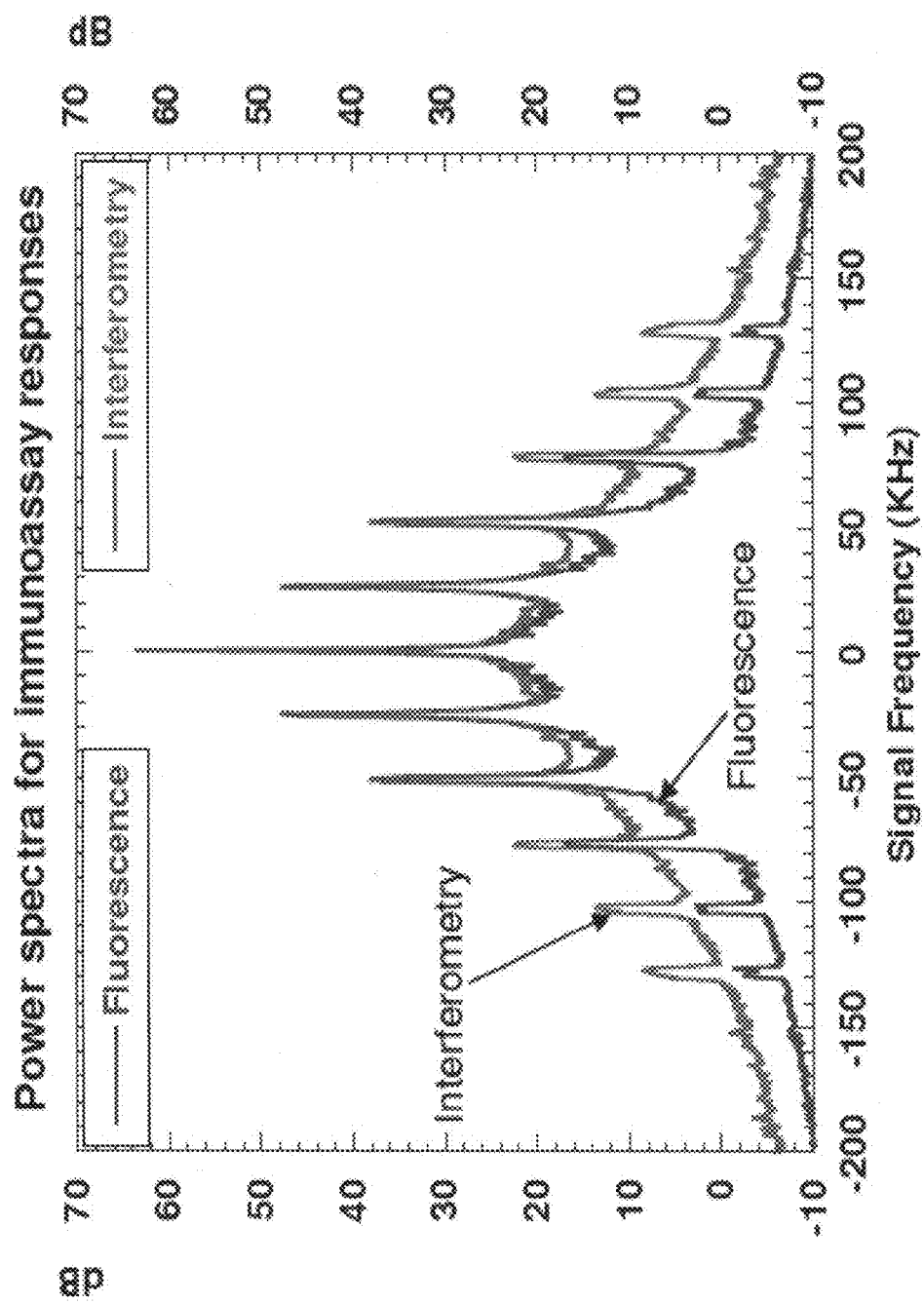
FIG. 18C shows the associated power spectra for the interferometry and fluorescence channel responses shown in FIGS. 18A and 18B.
Figure 18D:
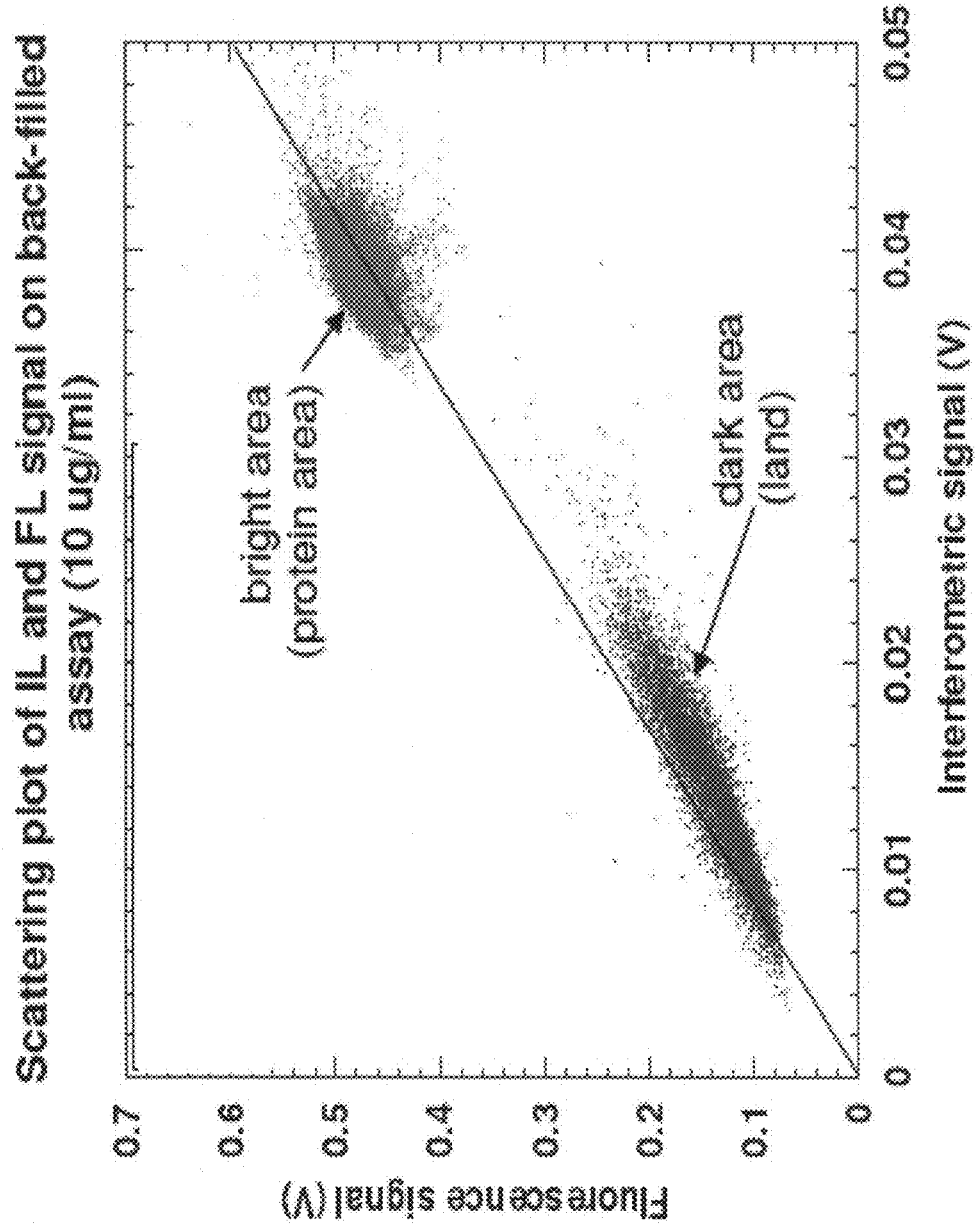
FIG. 18D shows the correlation between the interferometry and fluorescence channel responses shown in FIGS. 18A and 18B.

In another embodiment we explore the difference between a forward and a reverse assay. Fluorescence compared to interferometry shows important differences in this comparison. This experiment is shown in FIG. 17. The unit cells in this case have anti-goat antibody printed on one diagonal to bind antigen from sample, while the opposite diagonal has printed rabbit antigen to capture antibody from sample. The sample consists of FITC-conjugated anti-rabbit cultured in goat. In a single incubation both a forward and a reverse assay can be evaluated in both the interferometric and the fluorescence channels on the two opposite diagonals. The incubations were made with increasing sample concentrations of 0, 0.03, 0.1, 0.3, 1, 3, 10, and 30 ug/ml. The spot intensities from the interferometry and fluorescence channels are shown in FIG. 17A. The response curves for both the forward and reverse assays are shown in FIG. 17B. It is clear from the response curves that the reverse assay has a much stronger response than the forward assay. This general trend is captured by both the interferometric and fluorescence channels. However, there are quantitative differences between interferometry and fluorescence that can highlight different mechanisms between forward and reverse assays.

To provide further calibration and correspondence between interferometry and fluorescence, a two-channel acquisition of backfilled protein stripes at a concentration of 10 ug/ml is shown in FIG. 18. The fluorescence channel is shown in FIG. 18A, and the interferometry channel is shown in FIG. 18B, with the associated power spectra in FIG. 18C. The correlation between the two channels is shown in FIG. 18D. There is clean separation between the bright and the dark stripes with strong correlation in the corresponding values. These data show strong cross-validation of the interferometry and fluorescence channels.

Figure 19A:
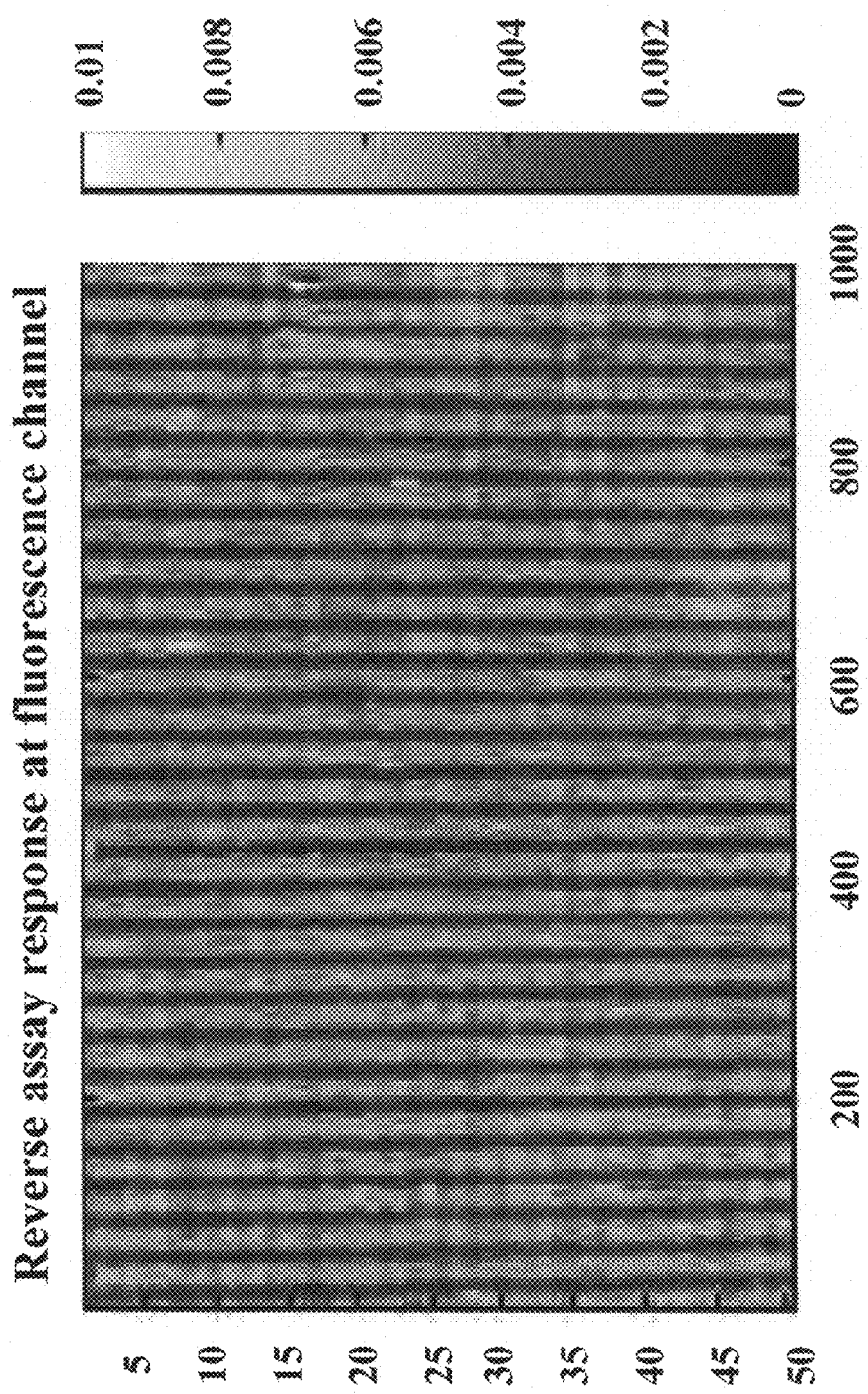
FIG. 19A shows the fluorescence channel for a two-channel acquisition of backfilled protein stripes at a concentration of 10 ng/ml collected simultaneously with the interferometry channel shown in FIG. 19B.
Figure 19B:
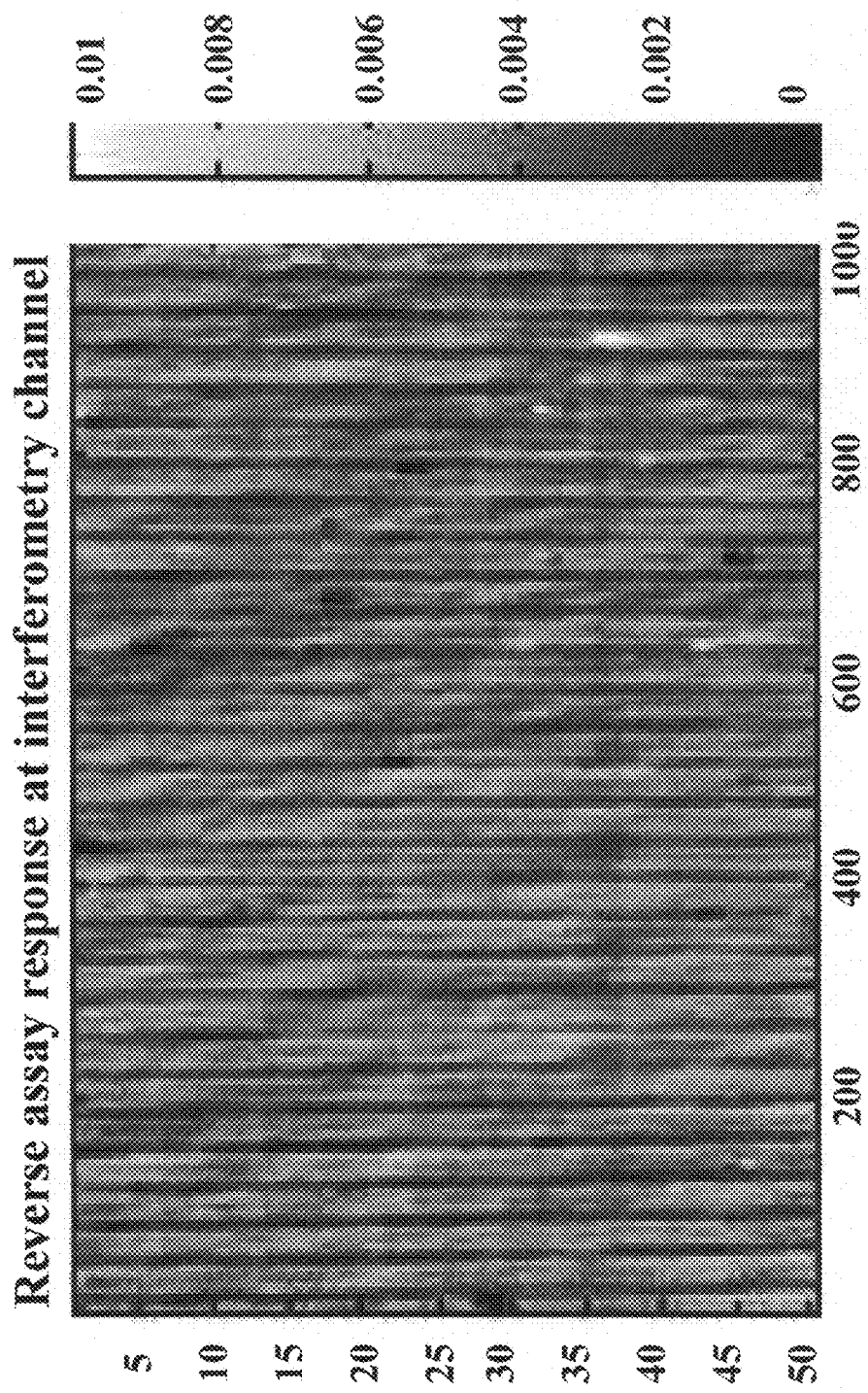
FIG. 19B shows the interferometry channel for a two-channel acquisition of backfilled protein stripes at a concentration of 10 ng/ml collected simultaneously with the fluorescence channel shown in FIG. 19A.
Figure 19C:
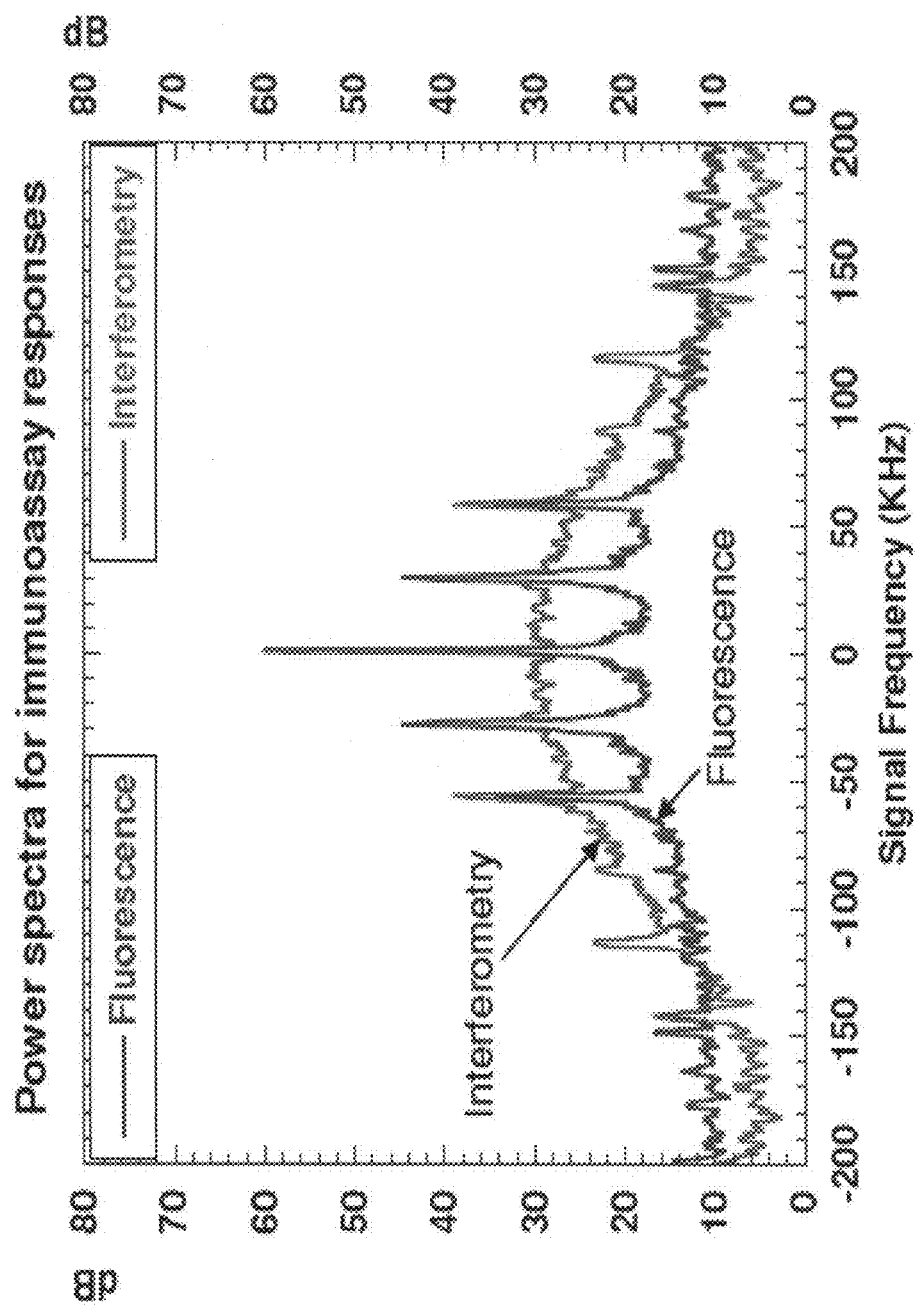
FIG. 19C shows the associated power spectra for the interferometry and fluorescence channel responses shown in FIGS. 19A and 19B.
Figure 19D:
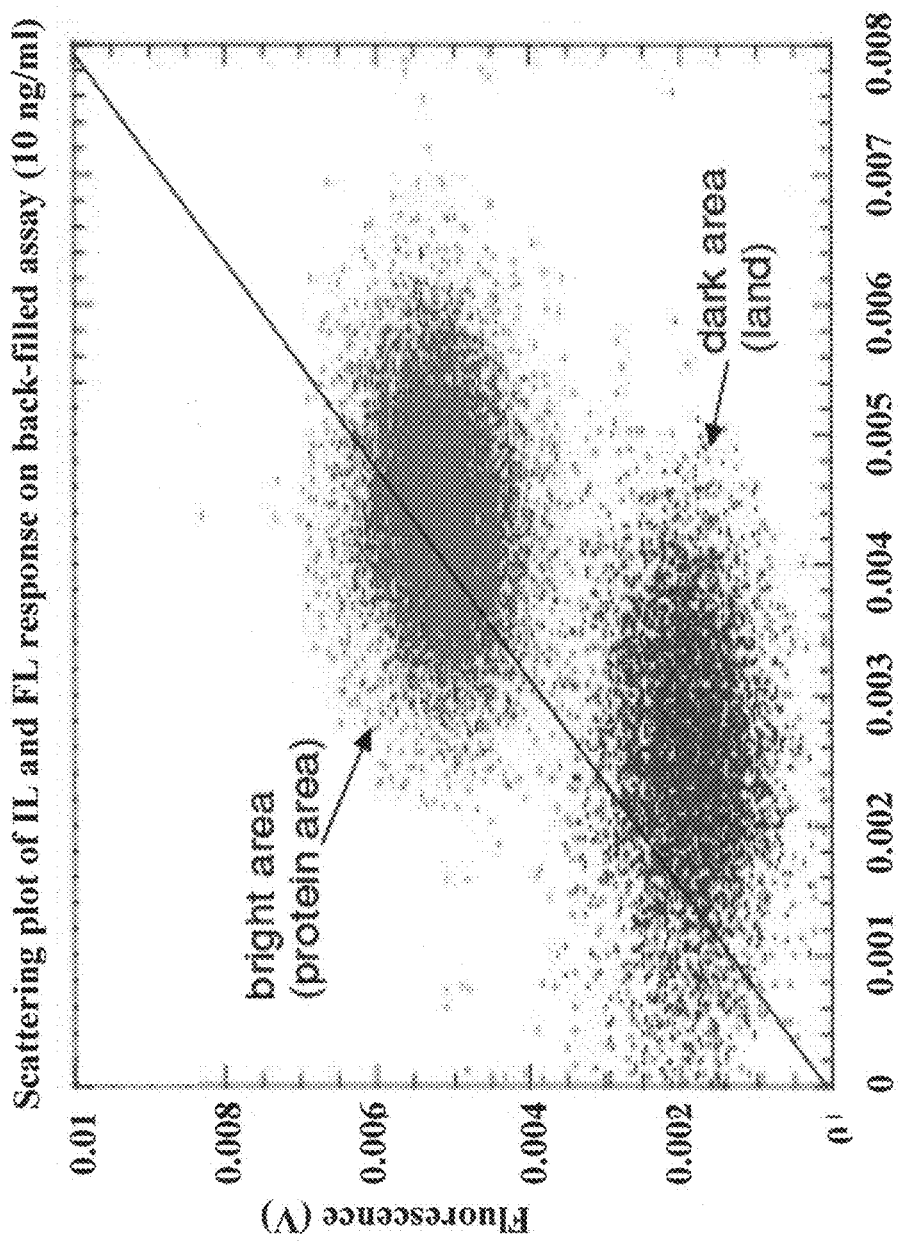
FIG. 19D shows the correlation between the interferometry and fluorescence channel responses shown in FIGS. 19A and 19B.

To test the detection limits, stripes were backfilled at a concentration of 10 ng/ml. The results are shown in FIG. 19. FIG. 19A shows the fluorescence channel, FIG. 19B shows the interferometric channel, FIG. 19C shows the corresponding power spectra, and FIG. 19D shows the correlation. There is still separation between the positive and negative stripes in the correlation. This concentration is near the detection limit for this approach that uses gel printing. Inhomogeneities in the gel printing technique limit the sensitivity.

Figure 20A:
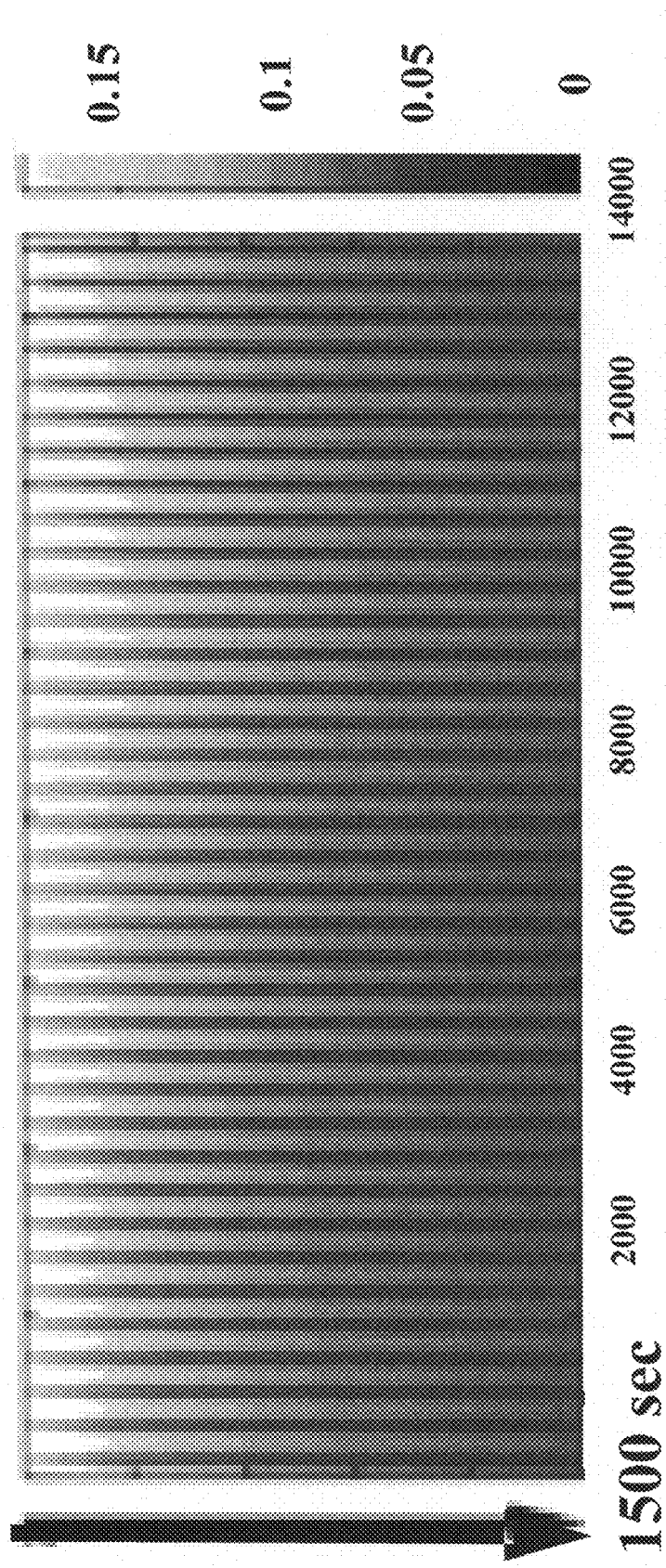
FIG. 20A shows the effects of bleaching on the fluorescence channel over time with the signal collected simultaneously with the interferometry channel shown in FIG. 20B.
Figure 20B:
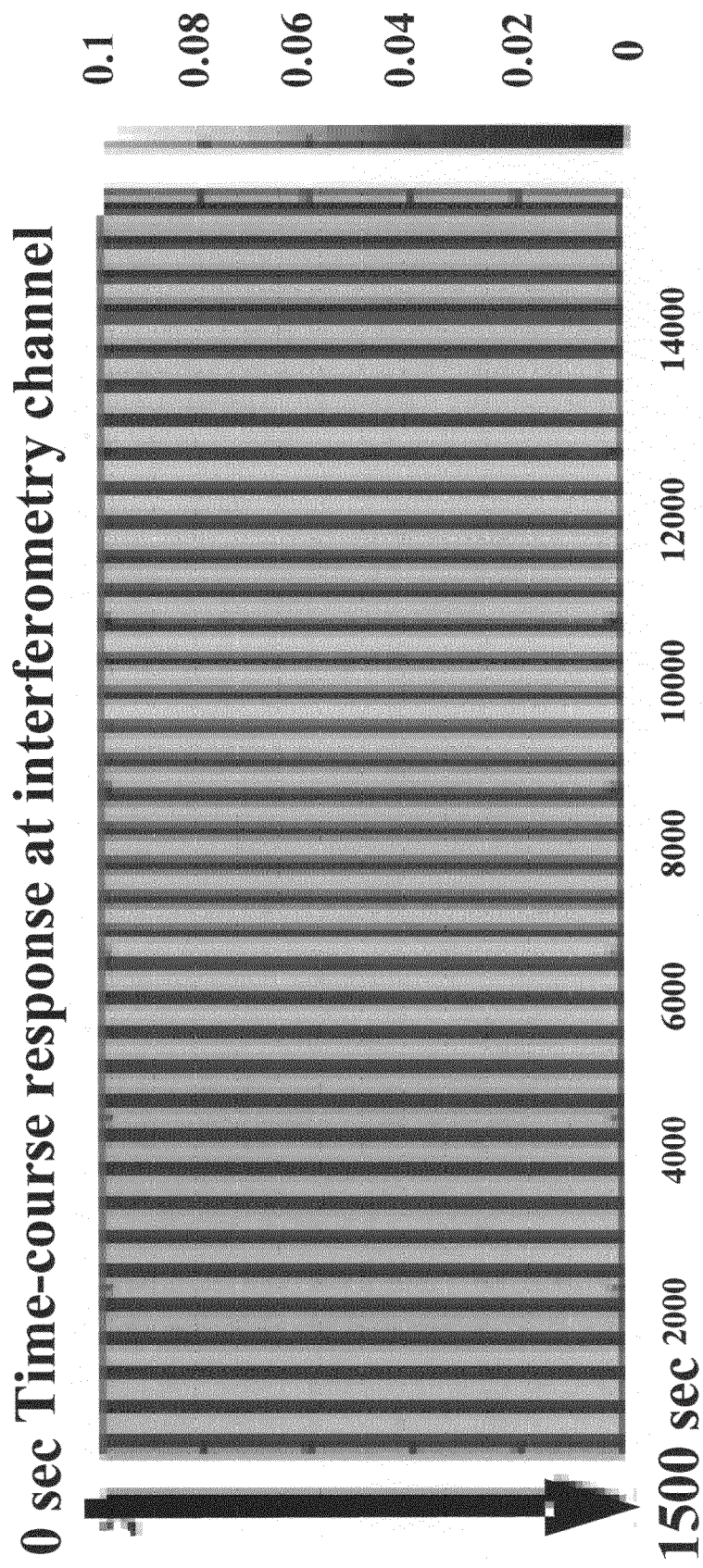
FIG. 20B shows the lack of bleaching effects on the interferometry channel over time with the signal collected simultaneously with the fluorescence channel shown in FIG. 20A.
Figure 20C:
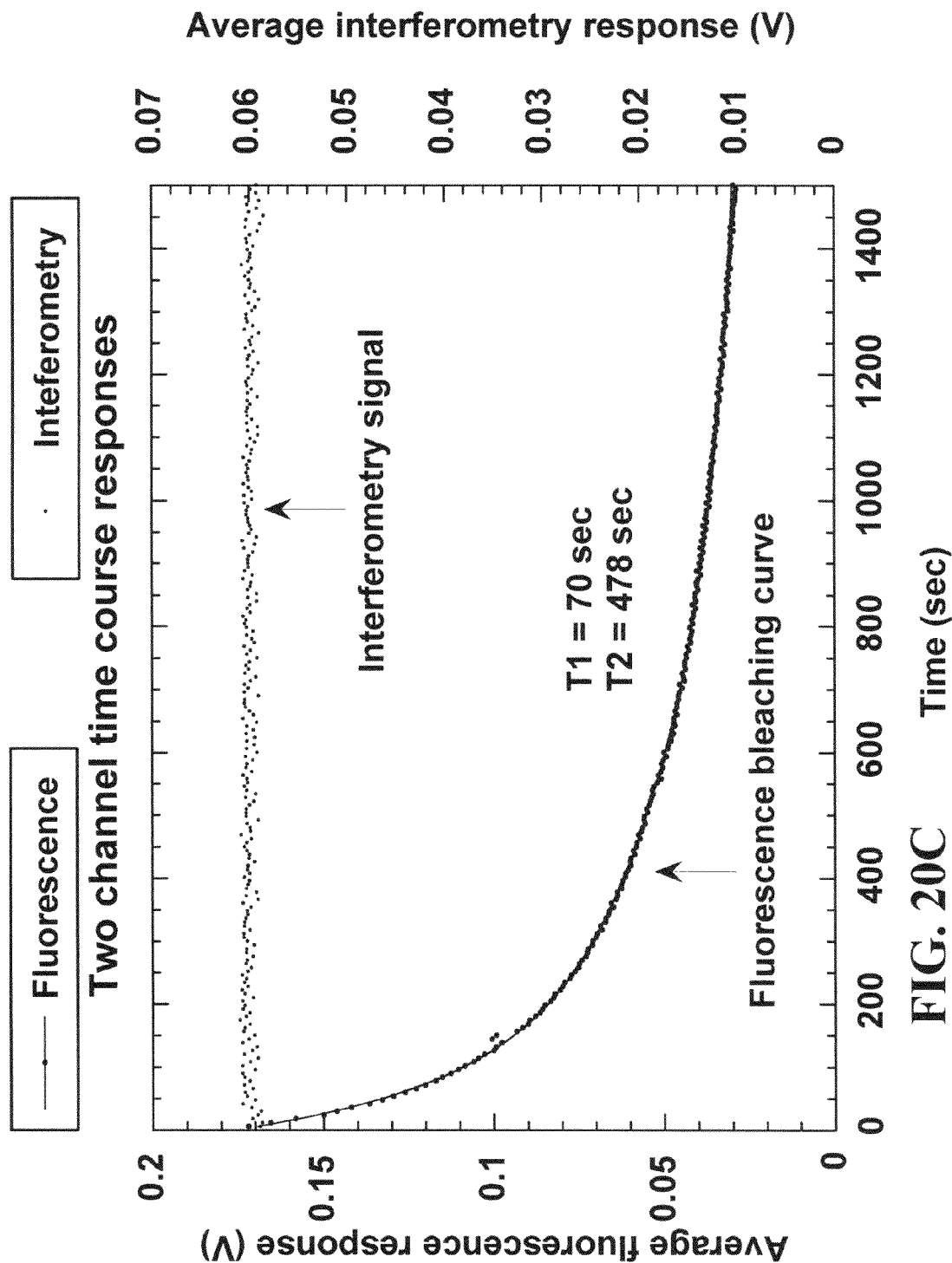
FIG. 20C is a graph of the average fluorescence and interferometry responses over time corresponding to the images shown in FIGS. 20A and 20B.

A key difference between interferometry and fluorescence is the quenching phenomenon that is associated with fluorescence but not with interferometry. One of the drawbacks of fluorescence is the destruction of the fluorophore, called bleaching, during illumination. To illustrate the power of the present multi-mode detection system, the bleaching of fluorescence was measured simultaneously in both an interferometric and a fluorescence channel. The results are shown in FIG. 20. FIG. 20A shows the fluorescence channel and FIG. 20B shows the interferometry channel. In this experiment the radius of the probe beam was not changed. The same track was measured repeatedly. During the scan, the fluorophore slowly quenched, seen in FIG. 20A with time increasing downward. However, in the interferometry channel seen in FIG. 20B there is no bleaching. This is seen in the graph in FIG. 20C. The interferometry channel is flat with time, while the fluorescence is bleached. This serves to illustrate fundamental differences between interferometry and fluorescence that the current invention exploits.

Figure 21:
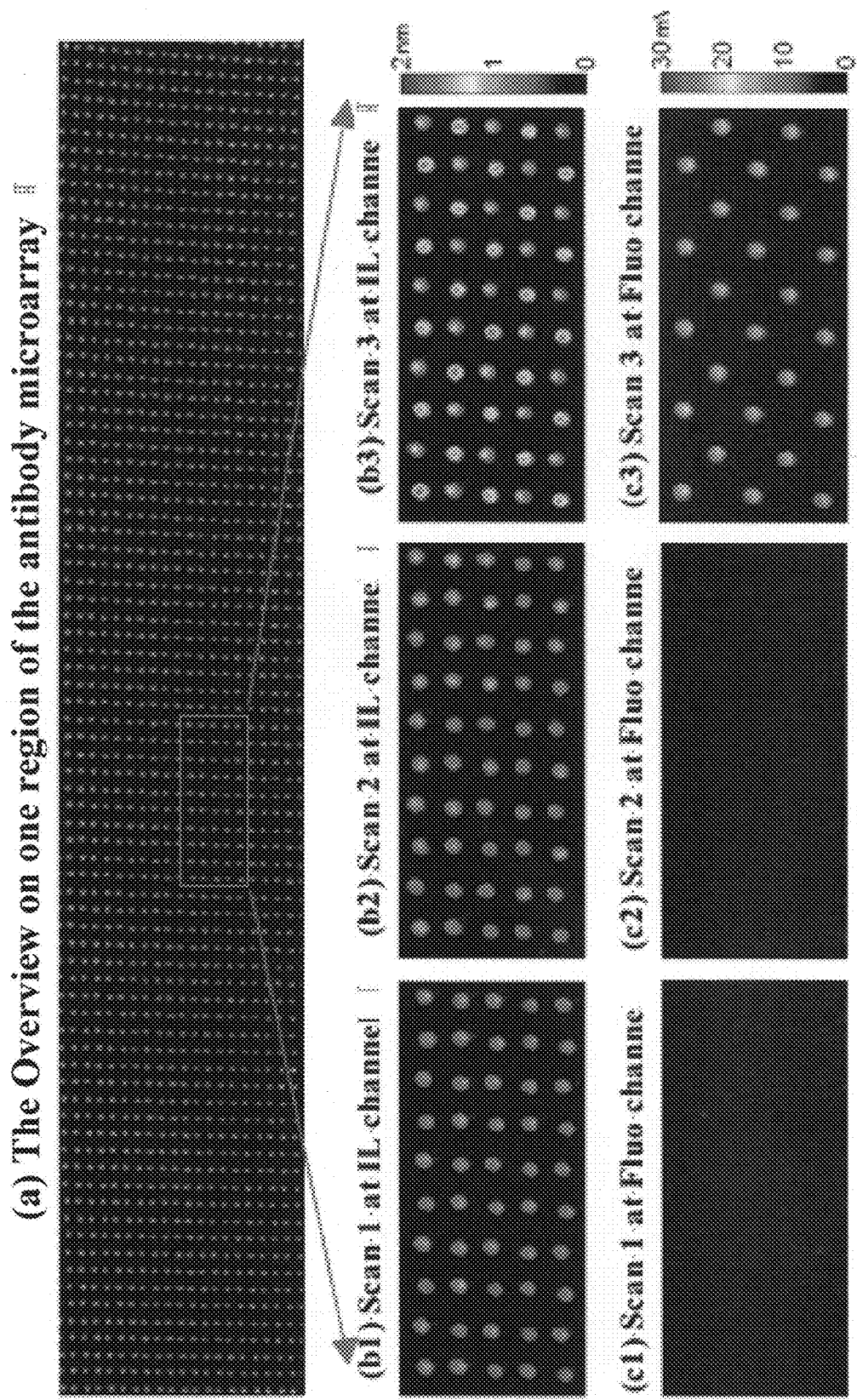

An extensive demonstration of dual fluorescence and inline interferometry is shown FIG. 21. In this example the disc was printed with 25,000 protein spots. Half were anti-rabbit and the other half were control spots. The disc was incubated with rabbit in a forward-phase assay, then followed with the sandwich that had a fluorescent tag. This demonstrates the differences between forward and sandwich assays in a microspot format. It also shows the use and comparison of the fluorescence channel to the interferometry channel. The second row of FIG. 21 is the interferometry channel, and the bottom row is the fluorescence channel. The fluorescence only appears in the final sandwich incubation.

On the disc, there were 3,400 antibody spots (anti-rabbit IgG, R2004, Sigma Company) and 3,400 control spots (anti-mouse IgG, R2004, Sigma Company) printed on one region of the biological compact disc (one disc can hold 50,000 spots). Each antibody spot is adjacent to one control spot. The spot diameter was 200 μm. FIG. 21a shows one part of the 6,800 spots. A two-channel scan (scan 1) was performed to record the initial thickness and fluorescence of these spots (see FIGS. 21b1 and c1, a small area of the microarray is shown for better viewing). The biological compact disc was incubated with 10 ng/ml rabbit IgG (I5006, Sigma Company) in PBST (PBS+0.05% Tween). Bovine serum at 100 μg/ml (B8655, Sigma Company) is spiked in the solution as background protein. A two-channel scan (scan 2) measured the interferometric and fluorescent signal change due to the antigen binding (see FIGS. 21b2 and c2). A secondary antibody formed sandwich assay to evaluate the two-channel detection limit. The biological compact disc is further incubated with 1 μg/ml anti-rabbit-FITC (F9887, Sigma Company) in PBST. A third scan (scan 3) measured the two-channel response due to the secondary antibody binding (see FIGS. 21b3 and c3).

Figure 22A:
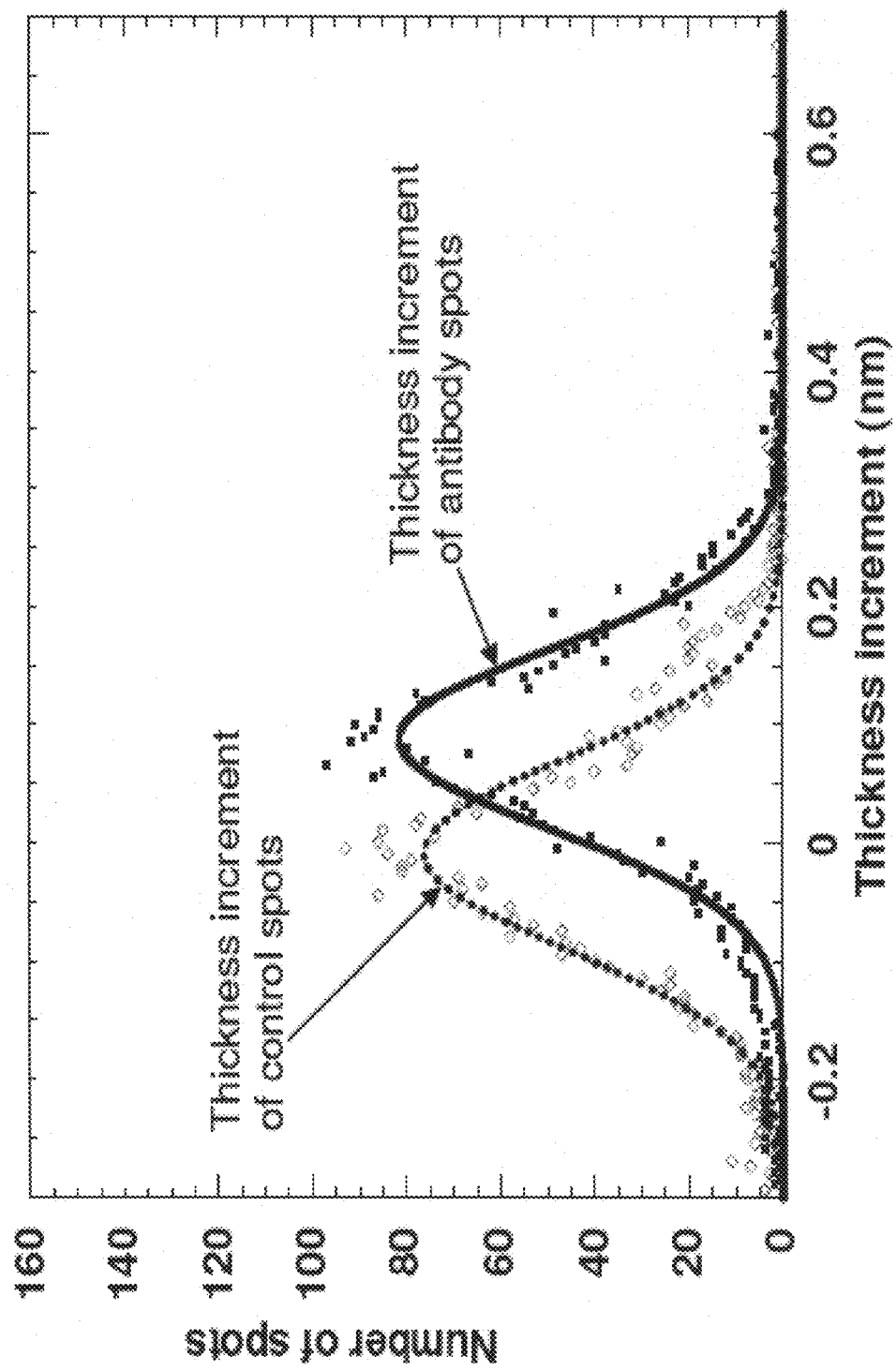
FIG. 22A shows distributions of the height increment of antibody and control spots after antigen binding.

In the analysis, the interferometric channel tracks the specific binding between anti-rabbit IgG and rabbit IgG. FIG. 22A shows the height increment of the antibody spots and control spots after incubation with 10 ng/ml rabbit IgG solution. In a histogram of the height increments of all spots, the centers of the specific and control Gaussian distributions are separated by a difference of 0.097 nm. The standard deviations of the two distributions are respectively 0.10 nm and 0.106 nm. So the standard errors are $0.10/\sqrt{3400}=0.0017$ nm and 0.0018 nm. If the antibody spot thickness increment is linear to antigen level at low concentration, the detection limit of interferometric channel is estimated as 250 pg/ml for the forward-phase assay. The fluorescence channel detects no signal at this stage because the antigen has no bound fluorophore.

Figure 22B:
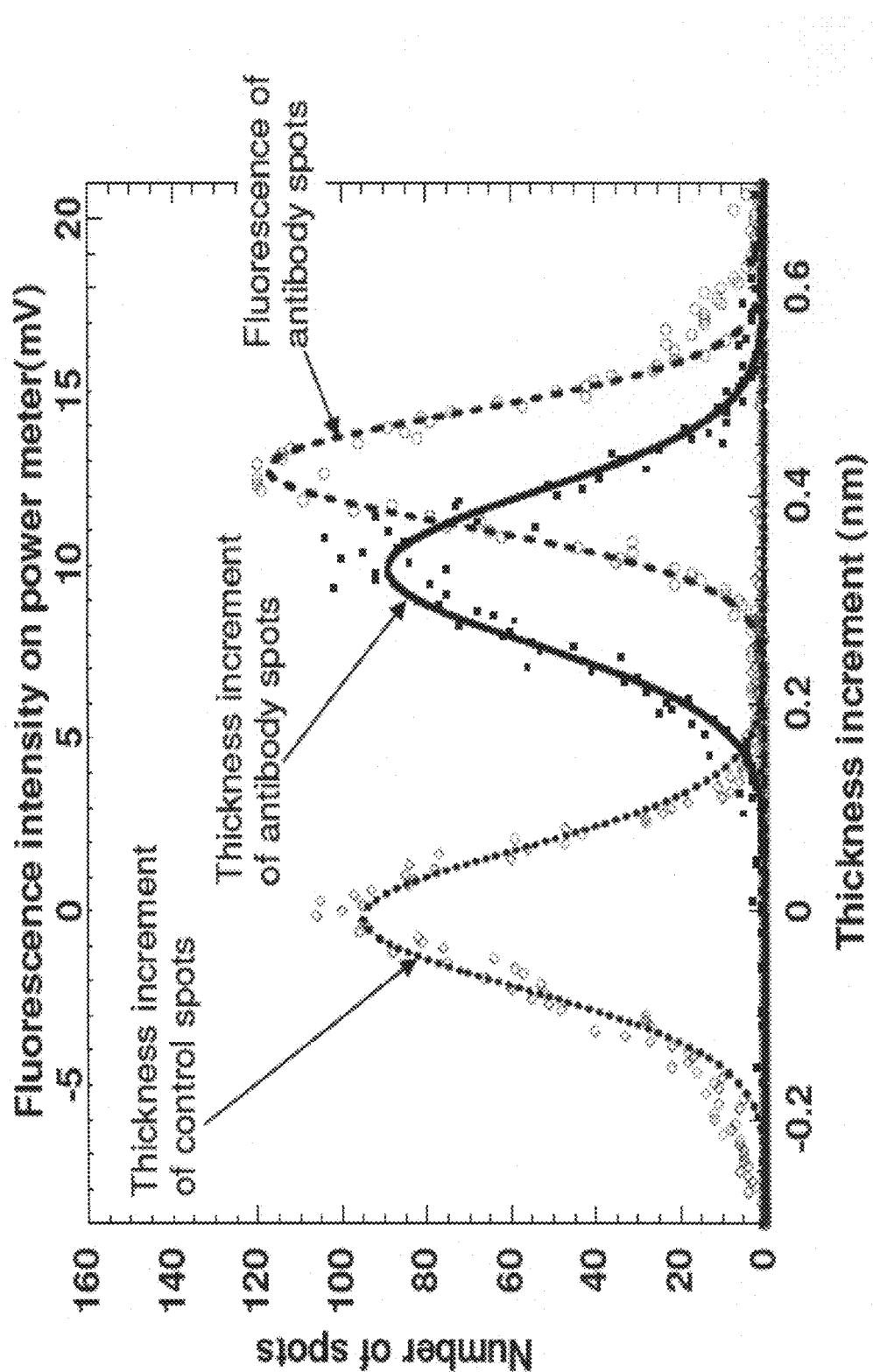
FIG. 22B shows distributions of the height increment of the antibody and control spots compared with the fluorescence signal of the antibody spots after secondary antibody binding.

FIG. 22B shows the height increment of the antibody and control spots compared with the fluorescence signal of the antibody spots after incubation with the anti-rabbit-FITC. The detection limit of the interferometric channel is estimated as 71 pg/ml. The detection limit is lower than forward-phase assay because one antigen can bind with several antibodies in the sandwich assay. The detection limit of the fluorescence channel is estimated as 31 pg/ml.

Figure 23:
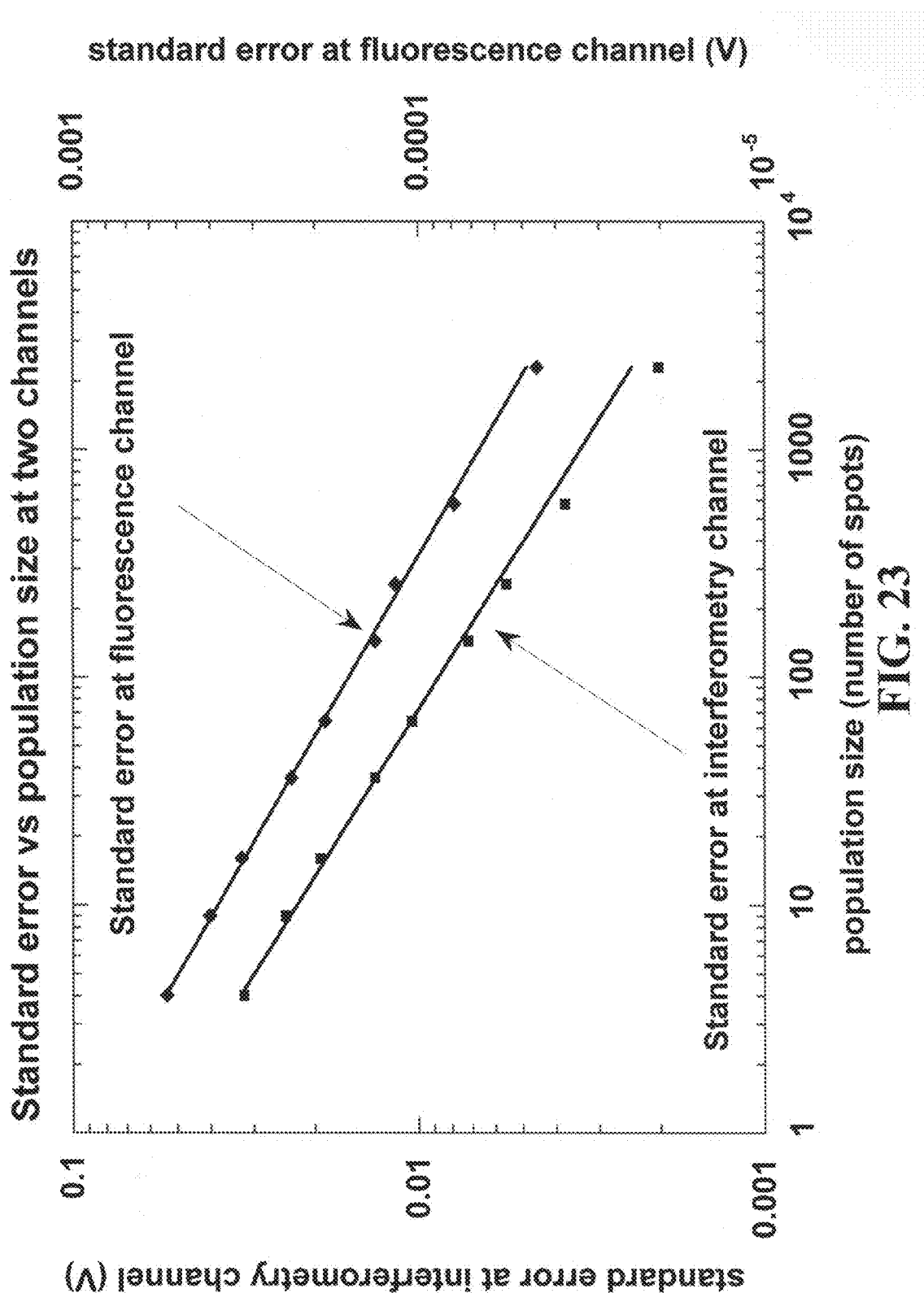
FIG. 23 shows a scaling analysis of the fluorescence and interferometry channels.

From the statistical analysis in FIG. 23, the scaling capabilities of both the fluorescence and interferometry channels can be further demonstrated by studying sub-populations of spots on the disc. Scaling is important for microarrays because it shows the potential for expanding the numbers of assay on a disc for highly multiplexed assays. The change in the standard error as the population size changes provides information about spatial correlations on the disc. The scaling analysis is shown in FIG. 23. The scaling varies nearly as the square root of the number of elements in the populations. This indicates that spatial correlations are mostly absent on the disc. The similar scaling between the fluorescence and interferometric channels provides important cross-validation of these two channels.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains.

We claim:

1. A multi-modal data acquisition system for detecting target material on a biological reaction surface, the data acquisition system comprising:
   a radiation source for generating an incoming beam to illuminate the biological reaction surface, the incoming beam impinging on the biological reaction surface and producing a reflected beam, the reflected beam being produced by the incoming beam reflecting off the biological reaction surface;
   a first detector for detecting a first signal from the illuminated biological reaction surface due to a label-free process, the reflected beam being directed to the first detector,
   a second detector for detecting a second signal from the illuminated biological reaction surface due to a labeled process; and
   a processing system for receiving the first signal and the second signal and determining the presence or absence of the target material on the biological reaction surface using the first signal and the second signal.

2. The multi-modal data acquisition system of claim 1, wherein the biological reaction surface is a biological compact disk.

3. The multi-modal data acquisition system of claim 2, wherein the incoming beam impinges on the biological reaction surface at an oblique incidence angle; and the second detector is positioned above the biological reaction surface to substantially minimize the incidence of the reflected beam on the second detector.

4. The multi-modal data acquisition system of claim 3, wherein the processing system comprises:
   an analog-to-digital converter connected to the first detector for receiving the first signal and converting the first signal into a first digital data stream, and connected to the second detector for receiving the second signal and converting the second signal into a second digital data stream; and
   a computer connected to the analog-to-digital converter for receiving the first digital data stream and the second digital data stream, and wherein the computer computes the correlation between the first digital data stream and the second digital data stream, and uses the computed correlation in determining the presence or absence of the target material on the biological compact disc.

5. The multi-modal data acquisition system of claim 1, wherein the first detector is an interferometric detector for detecting an interferometric signal from the illuminated biological reaction surface, and the second detector is a fluorescence detector for detecting a fluorescence signal from the illuminated biological reaction surface.

6. The multi-modal data acquisition system of claim 5, wherein the surface of the biological reaction surface is designed to optimize both the fluorescence and interferometric signal conditions.

7. The multi-modal data acquisition system of claim 5, wherein the biological reaction surface is designed to substantially maximize the electric field at the surface while keeping a phase condition near a pi/2 phase shift.

8. The multi-modal data acquisition system of claim 5, wherein the biological reaction surface is a biological compact disk and the incoming beam impinges on the biological compact disk at an oblique incidence angle directing the reflected beam to the interferometric detector; and wherein the fluorescence detector is positioned above the biological reaction surface and substantially perpendicular to the plane of the biological compact disk to substantially minimize the incidence of the reflected beam on the fluorescence detector.

9. The multi-modal data acquisition system of claim 8, further comprising: a spin motor upon which the biological compact disk can be mounted, for rotating the biological compact disk.

10. The multi-modal data acquisition system of claim 9, further comprising:
   a linear stage for moving the biological compact disk relative to the incoming beam, the interferometric detector and the fluorescence detector;
   wherein the rotation of the biological compact disk by the spin motor and the translation of the biological compact disk relative to the incoming beam by the linear stage creates a polar coordinate system that can be used for referencing any point on the biological compact disk.

11. The multi-modal data acquisition system of claim 5, wherein the interferometric detector is a quadrant detector configured to acquire both a phase contrast interferometric signal and an in-line quadrature interferometric signal.

12. The multi-modal data acquisition system of claim 5, wherein the processing system comprises:
   an oscilloscope connected to the interferometric detector for receiving the interferometric signal and producing digital interferometric data, and connected to the fluorescence detector for receiving the fluorescence signal and producing digital fluorescence data; and
   a computer connected to the oscilloscope for receiving the digital interferometric data and the digital fluorescence data, the computer determining the presence or absence of the target material on the biological reaction surface using the digital interferometric data and the digital fluorescence data.

13. The multi-modal data acquisition system of claim 5, further comprising: an optical filter positioned in front of the fluorescence detector to block scattered illumination from the incoming beam from impinging on the fluorescence detector.

14. The multi-modal data acquisition system of claim 5, further comprising:
   an optical filter removably positioned in front of the fluorescence detector to block scattered illumination from the incoming beam from impinging on the fluorescence detector when the optical filter is positioned in front of the fluorescence detector; and
   wherein the fluorescence detector detects both the fluorescence signal and a scattering signal, and the processing system receives both the fluorescence signal and the scattering signal from the fluorescence detector; and
   wherein, when the optical filter is positioned in front of the fluorescence detector, the fluorescence detector receives the fluorescence signal, and when the optical filter is removed from in front of the fluorescence detector, the fluorescence detector receives the scattering signal.

15. A multi-modal data acquisition system for detecting target material in a sample, the data acquisition system comprising:
   a biological compact disc having antibodies for reacting with the target material in the sample;
   a radiation source for generating an incoming beam to illuminate the biological compact disc, the incoming beam impinging on the biological compact disc at an oblique incidence angle and producing a reflected beam in the specular direction, the reflected beam being produced by the incoming beam reflecting off the biological compact disc;
   an interferometric detector for detecting an interferometric signal from the illuminated biological compact disc, the reflected beam being directed to the interferometric detector,
   a fluorescence detector for detecting a fluorescence signal from the illuminated biological compact disc; the fluorescence detector being positioned to substantially minimize the incidence of the reflected beam on the fluorescence detector; and
   an oscilloscope connected to the interferometric detector for receiving the interferometric signal and producing an interferometric digital data stream therefrom, and connected to the fluorescence detector for receiving the fluorescence signal and producing a fluorescence digital data stream therefrom; and
   a computer connected to the oscilloscope for receiving the interferometric digital data stream and the fluorescence digital data stream, and determining the presence or absence of the target material on the biological compact disc using the interferometric digital data stream and the fluorescence digital data stream.

16. The multi-modal data acquisition system of claim 15, wherein the fluorescence detector is positioned above the biological compact disc and substantially perpendicular to the plane of the biological compact disc, and wherein the system further comprises a convex lens for focusing the fluorescence signal on the fluorescence detector and a filter between the convex lens and the fluorescence detector for blocking scattered radiation from the radiation source.

17. The multi-modal data acquisition system of claim 15, further comprising:
   an optical filter removably positioned in front of the fluorescence detector to block scattered illumination from the incoming beam from impinging on the fluorescence detector when the optical filter is positioned in front of the fluorescence detector; and
   wherein the fluorescence detector detects both the fluorescence signal and a scattering signal and sends the detected signals to the oscilloscope; when the optical filter is positioned in front of the fluorescence detector, the fluorescence detector receives the fluorescence signal and the oscilloscope produces a fluorescence digital data stream therefrom; when the optical filter is removed from in front of the fluorescence detector, the fluorescence detector receives the scattering signal and the oscilloscope produces a scattering digital data stream therefrom; and the computer is capable of receiving and processing the scattering digital data stream.

18. The multi-modal data acquisition system of claim 15, wherein the interferometric detector is a quadrant detector configured to produce both a phase contrast interferometric signal and an in-line quadrature interferometric signal; the oscilloscope receiving the phase contrast interferometric signal and producing a phase contrast digital data stream therefrom and independently receiving the in-line quadrature interferometric signal and producing an in-line digital data stream therefrom; and the computer receiving and processing both the phase contrast digital data stream and the in-line digital data stream.

19. The multi-modal data acquisition system of claim 15, wherein the computer computes a correlation between the interferometric digital data stream and the fluorescence digital data stream, and uses the correlation in determining the presence or absence of the target material on the biological compact disc.

20. The multi-modal data acquisition system of claim 15, further comprising: a spin motor for rotating the biological compact disk; and
    a linear stage for moving the biological compact disk relative to the incoming beam, the interferometric detector and the fluorescence detector;
    wherein the rotation of the biological compact disk by the spin motor and the translation of the biological compact disk relative to the incoming beam by the linear stage creates a polar coordinate system that can be used for referencing any point on the biological compact disk.

21. The multi-modal data acquisition system of claim 20, wherein the spin motor is connected to the oscilloscope, and the spin motor generates a trigger signal for the oscilloscope.

22. The multi-modal data acquisition system of claim 20, wherein the computer controls the linear stage and the spin motor.

23. The multi-modal data acquisition system of claim 20, wherein the surface of the biological compact disc is designed to optimize both the fluorescence and interferometric signal conditions.

24. The multi-modal data acquisition system of claim 20, wherein the biological compact disc is designed to substantially maximize the electric field at the surface while keeping a phase condition near a pi/2 phase shift.

25. The multi-modal data acquisition system of claim 24, wherein the electric field at the surface of the biological compact disc is polarized parallel to the surface of the biological compact disc.

26. The multi-modal data acquisition system of claim 23, wherein the biological compact disc is a silicon disc coated with a silica film.

27. The multi-modal data acquisition system of claim 23, wherein the biological compact disc comprises a dielectric stack of repeated alternating layers in that the substrate has controllable reflection amplitude and phase.

28. A method of using a multi-modal data acquisition system for detecting target material on a biological compact disc, the method comprising:
    generating an incoming beam to illuminate the biological compact disc using a radiation source;
    directing the incoming beam to impinge on the biological compact disc to produce a reflected beam;
    collecting the reflected beam with an interferometric detector to produce an interferometric signal,
    collecting a fluorescence signal with a fluorescence detector,
    digitizing the interferometric signal to produce an interferometric digital data stream;
    digitizing the fluorescence signal to produce a fluorescence digital data stream; and
    correlating the interferometric digital data stream and the fluorescence digital data stream to determine the presence or absence of the target material on the biological compact disc.

29. The method of claim 28, further comprising:
    directing the incoming beam to impinge on the biological compact disc at an oblique incidence angle to produce the reflected beam in a specular direction;
    positioning the interferometric detector to collect the reflected beam reflected in the specular direction; and
    positioning the fluorescence detector to substantially minimize the incidence of the reflected beam on the fluorescence detector.

30. The method of claim 28, further comprising:
    focusing the fluorescence signal on the fluorescence detector using a convex lens; and
    filtering the fluorescence signal to eliminate scattered radiation from the radiation source.

31. The method of claim 28, further comprising:
    removably positioning an optical filter in front of the fluorescence detector to effectively block scattered illumination from the radiation source from impinging on the fluorescence detector when the optical filter is positioned in front of the fluorescence detector; and
    moving the optical filter in front of the fluorescence detector to detect the fluorescence signal with the fluorescence detector;
    removing the optical filter from in front of the fluorescence detector to detect a scattering signal with the fluorescence detector;
    digitizing the scattering signal to produce a scattering digital data stream; and
    using the scattering digital data stream in the determination of the presence or absence of the target material on the biological compact disc.

32. The method of claim 28, wherein the interferometric detector is a quadrant detector; and the method further comprises:
    simultaneously producing a phase contrast interferometric signal and an in-line quadrature interferometric signal with the quadrant detector;
    digitizing the phase contrast interferometric signal to produce a phase contrast digital data stream;
    digitizing the in-line quadrature interferometric signal to produce an in-line digital data stream; and
    using the phase contrast digital data stream and the in-line digital data stream in the determination of the presence or absence of the target material on the biological compact disc.

33. The method of claim 28, wherein the step of correlating the interferometric digital data stream and the fluorescence digital data stream comprises temporally correlating the interferometric digital data stream and the fluorescence digital data stream to determine the presence or absence of the target material on the biological compact disc.

34. The method of claim 28, wherein the step of correlating the interferometric digital data stream and the fluorescence digital data stream comprises spatially correlating the interferometric digital data stream and the fluorescence digital data stream to determine the presence or absence of the target material on the biological compact disc.

* * * * *